(12) United States Patent
Prokunina et al.

(10) Patent No.: US 10,962,539 B2
(45) Date of Patent: Mar. 30, 2021

(54) INTERFERON-λ4 (IFNL-4) PROTEIN, RELATED NUCLEIC ACID MOLECULES, AND USES THEREOF

(71) Applicant: The USA, as represented by the Secretary, Dept. of Health and Human Services, Bethesda, MD (US)

(72) Inventors: Liudmila Prokunina, Rockville, MD (US); Thomas R. O'Brien, Potomac, MD (US); Brian Muchmore, Potomac, MD (US); Raymond P. Donnelly, Damascus, MD (US); Patricia A. Porter-Gill, Little Rock, AR (US)

(73) Assignee: The USA, as represented by the Secretary, Dept. of Health and Human Services, Bethesda, MD (US)

( * ) Notice: Subject to any disclaimer, the term of this patent is extended or adjusted under 35 U.S.C. 154(b) by 0 days.

(21) Appl. No.: 15/597,459

(22) Filed: May 17, 2017

(65) Prior Publication Data
US 2017/0254808 A1 Sep. 7, 2017

Related U.S. Application Data

(62) Division of application No. 14/388,293, filed as application No. PCT/US2013/031624 on Mar. 14, 2013, now Pat. No. 9,678,074.

(60) Provisional application No. 61/616,664, filed on Mar. 28, 2012.

(51) Int. Cl.
| | |
|---|---|
| G01N 33/569 | (2006.01) |
| C07K 16/24 | (2006.01) |
| C12Q 1/68 | (2018.01) |
| C07K 14/555 | (2006.01) |
| C12Q 1/6883 | (2018.01) |
| C12Q 1/70 | (2006.01) |

(52) U.S. Cl.
CPC ..... *G01N 33/56983* (2013.01); *C07K 14/555* (2013.01); *C07K 16/249* (2013.01); *C12Q 1/6883* (2013.01); *C07K 2317/76* (2013.01); *C12Q 1/707* (2013.01); *C12Q 2600/156* (2013.01); *C12Q 2600/158* (2013.01); *G01N 2800/52* (2013.01)

(58) Field of Classification Search
None
See application file for complete search history.

(56) References Cited

U.S. PATENT DOCUMENTS

| 9,678,074 B2 | 6/2017 | Prokunina et al. | |
|---|---|---|---|
| 2002/0137137 A1* | 9/2002 | Welcher ............... | C07K 14/555 435/69.1 |

2014/0271542 A1 9/2014 Prokunina et al.

FOREIGN PATENT DOCUMENTS

| CN | 102307589 | 1/2012 |
|---|---|---|
| WO | WO 2010/135649 | 11/2010 |
| WO | WO 2010/144946 | 12/2010 |
| WO | WO 2011/013019 | 2/2011 |
| WO | WO 2011/076814 | 6/2011 |
| WO | WO 2013/001504 | 1/2013 |
| WO | WO 2013/052862 | 4/2013 |

OTHER PUBLICATIONS

Muchmore et al. (Accession No. JNB06224, Oct. 2011).*
Accession No. NP 001263188 Jun. 2020.*
Balagopal, et al., "IL28B and the Control of Hepatitis C Virus Infection", Gastroenterology, Elsevier, Philadelphia, PA, vol. 139, No. 6, Dec. 1, 2010, pp. 1865-1876.
Database EMBL, Jun. 30, 2011 (Jun. 30, 2011), "JP 2011041553-A/17: Markers for Predicting Effectiveness of Interferon Therapy," XP002697505, retrieved from EBI accession No. EM PAT: HV029596, Database accession No. HV029596 sequence.
Database Geneseq [Online], Apr. 14, 2011 (Apr. 14, 2011), "Human interferon (IFN)-lambda-3 protein sequence, SEQ: 31," XP002697504, retrieved from EBI accession No. GSP:AZF46128 Database accession No. AZF46128 sequence.
Database UniProt [Online] Mar. 6, 2013 (Mar. 6, 2013), "RecName: Full=Interferon lambda-4; Short=IFN-lambda-4; Flags: Precursor;", XP002697508, retrieved from EBI accession No. UNI PROT: K9M1U5 Database accession No. K9M1U5 sequence.
Database UniProt [Online] Jul. 27, 2011 (Jul. 27, 2011), "SubName: Full=Uncharacterized protein;", XP002697506, retrieved from EBI accession No. UNIPROT:F7ET03 Database accession No. F7ET03 sequence.
Ge et al. "Genetic variation in IL28B predicts hepatitis C treatment-induced viral clearance," Nature, Sep. 2009, vol. 461, pp. 399-401 and Accession No. NP 001263183.2.
Iulio, J., et al., "Estimating the net contribution of interleukin-28B variation to spontaneous hepatitis C virus clearance", Hepatology, vol. 53, No. 5, Apr. 22, 2011, pp. 1446-1454.
Lange, C.M., et al., "IL28B single nucleotide polymorphisms in the treatment of hepatitis C", Journal of Hepatology, vol. 55, No. 3, Sep. 1, 2011, pp. 692-701.
Prokunina-Olsson et al. "A variant upstream of IFNL3 (IL28B) creating a new interferon gene IFNL4 is associated with impaired clearance of hepatitis C virus," Nature Genetics, Feb. 2013, vol. 45, No. 2, pp. 164-171.
Smith, K.R., et al., "Identification of improved IL28B SNPs and haplotypes for prediction of drug response in treatment of hepatitis C using massively parallel sequencing in a cross-sectional European cohort", Genome Medicine, vol. 3, No. 57, Aug. 31, 2011, pp. 1-13.
Rauch et al. "Genetic Variation in IL28B Is Associated With Chronic Hepatitis C and Treatment Failure: A Genome-Wide Association Study," Gatroenterology, 2010, vol. 138, pp. 1338-1345.

(Continued)

*Primary Examiner* — Agnieszka Boesen
(74) *Attorney, Agent, or Firm* — Sheridan Ross P.C.

(57) ABSTRACT

The invention is related to identification of an interferon-analog (IFNL4) protein and genetic association with spontaneous clearance of HCV infection and response to treatment for HCV infection.

19 Claims, 21 Drawing Sheets

Specification includes a Sequence Listing.

(56) References Cited

OTHER PUBLICATIONS

Tanaka et al. "Genome-wide association of IL28B with response to pegylated interferon-alpha and ribavirin therapy for chronic hepatitis C," Nature Genetics, Oct. 2009, vol. 41, No. 10, pp. 1105-1109.
Thomas et al. "Genetic variation in IL28B and spontaneous clearance of hepatitis C virus," Nature, Oct. 2009, vol. 461, pp. 798-801.
International Search Report and Written Opinion for PCT/US12/59048, dated Jan. 16, 2013.
International Search Report and Written Opinion for PCT/US13/31624, dated Jun. 11, 2013.
Official Action with English Translation for China Patent Application No. 201380028364.4, dated Jun. 27, 2016 28 pages.
Official Action with English Translation for China Patent Application No. 201380028364.4, dated Mar. 27, 2017 22 pages.
Official Action for U.S. Appl. No. 14/349,395, dated Aug. 13, 2015 10 pages Restriction Requirement.
Official Action for U.S. Appl. No. 14/349,395, dated Feb. 1, 2016 23 pages.
Official Action for U.S. Appl. No. 14/349,395, dated Sep. 8, 2016 12 pages.
Official Action for U.S. Appl. No. 14/388,293, dated Feb. 24, 2016 8 pages Restriction Requirement.
Official Action for U.S. Appl. No. 14/388,293, dated Jul. 28, 2016 8 pages.
Notice of Allowance for U.S. Appl. No. 14/388,293, dated Feb. 10, 2017 5 pages.
Official Action for European Patent Application No. 13712655.3, dated Mar. 16, 2018 4 pages.
Official Action for European Patent Application No. 13712655.3, dated Feb. 24, 2016 3 pages.
Official Action for European Patent Application No. 13712655.3, dated May 3, 2017 6 pages.
Grimwood et al. "The DNA sequence_and_biology of human chromosome 19," Nature, Apr. 2004, vol. 428, No. 6982, pp. 529-535.
Onabajo et al. "Expression of Interferon Lambda 4 Is Associated with Reduced Proliferation and Increased Cell Death in Human Hepatic Cells," Journal of Interferon & Cytokine Research, 2015, vol. 35, No. 11, pp. 888-900.
Notice of Acceptance for Australia Patent Application No. 2013240301, dated Sep. 20, 2017 3 pages.
Official Action for Canada Patent Application No. 2,869,899, dated Nov. 2, 2016 3 pages.
Official Action for Canada Patent Application No. 2,869,899, dated Nov. 9, 2017 3 pages.
Official Action with English Translation for China Patent Application No. 201380028364.4, dated Nov. 14, 2017 19 pages.
English Translation of Official Action for Japan Patent Application No. 2015-503310, dated Nov. 4, 2015 3 pages.
English Translation of Official Action for Japan Patent Application No. 2015-503310, dated Mar. 8, 2016 2 pages.
Decision to Grant with English Translation for Japan Patent Application No. 2015-503310, dated Mar. 7, 2017 6 pages.
Official Action for Canada Patent Application No. 2,869,899, dated Oct. 25, 2018 4 pages.
Official Action with English Translation for China Patent Application No. 201380028364.4, dated Sep. 3, 2018 14 pages.
Official Action for India Patent Application No. 8806/DELNP/2014, dated Mar. 28, 2019 7 pages.
Bamford, et al., "A Polymorphic residue that attenuates the antiviral potential of interferon lambda 4 in hominid lineages", PLOS Pathogens, Oct. 11, 2018, pp. 1-35.

\* cited by examiner

Fig. 4

| Transcript ID, NCBI accession number | Exons | mRNA | Protein | ss469415590 allele | Annotation |
|---|---|---|---|---|---|
| IFNL4, p179, JN806234 | 5 | 1636 bp | 179 aa | ΔG | *Similarity to IFNL3, full-length protein |
| p131, JN806225 | 4 | 1492 bp | 131 aa | ΔG | Similarity to IFNL3, full-length protein |
| p107, JN806226 | 3 | 1420 bp | 107 aa | ΔG | Similarity to IFNL3, full-length protein |
| JN806232 | 3 | 1131 bp | 93 aa | ΔG | No similarity, protein fragment |
| p170, JN806233 | 3 | 915 bp | 170 aa | ΔG | No similarity, full-length protein |
| JN806227 | 3 | 1637 bp | 123 aa | TT | No similarity, protein fragment |
| JN806228 | 2 | 1493 bp | 75 aa | TT | No similarity, protein fragment |
| JN806229 | 1 | 1421 bp | 51 aa | TT | No similarity, protein fragment |
| p124, JN806230 | 3 | 916 bp | 124 aa | TT | No similarity, full-length protein |
| p143, JN806231 | 3 | 1132 bp | 143 aa | TT | No similarity, full-length protein |

Transcripts identified within IFNL4 region and submitted to NCBI GenBank

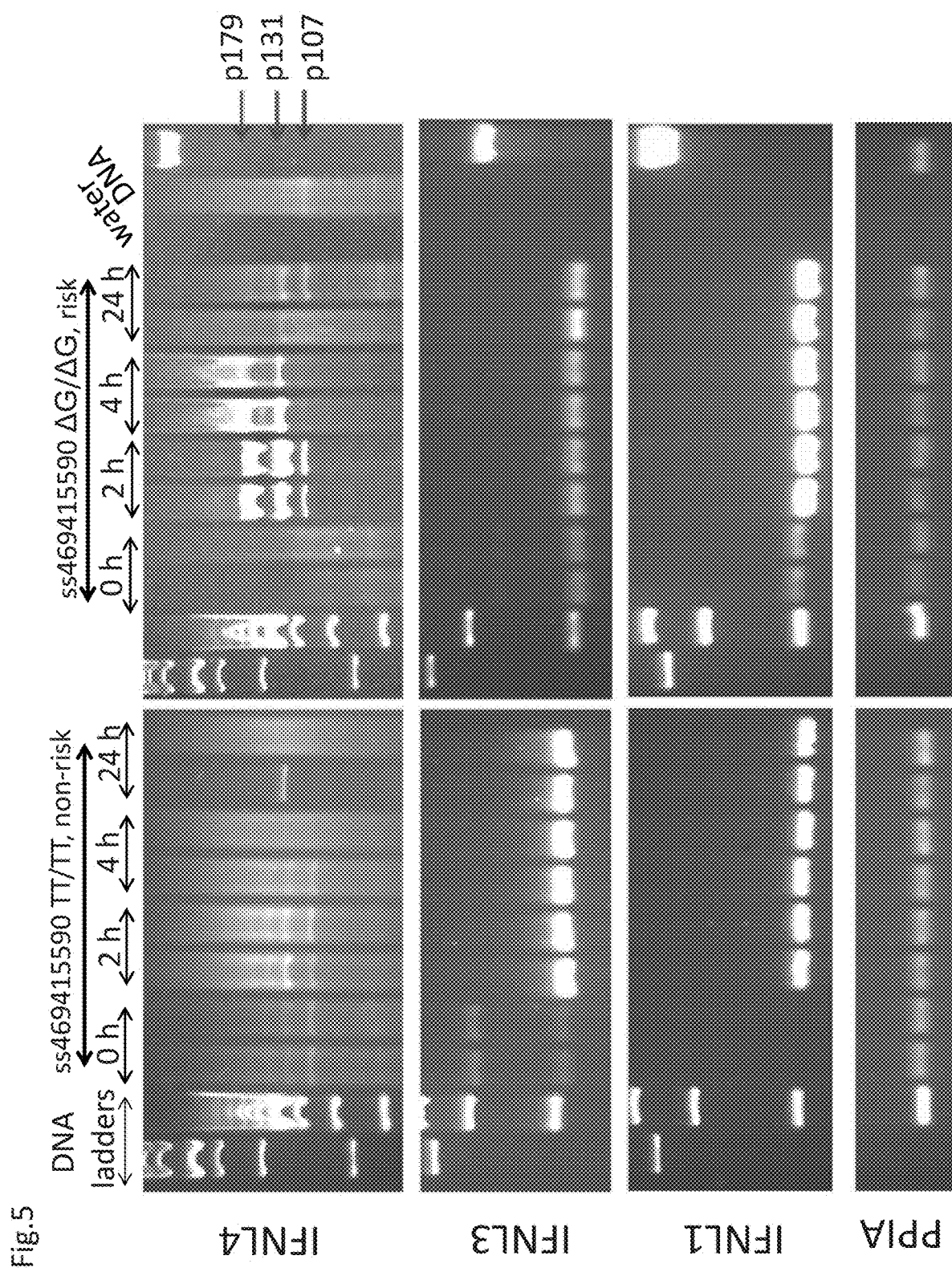

Fig.6

| Protein | p179 (IFNL4) | IFNL3 | IFNL1 | IFNL2 | IFN-α1 | IL-10 | IL-22 | IFN-β1 |
|---|---|---|---|---|---|---|---|---|
| Type | IFN III? | IFN III | IFN III | IFN III | IFN I | IL-10 family | IL-10 family | IFN I |
| mRNA | JN806234 | NM_172139 | NM_172140 | NM_172138 | NM_002175 | NM_000572 | NM_020525 | NM_002176 |
| Protein ID | AFQ38559 | Q8IZI9 | Q8IU54 | Q45KQ8 | P05014 | Q6FGW4 | Q9GZX6 | Q5VWC9 |
| Size, amino acids | 179 | 196 | 200 | 200 | 189 | 178 | 179 | 187 |
| Exons | 5 | 5 | 5 | 6 | 1 | 5 | 5 | 1 |
| Identity with p179, n amino acids (%) | — | 52 (29.1) | 48 (26.8) | 47 (26.3) | 26 (14.5) | 24 (13.4) | 20 (11.1) | 20 (11.1) |
| Similarity with p179, n amino acids (%) | — | 73 (40.8) | 66 (36.8) | 70 (39.1) | 47 (26.2) | 40 (22.3) | 45 (25.1) | 44 (24.5) |

Comparisons between IFNL4 (p179) protein and selected members of the class 2 cytokine family Alignment of protein sequences for IFNL4 isoforms p179, p131 and p107 with related interferons Western blot detection of IFNAN and other recombinant proteins by the mouse anti-IFNL4 antibody Analysis of biological activity of 83 IFNL4 mutants generated by site-directed mutagenesis, Based on their ability to activate ISRE-Luc reporter in HepG2 cells, compared wild-type IFNL4

Fig. 19

| IFNL4 allelic protein isoform | rs73555604 G/A Cys17Tyr | Rs142981501 G/C Arg60Pro | Rs117648444 C/T Pro70Ser |
|---|---|---|---|
| WT | Cys | Arg | Pro |
| Cys17Tyr | Tyr | Arg | Pro |
| Arg60Pro | Cys | Pro | Pro |
| Pro70Ser | Cys | Arg | Ser |

SEQUENCE LISTING

<160> NUMBER OF SEQ ID NOS: 23

<210> SEQ ID NO 1
<211> LENGTH: 540
<212> TYPE: DNA
<213> ORGANISM: Homo sapiens

<400> SEQUENCE: 1

```
atgcggccga gtgtctgggc cgcagtggcc gcggggctgt gggtcctgtg cacggtgatc     60
gcagcggccc cccggcgctg cctgctctcg cactaccgct cgctggagcc ccggacgctg    120
gcggctgcca aggcgctgag ggaccgctac gaggaagagg cgctgagctg ggggcagcgc    180
aactgctcct tccgcccag gagggattct ccgcggccat cgtcctgcgc tcggctccgc     240
cacgtggccc gggcatcgc ggacgcccag gcagtgctca gcggcctgca ccgctcggag     300
ctgctccccg cgccggccc gatcctggag ctgctggcgg ccgcggggag ggatgtggcg    360
gcctgccttg agctggcacg gccaggctcc tccaggaagg tccccggggc ccagaagagg    420
cgtcacaaac cccggagagc ggactcccct cggtgccgca aggccagcgt ggtcttcaac    480
ctcctgcgcc tgctcacgtg ggagctccgg ctggctgcac actctgggcc ttgcctctga    540
```

<210> SEQ ID NO 2
<211> LENGTH: 179
<212> TYPE: PRT
<213> ORGANISM: Homo sapiens

<400> SEQUENCE: 2

```
Met Arg Pro Ser Val Trp Ala Ala Val Ala Ala Gly Leu Trp Val Leu
1               5                   10                  15

Cys Thr Val Ile Ala Ala Ala Pro Arg Arg Cys Leu Leu Ser His Tyr
            20                  25                  30

Arg Ser Leu Glu Pro Arg Thr Leu Ala Ala Ala Lys Ala Leu Arg Asp
        35                  40                  45

Arg Tyr Glu Glu Glu Ala Leu Ser Trp Gly Gln Arg Asn Cys Ser Phe
    50                  55                  60

Arg Pro Arg Arg Asp Ser Pro Arg Pro Ser Ser Cys Ala Arg Leu Arg
65                  70                  75                  80

His Val Ala Arg Gly Ile Ala Asp Ala Gln Ala Val Leu Ser Gly Leu
                85                  90                  95

His Arg Ser Glu Leu Leu Pro Gly Ala Gly Pro Ile Leu Glu Leu Leu
            100                 105                 110

Ala Ala Ala Gly Arg Asp Val Ala Ala Cys Leu Glu Leu Ala Arg Pro
        115                 120                 125

Gly Ser Ser Arg Lys Val Pro Gly Ala Gln Lys Arg Arg His Lys Pro
    130                 135                 140

Arg Arg Ala Asp Ser Pro Arg Cys Arg Lys Ala Ser Val Val Phe Asn
145                 150                 155                 160

Leu Leu Arg Leu Leu Thr Trp Glu Leu Arg Leu Ala Ala His Ser Gly
                165                 170                 175

Pro Cys Leu
```

<210> SEQ ID NO 3
<211> LENGTH: 540
<212> TYPE: DNA
<213> ORGANISM: Homo sapiens

<400> SEQUENCE: 3

```
tcagaggcaa ggcccagagt gtgcagccag ccggagctcc cacgtgagca ggcgcaggag     60
gttgaagacc acgctggcct tgcggcaccg aggggagtcc gctctccggg gtttgtgacg    120
cctcttctgg gccccgggga ccttcctgga ggagcctggc cgtgccagct caaggcaggc    180
cgccacatcc ctccccgcgg ccgccagcag ctccaggatc gggccggcgc cggggagcag    240
```

```
ctccgagcgg tgcaggccgc tgagcactgc ctgggcgtcc gcgatgcccc gggccacgtg      300
gcggagccga gcgcaggacg atggccgcgg agaatccctc ctggggcgga aggagcagtt      360
gcgctgcccc cagctcagcg cctcttcctc gtagcggtcc ctcagcgcct ggcagccgc       420 cagcgtccgg ggctccagcg agcggtagtg cgagagcagg cagcgccggg gggccgctgc      480
gatcaccgtg cacaggaccc acagccccgc ggccactgcg cccagacac  tcggccgcat      540
```

<210> SEQ ID NO 4
<211> LENGTH: 396
<212> TYPE: DNA
<213> ORGANISM: Homo sapiens

<400> SEQUENCE: 4

```
atgcggccga gtgtctgggc cgcagtggcc gcggggctgt gggtcctgtg cacggtgatc       60
gcagcggccc cccggcgctg cctgctctcg cactaccgct cgctggagcc ccggacgctg      120
gcggctgcca aggcgctgag ggaccgctac gaggaagagg cgctgagctg ggggcagcgc      180
aactgctcct tccgccccag gagggattct ccgcggccat cgcttgagct ggcacggcca      240
ggctcctcca ggaaggtccc cggggcccag aagaggcgtc acaaaccccg agagcggac      300 tcgcctcggt gccgcaaagc cagcgtggtc ttcaacctcc tgcgcctgct cacgtgggag      360
ctccggctgg ctgcacactc tgggccttgc ctctga                               396
```

<210> SEQ ID NO 5
<211> LENGTH: 131
<212> TYPE: PRT
<213> ORGANISM: Homo sapiens

<400> SEQUENCE: 5

```
Met Arg Pro Ser Val Trp Ala Ala Val Ala Ala Gly Leu Trp Val Leu
1               5                   10                  15

Cys Thr Val Ile Ala Ala Ala Pro Arg Arg Cys Leu Leu Ser His Tyr
            20                  25                  30

Arg Ser Leu Glu Pro Arg Thr Leu Ala Ala Ala Lys Ala Leu Arg Asp
        35                  40                  45

Arg Tyr Glu Glu Glu Ala Leu Ser Trp Gly Gln Arg Asn Cys Ser Phe
    50                  55                  60

Arg Pro Arg Arg Asp Ser Pro Arg Pro Ser Leu Glu Leu Ala Arg Pro
65                  70                  75                  80

Gly Ser Ser Arg Lys Val Pro Gly Ala Gln Lys Arg Arg His Lys Pro
                85                  90                  95

Arg Arg Ala Asp Ser Pro Arg Cys Arg Lys Ala Ser Val Val Phe Asn
            100                 105                 110

Pro Leu Arg Leu Leu Thr Trp Glu Leu Arg Leu Ala Ala His Ser Gly
        115                 120                 125

Pro Cys Leu
    130
```

<210> SEQ ID NO 6
<211> LENGTH: 396
<212> TYPE: DNA
<213> ORGANISM: Homo sapiens

<400> SEQUENCE: 6

```
tcagaggcaa ggcccagagt gtgcagccag ccggagctcc cacgtgagca ggcgcaggag       60
gttgaagacc acgctggctt tgcggcaccg aggcgagtcc gctctccggg gtttgtgacg      120
```

```
cctcttctgg gccccgggga ccttcctgga ggagcctggc cgtgccagct caagcgatgg      180
ccgcggagaa tccctcctgg ggcggaagga gcagttgcgc tgccccagc tcagcgcctc       240 ttcctcgtag cggtccctca gcgccttggc agccgccagc gtccggggct ccagcgagcg      300
gtagtgcgag agcaggcagc gccggggggc cgctgcgatc accgtgcaca ggacccacag     360
ccccgcggcc actgcggccc agacactcgg ccgcat                                 396
```

<210> SEQ ID NO 7
<211> LENGTH: 324
<212> TYPE: DNA
<213> ORGANISM: Homo sapiens

<400> SEQUENCE: 7

```
atgcggccga gtgtctgggc cgcagtggcc gcggggctgt gggtcctgtg cacggtgatc     60
gcagcggccc ccggcgctg cctgctctcg cactaccgct cgctggagcc ccggacgctg      120
gcggctgcca aggcgctgag ggaccgctac cttgagctgg cacggccagg ctcctccagg     180
aaggtccccg ggcccagaa gaggcgtcac aaaccccgga gagcggactc gcctcggtgc       240
cgcaaagcca gcgtggtctt caacctcctg cgcctgctca gtgggagct ccggctggct       300 gcacactctg ggccttgcct ctga                                               324
```

<210> SEQ ID NO 8
<211> LENGTH: 107
<212> TYPE: PRT
<213> ORGANISM: Homo sapiens

<400> SEQUENCE: 8

Met Arg Pro Ser Val Trp Ala Ala Val Ala Ala Gly Leu Trp Val Leu
1               5                   10                  15

Cys Thr Val Ile Ala Ala Ala Pro Arg Arg Cys Leu Leu Ser His Tyr
                20                  25                  30

Arg Ser Leu Glu Pro Arg Thr Leu Ala Ala Ala Lys Ala Leu Arg Asp
            35                  40                  45

Arg Tyr Leu Glu Leu Ala Arg Pro Gly Ser Ser Arg Lys Val Pro Gly
        50                  55                  60

Ala Gln Lys Arg Arg His Lys Pro Arg Arg Ala Asp Ser Pro Arg Cys
65                  70                  75                  80

Arg Lys Ala Ser Val Val Phe Asn Pro Leu Arg Leu Leu Thr Trp Glu
                85                  90                  95

Leu Arg Leu Ala Ala His Ser Gly Pro Cys Leu
            100                 105

<210> SEQ ID NO 9
<211> LENGTH: 324
<212> TYPE: DNA
<213> ORGANISM: Homo sapiens

<400> SEQUENCE: 9

```
tcagaggcaa ggcccagagt gtgcagccag ccggagctcc cacgtgagca ggcgcaggag     60
gttgaagacc acgctggctt tgcggcaccg aggcgagtcc gctctccggg gtttgtgacg      120
cctcttctgg gccccgggga ccttcctgga ggagcctggc cgtgccagct caaggtagcg      180
gtccctcagc gccttggcag ccgccagcgt ccggggctcc agcgagcggt agtgcgagag      240
caggcagcgc cggggggccg ctgcgatcac cgtgcacagg acccacagcc ccgcggccac      300
tgcggcccag acactcggcc gcat                                               324
```

```
<210> SEQ ID NO 10
<211> LENGTH: 9
<212> TYPE: PRT
<213> ORGANISM: Homo sapiens

<400> SEQUENCE: 10

Cys Leu Met Asp Arg His Asp Phe Gly
1               5

<210> SEQ ID NO 11
<211> LENGTH: 18
<212> TYPE: PRT
<213> ORGANISM: Homo sapiens

<400> SEQUENCE: 11

Asp Glu Asp Leu Leu Asp Lys Phe Cys Thr Glu Leu Tyr Gln Gln Leu
1               5                   10                  15

Asn Asp

<210> SEQ ID NO 12
<211> LENGTH: 16
<212> TYPE: PRT
<213> ORGANISM: Homo sapiens

<400> SEQUENCE: 12

Tyr Phe Arg Arg Ile Thr Leu Tyr Leu Thr Glu Lys Lys Tyr Ser Pro
1               5                   10                  15

<210> SEQ ID NO 13
<211> LENGTH: 21
<212> TYPE: DNA
<213> ORGANISM: Artificial Sequence
<220> FEATURE:
<223> OTHER INFORMATION: Synthetic Primer

<400> SEQUENCE: 13
gcctgctgca gaagcagaga t                                           21

<210> SEQ ID NO 14
<211> LENGTH: 17
<212> TYPE: DNA
<213> ORGANISM: Artificial Sequence
<220> FEATURE:
<223> OTHER INFORMATION: Synthetic Primer

<400> SEQUENCE: 14
agccgagcgc aggacga                                                17

<210> SEQ ID NO 15
<211> LENGTH: 13
<212> TYPE: DNA
<213> ORGANISM: Artificial Sequence
<220> FEATURE:
<223> OTHER INFORMATION: Synthetic Primer

<400> SEQUENCE: 15
atcgcagaag gcc                                                    13

<210> SEQ ID NO 16
<211> LENGTH: 13
<212> TYPE: DNA
<213> ORGANISM: Artificial Sequence
<220> FEATURE:
<223> OTHER INFORMATION: Synthetic Primer
```

```
<400> SEQUENCE: 16
atcgcagcgg ccc                                                          13

<210> SEQ ID NO 17
<211> LENGTH: 21
<212> TYPE: DNA
<213> ORGANISM: Artificial Sequence
<220> FEATURE:
<223> OTHER INFORMATION: Synthetic Primer

<400> SEQUENCE: 17
gcctgctgca gaagcagaga t                                                 21

<210> SEQ ID NO 18
<211> LENGTH: 19
<212> TYPE: DNA
<213> ORGANISM: Artificial Sequence
<220> FEATURE:
<223> OTHER INFORMATION: Synthetic Primer

<400> SEQUENCE: 18
gctccagcga gcggtagtg                                                    19

<210> SEQ ID NO 19
<211> LENGTH: 13
<212> TYPE: DNA
<213> ORGANISM: Artificial Sequence
<220> FEATURE:
<223> OTHER INFORMATION: Synthetic Primer

<400> SEQUENCE: 19
atcgcagaag gcc                                                          13

<210> SEQ ID NO 20
<211> LENGTH: 13
<212> TYPE: DNA
<213> ORGANISM: Artificial Sequence
<220> FEATURE:
<223> OTHER INFORMATION: Synthetic Primer

<400> SEQUENCE: 20
atcgcagcgg ccc                                                          13

<210> SEQ ID NO 21
<211> LENGTH: 21
<212> TYPE: DNA
<213> ORGANISM: Artificial Sequence
<220> FEATURE:
<223> OTHER INFORMATION: Synthetic Primer

<400> SEQUENCE: 21
atgcggccga gtgtctgggc c                                                 21

<210> SEQ ID NO 22
<211> LENGTH: 23
<212> TYPE: DNA
<213> ORGANISM: Artificial Sequence
<220> FEATURE:
<223> OTHER INFORMATION: Synthetic Primer

<400> SEQUENCE: 22
gaggcaaggc ccagagtgtg cag                                               23

<210> SEQ ID NO 23
```

```
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 23

Lys Ala Leu Arg Asp Arg Tyr Glu Glu Glu Ala Leu Ser Trp Gly Gln
1               5                   10                  15

Arg Asn Cys Ser Phe Arg Pro Arg Arg Asp Ser Pro Arg Pro Ser
            20                  25                  30
```

INTERFERON-λ4 (IFNL-4) PROTEIN, RELATED NUCLEIC ACID MOLECULES, AND USES THEREOF

CROSS REFERENCE TO RELATED APPLICATIONS

This application is a divisional of U.S. patent application Ser. No. 14/388,293, filed Sep. 26, 2014, now U.S. Pat. No. 9,678,074, issued Jun. 13, 2017, which is a national stage application under 35 U.S.C. 371 and claims the benefit of PCT Application No. PCT/US2013/031624 having an international filing date of Mar. 14, 2013, which designated the United States, which PCT application claimed the benefit of U.S. Provisional Application No. 61/616,664 filed Mar. 28, 2012, the disclosure of both the above-identified applications are incorporated herein by reference.

REFERENCE TO SEQUENCE LISTING

This application contains a Sequence Listing submitted as an electronic text file named "6137NCI-30-PROV-1_sequence_listing_ST25.txt", having a size in bytes of 11KB, and created on Mar. 14, 2013. The information contained in this electronic file is hereby incorporated by reference in its entirety pursuant to 37 CFR § 1.52(e)(5).

TECHNICAL FIELD

The present invention is related to identification of a novel human interferon, designated as interferon-λ4 (IFNL4) and methods of using its mRNA, protein expression or protein activity to predict the clinical outcome of an HCV infection in an individual. It also relates to the use of the novel protein to identify novel compounds for treating an HCV infection.

BACKGROUND OF INVENTION

Hepatitis C virus (HCV) is a single-stranded RNA virus in the Flaviviridae family of viruses. It is estimated that approximately 170 million people worldwide, and at least 4 million people in the United States, have been infected with HCV (Thomas D L, Astemborski J, Rai R M, Anania F A, Schaeffer M, Galai N, Nolt K, Nelson K E, Strathdee S A, Johnson L, Laeyendecker O, Boitnott J, Wilson L E, Vlahov D., The Natural History of Hepatitus C Virus Infection. JAMA 2000; 284 (4): 450-456). In the US, more people die of HCV than HIV infection (Ly, K., Xing J, Klevens R M, Jiles R B, Ward J W, Holmberg S D. The Increasing Burden of Mortality From Viral Hepatitis in the United States Between 1999 and 2007. *Annals of Internal Medicine* 156, 271-278 (2012).) Thus, infection with HCV represents a significant, worldwide health problem.

In most people, acute infection with HCV generally results in mild symptoms such as fatigue, decreased appetite, and flu-like symptoms. By convention, acute hepatitis refers to the presence of clinical signs or symptoms of hepatitis for a period of 6 months or fewer after the presumed time of exposure. In some instances, however, the newly infected individual remains asymptomatic. While some individuals can spontaneously clear the virus, approximately 85% of people infected with HCV will develop chronic hepatitis C, which is defined as persistent viremia occurring at least 6 months after initial exposure (Blackard J T, Shata M T, Shire N J, Sherman K E., Acute Hepatitus C Virus Infection: A Chronic Problem., Hepatology 2008; 47(1):321-331). Chronic infection with HCV is a leading cause of liver cancer and end-stage liver disease. It is also the most common reason for liver transplantation in the U.S. Currently, the standard treatment for HCV infections is pegylated interferon-α (IFN-α) combined with ribavirin. Successful treatment resolves chronic HCV infection, thereby markedly reducing HCV related morbidity and mortality, but the pegylated IFN-α/ribavirin regimen is effective in less than 45% of patients, is expensive and has many adverse effects. More recently, a triple therapy comprising pegylated-IFN-α, ribavirin, and an HCV protease inhibitor has been recommended. Although this new regimen should be more efficacious than treatment with pegylated-interferon-α/ribavirin, a sizeable proportion of patients may fail to respond and patients treated with this regimen will experience the adverse effects seen with pegylated-IFN-α/ribavirin therapy. Thus, a method of identifying patients who are unlikely to respond to treatment with interferon-based therapies is urgently desired so that these patients can be spared the expense and adverse effects associated with futile treatment. In addition, the failure of some patients to respond to treatment indicates the need for new treatments for hepatitis C infections.

Increasing evidence suggests that host genetic factors influence both the natural course of chronic HCV infection and response to therapy (Lauer G M, Walker B D. Hepatitis C virus infection. N Engl J Med 2001 Jul. 5; 345(1):41-52; Manns M P, McHutchison J G, Gordon S C, Rustgi V K, Shiffman M, Reindollar R, et al. Peginterferon alfa-2b plus ribavirin compared with interferon alfa-2b plus ribavirin for initial treatment of chronic hepatitis C: a randomised trial. Lancet 2001 Sep. 22; 358(9286):958-965; Fried M W, Shiffman M L, Reddy K R, Smith C, Marinos G, Goncales F L, Jr., et al. Peginterferon α-2a plus ribavirin for chronic hepatitis C virus infection. N Engl J Med 2002 Sep. 26; 347(13):975-982; Kau A, Vermehren J, Sarrazin C. Treatment predictors of a sustained virologic response in hepatitis B and C. J Hepatol 2008 October; 49(4):634-651). For example, in two cohorts of pregnant women infected under similar conditions from immunoglobulin preparations contaminated with a single strain of HCV, half spontaneously cleared the infection and half progressed to chronic hepatitis C (Grakoui A, Shoukry N H, Woollard D J, Han J H, Hanson H L, Ghrayeb J, et al. HCV persistence and immune evasion in the absence of memory T cell help. Science 2003 Oct. 24; 302(5645):659-662; Knapp S, Yee L J, Frodsham A J, Hennig B J, Hellier S, Zhang L, et al. Polymorphisms in interferon-induced genes and the outcome of hepatitis C virus infection: roles of MxA, OAS-1 and PKR. Genes Immun 2003 September; 4(6):411-419). Among chronically infected patients, response to treatment differs, even between cases with similar HCV-RNA levels and identical genotypes (Thio C L. Host genetic factors and antiviral immune responses to hepatitis C virus. Clin Liver Dis 2008 August; 12(3):713-26, xi.; Yee L J. Host genetic determinants in hepatitis C virus infection. Genes Immun 2004 June; 5(4):237-245; Muller R. The natural history of hepatitis C: clinical experiences. J Hepatol 1996; 24(2 Suppl): 52-54). The response rates are strongly associated with ethnicity (Conjeevaram, H. S. et al. Peginterferon and ribavirin treatment in African American and Caucasian American patients with hepatitis C genotype 1. Gastroenterology, 131:470-7 (2006)). Previous reports revealed the influence of genetic polymorphisms of human leukocyte antigens (HLA) (Sheppard, P. et al. IL-28, IL-29 and their class II cytokine receptor IL-28R. Nat Immunol 4, 63-8 (2003); Robek, M. D., Boyd, B. S. & Chisari, F. V. Lambda interferon inhibits hepatitis B and C virus replication. J.

Virol. 79, 3851-3854 (2005)), killer immunoglobulin-like receptors (KIRs) (Lauterbach, H. et al. Mouse CD8alpha+ DCs and human BDCA3+ DCs are major producers of IFN-lambda in response to Poly I:C. J Exp Med 207, 2703-17), cytokines (WO 00/08215), chemokines and interleukins as well as interferon-stimulated genes on HCV infection outcomes (Lasfar, A. et al. Characterization of the mouse IFN-lambda ligand-receptor system: IFN-lambdas exhibit antitumor activity against B16 melanoma. Cancer Res 66, 4468-77 (2006); Phillips, J. E. & Corces, V. G. CTCF: master weaver of the genome. Cell 137, 1194-211 (2009); Shyu, A. B., Wilkinson, M. F. & van Hoof, A. Messenger RNA regulation: to translate or to degrade. EMBO J 27, 471-81 (2008); Conjeevaram, H. S. et al. Peginterferon and ribavirin treatment in African American and Caucasian American patients with hepatitis C genotype 1. Gastroenterology 131, 470-7 (2006); Ghany, M., Nelson, D. R., Strader, D. B., Thomas, D. L. & Seeff, L. B. An update on treatment of genotype 1 chronic hepatitis c virus infection: 2011 practice guidelines by the American association for the Study of Liver Diseases. Hepatology, December 12 (doi: 10.1002/hep.25524) (2011).

Previous studies have used a candidate gene approach based on a priori knowledge of the potential role of a gene in HCV infection. However, previous data do not allow accurate prediction of spontaneous clearance or response to treatment (Robek, M. D., Boyd, B. S. & Chisari, F. V. Lambda interferon inhibits hepatitis B and C virus replication. J. Virol. 79, 3851-3854 (2005)). In 2009, several groups reported results from independent genome-wide association studies (GWAS) that identified single nucleotide polymorphisms (SNPs) in the IFNL3 (IL28B) gene region that are associated with response to pegylated IFN-α/ribavirin treatment among patients with chronic hepatitis C, as well as spontaneous clearance of HCV infection. For example, U.S. Patent Publication No. 2011/0165124 by Bochud et al, which is incorporated herein in its entirety by reference, discloses numerous SNPs associated with both response to interferon-based treatment of HCV, and spontaneous clearance. Among the SNPs identified in these GWAS, the genotype based on rs12979860 is currently accepted as the best predictor of spontaneous clearance and treatment response (Rauch, A. et al. Genetic variation in IL28B Is associated with chronic hepatitis C and treatment failure: a genome-wide association study. Gastroenterology 138, 1338-1345 (2010); Thomas, D. L. et al. Genetic variation in IL28B and spontaneous clearance of hepatitis C virus. Nature 461, 798-801 (2009); Ge, D. et al. Genetic variation in IL28B predicts hepatitis C treatment-induced viral clearance. Nature 461, 399-401 (2009); Suppiah, V. et al. IL28B is associated with response to chronic hepatitis C interferon-alpha and ribavirin therapy. Nat Genet 41, 1100-4 (2009); Tanaka, Y. et al. Genome-wide association of IL28B with response to pegylated interferon-alpha and ribavirin therapy for chronic hepatitis C. Nat Genet 41, 1105-9 (2009)). A single nucleotide polymorphism (SNP) rs12979860 is located approximately 3 kb upstream of the IFNL3 (IL28B) translational start site. Commercial laboratory tests based on rs12979860 are now available for predicting a patient's probability of responding to treatment.

Compared to persons of European ancestry, African American patients have a higher frequency of chronic hepatitis C and a poorer response to therapy with IFN-α/ribavirin. Racial differences in the frequency of GWAS marker rs12979860 do not completely explain these disparities. Identification of a genetic marker that has optimal predictive values in all population groups would improve clinical decision models for treatment of chronic hepatitis C and help deliver personalized medicine to all HCV-infected patients.

While current tests have proved to be useful in identifying responders to treatment of chronic HCV infection, there remains a need for a more robust and accurate test for predicting spontaneous clearance and response to treatment. Moreover, current tests require the isolation and genotyping of nucleic acid molecules from an individual. Finally, as noted above, there remains a percentage of the population who do not respond to treatment for chronic HCV infection with current therapies. Thus, a need exists for novel methods and treatments for these patients. The present invention satisfies these needs and provides other benefits as well.

SUMMARY OF INVENTION

The invention is related to identification of a novel human protein, interferon-λ4 (IFNL4), and related nucleic acid molecules (e.g., DNA, mRNA), and their relation to spontaneous clearance of HCV infection and response to treatment for HCV infection.

In one embodiment, the invention provides an isolated protein that comprises contiguous amino acids from an amino acid sequence selected from the group consisting of SEQ ID NO:2, SEQ ID NO:5 and SEQ ID NO:8. In specific embodiments, the isolated protein activates the JAK/STAT-signal transduction pathway. In specific embodiments, the isolated protein comprises at least about 30, at least about 40, at least about 60, at least about 80, at least about 100, at least about 110, at least about 140 contiguous amino acids from an amino acid sequence selected from the group consisting of SEQ ID NO:2, SEQ ID NO:5 and SEQ ID NO:8.

In one embodiment, the isolated protein comprises a sequence of at least 50 contiguous amino acids, wherein the at least 50 contiguous amino acid sequence is at least 92% identical over its entire length to an at least 50 contiguous amino acid sequence from an amino acid sequence selected from the group consisting of SEQ ID NO:2, SEQ ID NO:5 and SEQ ID NO:8.

In one embodiment, the isolated protein comprises a sequence of at least 150 contiguous amino acids that is at least 92% identical over its entire length to an at least 150 contiguous amino acid sequence from SEQ ID NO:2.

In one embodiment, the isolated protein comprises a sequence of at least 50 contiguous amino acids, wherein the at least 50 contiguous amino acid sequence is at least 92% identical over its entire length to an at least 50 contiguous amino acid sequence from an amino acid sequence selected from the group consisting of SEQ ID NO:2 and further comprises at least one sequence feature selected from the group consisting of:

a. a cysteine residue at the position corresponding to position 27 of SEQ ID NO:2;
   b. an leucine residue at the position corresponding to position 29 of SEQ ID NO:2
   c. a serine residue at the position corresponding to position 30 of SEQ ID NO:2
   d. a tyrosine residue at the position corresponding to position 32 of SEQ ID NO:2
   e. a serine residue at the position corresponding to position 34 of SEQ ID NO:2
   f. a proline residue at the position corresponding to position 37 of SEQ ID NO:2;
   g. a leucine residue at the position corresponding to position 40 of SEQ ID NO:2;

h. an alanine residue at the position corresponding to position 42 of SEQ ID NO:2;
i. a lysine residue at the position corresponding to position 44 of SEQ ID NO:2;
j. an aspartic acid residue at the position corresponding to position 48 of SEQ ID NO:2;
k. a tyrosine residue at the position corresponding to position 50 of SEQ ID NO:2;
l. a glutamic acid residue at the position corresponding to position 51 of SEQ ID NO:2;
m. a cysteine residue at the position corresponding to position 62 of SEQ ID NO:2;
n. a cysteine residue at the position corresponding to position 76 of SEQ ID NO:2;
o. an alanine residue at the position corresponding to position 87 of SEQ ID NO:2;
p. a leucine residue at the position corresponding to position 111 of SEQ ID NO:2;
q. a leucine residue at the position corresponding to position 112 of SEQ ID NO:2;
r. an aspartic acid residue at the position corresponding to position 118 of SEQ ID NO:2;
s. an alanine residue at the position corresponding to position 120 of SEQ ID NO:2;
t. a cysteine residue at the position corresponding to position 122 of SEQ ID NO:2;
u. a cysteine residue at the position corresponding to position 152 of SEQ ID NO:2;
v. a valine residue at the position corresponding to position 157 of SEQ ID NO:2;
w. an asparagine residue at the position corresponding to position 160 of SEQ ID NO:2;
x. a leucine residue at the position corresponding to position 161 of SEQ ID NO:2;
y. an arginine residue at the position corresponding to position 163 of SEQ ID NO:2
z. a leucine residue at the position corresponding to position 165 of SEQ ID
aa. a threonine residue at the position corresponding to position 166 of SEQ ID NO:2;
bb. an alanine residue at the position corresponding to position 173 of SEQ ID NO:2; and
cc. a cysteine residue at the position corresponding to position 178 of SEQ ID NO:2.

In one embodiment, the isolated protein comprises an amino acid sequence at least 92% identical over its entire length to an amino acid sequence selected from the group consisting of SEQ ID NO:2, SEQ ID NO:5 and SEQ ID NO:8, wherein the isolated protein comprises at least one sequence feature selected from the group consisting of:
a. a cysteine residue at the position corresponding to position 27 of SEQ ID NO:2;
b. an leucine residue at the position corresponding to position 29 of SEQ ID NO:2
c. a serine residue at the position corresponding to position 30 of SEQ ID NO:2
d. a tyrosine residue at the position corresponding to position 32 of SEQ ID NO:2
e. a serine residue at the position corresponding to position 34 of SEQ ID NO:2
f. a proline residue at the position corresponding to position 37 of SEQ ID NO:2;
g. a leucine residue at the position corresponding to position 40 of SEQ ID NO:2;
h. an alanine residue at the position corresponding to position 42 of SEQ ID NO:2;
i. a lysine residue at the position corresponding to position 44 of SEQ ID NO:2;
j. an aspartic acid residue at the position corresponding to position 48 of SEQ ID NO:2;
k. a tyrosine residue at the position corresponding to position 50 of SEQ ID NO:2;
l. a leucine residue at the position corresponding to position 111 of SEQ ID NO:2;
m. a leucine residue at the position corresponding to position 112 of SEQ ID NO:2;
n. an aspartic acid residue at the position corresponding to position 118 of SEQ ID NO:2;
o. an alanine residue at the position corresponding to position 120 of SEQ ID NO:2;
p. a cysteine residue at the position corresponding to position 122 of SEQ ID
q. a cysteine residue at the position corresponding to position 152 of SEQ ID NO:2;
r. a valine residue at the position corresponding to position 157 of SEQ ID NO:2;
s. an asparagine residue at the position corresponding to position 160 of SEQ ID NO:2;
t. a leucine residue at the position corresponding to position 161 of SEQ ID NO:2;
u. an arginine residue at the position corresponding to position 163 of SEQ ID NO:2
v. a leucine residue at the position corresponding to position 165 of SEQ ID NO:2;
w. a threonine residue at the position corresponding to position 166 of SEQ ID NO:2;
x. an alanine residue at the position corresponding to position 173 of SEQ ID NO:2; and
y. a cysteine residue at the position corresponding to position 178 of SEQ ID NO:2.

In one embodiment, the isolated protein comprises an amino acid sequence at least 92% identical over its entire length to an SEQ ID NO:2, wherein the isolated protein comprises at least one sequence feature selected from the group consisting of:
a. an cysteine residue at the position corresponding to position 27 of SEQ ID NO:2;
b. an leucine residue at the position corresponding to position 29 of SEQ ID NO:2
c. a serine residue at the position corresponding to position 30 of SEQ ID NO:2
d. a tyrosine residue at the position corresponding to position 32 of SEQ ID NO:2
e. a serine residue at the position corresponding to position 34 of SEQ ID NO:2
f. a proline residue at the position corresponding to position 37 of SEQ ID NO:2;
g. a leucine residue at the position corresponding to position 40 of SEQ ID NO:2;
h. an alanine residue at the position corresponding to position 42 of SEQ ID NO:2;
i. a lysine residue at the position corresponding to position 44 of SEQ ID NO:2;
j. an aspartic acid residue at the position corresponding to position 48 of SEQ ID NO:2;
k. a tyrosine residue at the position corresponding to position 50 of SEQ ID
l. a glutamic acid residue at the position corresponding to position 51 of SEQ ID NO:2;
m. a cysteine residue at the position corresponding to position 62 of SEQ ID NO:2;
n. a cysteine residue at the position corresponding to position 76 of SEQ ID NO:2;

o. an alanine residue at the position corresponding to position 87 of SEQ ID NO:2;
p. a leucine residue at the position corresponding to position 111 of SEQ ID NO:2;
q. a leucine residue at the position corresponding to position 112 of SEQ ID NO:2;
r. an aspartic acid residue at the position corresponding to position 118 of SEQ ID NO:2;
s. an alanine residue at the position corresponding to position 120 of SEQ ID NO:2;
t. a cysteine residue at the position corresponding to position 122 of SEQ ID NO:2;
u. a cysteine residue at the position corresponding to position 152 of SEQ ID NO:2;
v. a valine residue at the position corresponding to position 157 of SEQ ID NO:2;
w. an asparagine residue at the position corresponding to position 160 of SEQ ID NO:2;
x. a leucine residue at the position corresponding to position 161 of SEQ ID NO:2;
y. an arginine residue at the position corresponding to position 163 of SEQ ID NO:2
z. a leucine residue at the position corresponding to position 165 of SEQ ID NO:2;
aa. a threonine residue at the position corresponding to position 166 of SEQ ID NO:2;
bb. an alanine residue at the position corresponding to position 173 of SEQ ID NO:2; and
cc. a cysteine residue at the position corresponding to position 178 of SEQ ID NO:2.

In one embodiment, the protein possesses at least one activity selected from the group consisting of: eliciting an antibody that selectively binds a protein consisting of SEQ ID NO:2, selectively binding an antibody generated against a protein consisting of SEQ ID NO:2, selectively binding a compound that binds to a protein consisting of SEQ ID NO:2, activating expression of the JAK/STAT pathway, and inducing expression of at least one ISG listed in FIG. 15.

In one embodiment, the invention provides an isolated nucleic acid molecule comprising a nucleic acid sequence selected from a nucleic acid sequence encoding an isolated protein of the present invention, and a nucleic acid sequence fully complementary thereto. In certain embodiments the nucleic acid molecule comprises a nucleic acid sequence selected from the group consisting of SEQ ID NO:1, SEQ ID NO:3, SEQ ID NO:4, SEQ ID NO:6, SEQ ID NO:7, and SEQ ID NO:9. One embodiment of the invention provides a plasmid containing an isolated nucleic acid molecule of the invention. Similarly, another embodiment of the invention provides a virus containing an isolated nucleic acid molecule of the invention.

One embodiment of the invention is an isolated antibody that selectively binds to an IFNL4 protein of the invention. Another embodiment of the invention provides an isolated antibody that inhibits the binding of an antibody that selectively binds to an IFNL4 protein of the invention.

One embodiment of the invention is a method for predicting the likelihood of an individual to spontaneously clear an HCV infection, by obtaining a biological sample from the individual; and analyzing the sample to determine the presence or absence of an IFNL4 mRNA or protein of the present invention. In this method, the absence of IFNL4 mRNA or IFNL4 protein indicates an increased likelihood of the individual spontaneously clearing an HCV infection. In this method, the presence of IFNL4 mRNA or protein indicates a decreased likelihood of the individual spontaneously clearing an HCV infection.

One embodiment of the invention is a method for predicting the likelihood that an individual will respond to a treatment for HCV infection by obtaining a biological sample from the individual and analyzing the sample to determine the presence or absence of IFNL4 mRNA or IFNL4 protein of the present invention. In this method, the absence of IFNL4 mRNA or IFNL4 protein of the present invention indicates an increased likelihood the individual will respond to treatment for an HCV infection. Alternatively, in this method the presence of IFNL4 mRNA or IFNL4 protein indicates a decreased likelihood the individual will respond to treatment for an HCV infection. In one embodiment, the presence of IFNL4 protein indicates the individual is predicted to be unable to respond to treatment for an HCV infection.

One embodiment of the invention is a method for predicting the likelihood of an individual to spontaneously clear an HCV infection by obtaining a biological sample from an individual and determining the level of IFNL4 mRNA or IFNL4 protein present in the sample, if any. In this embodiment the level of IFNL4 mRNA or IFNL4 protein present in the sample indicates the likelihood the individual will spontaneously clear an HCV infection. In this method, a level of IFNL4 mRNA or IFNL4 in the sample less than the level of IFNL4 mRNA or IFNL4 protein present in a subject known to be able to clear an HCV infection indicates the individual is predicted to be able to clear an HCV infection. In this method, a level of IFNL4 mRNA or IFNL4 in the sample greater than the level of IFNL4 mRNA or IFNL4 protein present in a subject known to be unable to clear an HCV infection indicates the individual is predicted to be unable to clear an HCV infection.

One embodiment of the invention is a method for treating a patient suffering from a chronic hepatitis C virus infection by obtaining a biological sample from the individual, analyzing the sample to determine the presence, absence or level of IFNL4 mRNA or IFNL4 protein present in the sample and determining whether or not to administer treatment based on the presence, absence or amount of IFNL4 mRNA or IFNL4 protein present in the sample.

One embodiment of the invention is a kit useful for determining the presence, absence or level of IFNL4 protein in a sample. The kit comprises an antibody that specifically recognizes an IFNL4 protein of the invention. In one embodiment, the kit comprises instructions for determining the ability of an individual to spontaneously clear an HCV infection. In one embodiment, the kit comprises instructions for determining the ability of an individual to respond to treatment for an HCV infection.

In one embodiment, the present invention provides a variant IFNL4 polypeptide having at least 90%, at least 95%, at least 97%, at least 98% or at least 99% sequence identity to a protein selected from the group consisting of IFNL4-p179, p131 and p107 (SEQ ID NO:2, SEQ ID NO:5 and SEQ ID NO:8) wherein the variant polypeptide has at least one amino acid substitution, using the numbering system of SEQ ID NO:2, selected from the group consisting of A10P, A11P, L13M, V15F, C17Y, V19M, I20V, A21P, R26G, L28M, L35M, L40M, G116R, A121P, A126P, P128A, G129A, S130P, R132G, P135A, K139R, R140G, K143E, R146K, S149P, P150A, K154E, A155P, S156G, V158I, F159V, L162M, L164M, and L169F.

In one embodiment, the present invention provides a variant IFNL4 polypeptide having at least 90%, at least 95%, at least 97%, at least 98% or at least 99% sequence identity to a protein selected from the group consisting of IFNL4 p179, p131 and p107 (SEQ ID NO:2, SEQ ID NO:5 and SEQ ID NO:8) wherein the variant polypeptide has at least one amino acid substitution, using the numbering system of SEQ ID NO:2, selected from selected form the group consisting of A10P, A11P, L13M, V15F, C17Y, V19M, I20V, A21P, R26G, L28M, L35M, L40M, E52K, L55M, W57R, R60P, N61H, S63P, F64V, R65G, D69H, P70S, P71T, R72G, G116R, A121P, A126P, P128A, G129A, S130P, R132G, P135A, K139R, R140G, K143E, R146K, S149P, P150A, K154E, A155P, S156G, V158I, F159V, L162M, L164M, and L169F.

In one embodiment, the present invention provides a variant IFNL4 polypeptide having at least 90%, at least 95%, at least 97%, at least 98% or at least 99% sequence identity to a protein selected from the group consisting of IFNL4-p179, p131 and p107 (SEQ ID NO:2, SEQ ID NO:5 and SEQ ID NO:8) wherein the variant polypeptide has at least one amino acid substitution, using the numbering system of SEQ ID NO:2, selected from the group consisting of A10P, A11P, L13M, V15F, C17Y, V19M, I20V, A21P, R26G, L28M, L35M, L40M, E52K, L55M, W57R, R60P, N61H, S63P, F64V, R65G, D69H, P70S, P71T, R72G, R78G, V92M, L93I, L101M, L102F, G116R, A121P, A126P, P128A, G129A, S130P, R132G, P135A, K139R, R140G, K143E, R146K, S149P, P150A, K154E, A155P, S156G, V158I, F159V, L162M, L164M, and L169F.

BRIEF DESCRIPTION OF DRAWINGS

FIG. 4. Information on transcripts identified within the IFNL4 region and submitted to NCBI GenBank.

FIG. 5. mRNA expression of full-length IFNL4 isoforms in human hepatocyte samples homozygous for ΔG or TT alleles of a genetic variant ss469415590 and activated with PolyI:C for 0, 2, 4 and 24 h. The deletion (ΔG) allele introduces a frame-shift that creates proteins of 179, 131 or 107 aa. The insertion (TT) allele creates several prematurely terminated transcripts that are likely to be degraded by nonsense-mediated decay. The primers detect the full-length amplicon of IFNL4, including the start and stop codons. Also shown is expression of IFNL3 (IL28B) and IFNL1 (IL29) transcripts, which are induced by PolyI:C treatment in samples with both genotypes. Expression of endogenous control, PPIA, in the same samples is used as a loading control. All samples were treated with DNAse I and the signal should be specific for RNA expression only.

FIG. 6 Comparisons between IFNL4-p179 protein and selected members of the class-2 cytokine family.

Confocal imaging of endogenously expressed IFNL4 in primary human hepatocytes (PHH) from an individual heterozygous for ss469415590, the IFNL4 expression is induced by treatment with PolyI:C or in-vitro infection with HCV.

Figure 10:
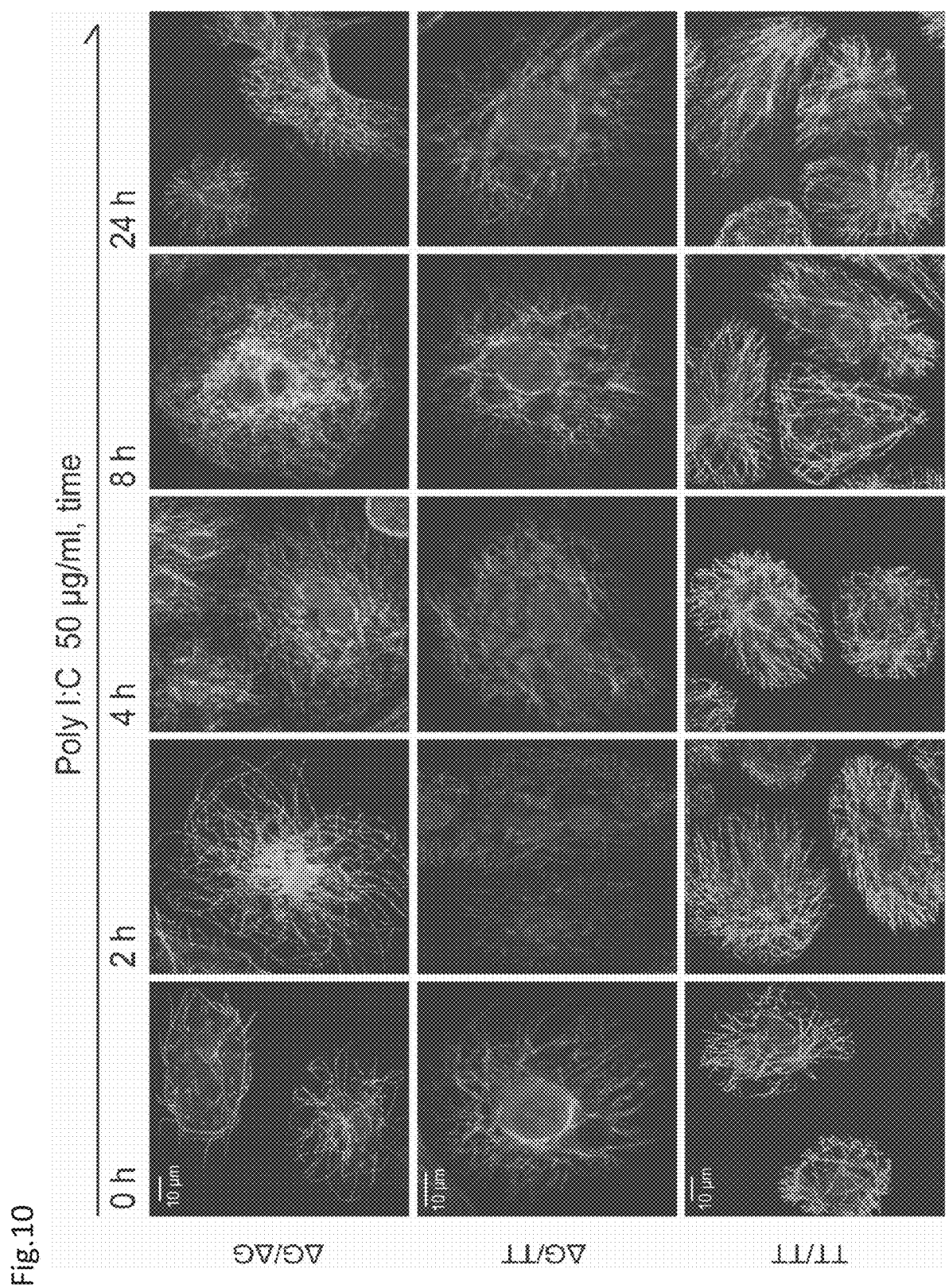

FIG. 10. Confocal imaging in PHHs from carriers of different genotypes of ss469415590 (TT/TT, TT/ΔG or ΔG/ΔG) treated with 50 µg/ml of polyI:C for 0, 2, 4, 8 or 24 h. Red, IFNL4; green, cytoskeleton (α-tubulin), blue, nuclei. Intracellular IFNL4 expression is detected only in the PHH from carriers of risk genotypes (TT/AG or ΔG/ΔG).

Figure 11A:
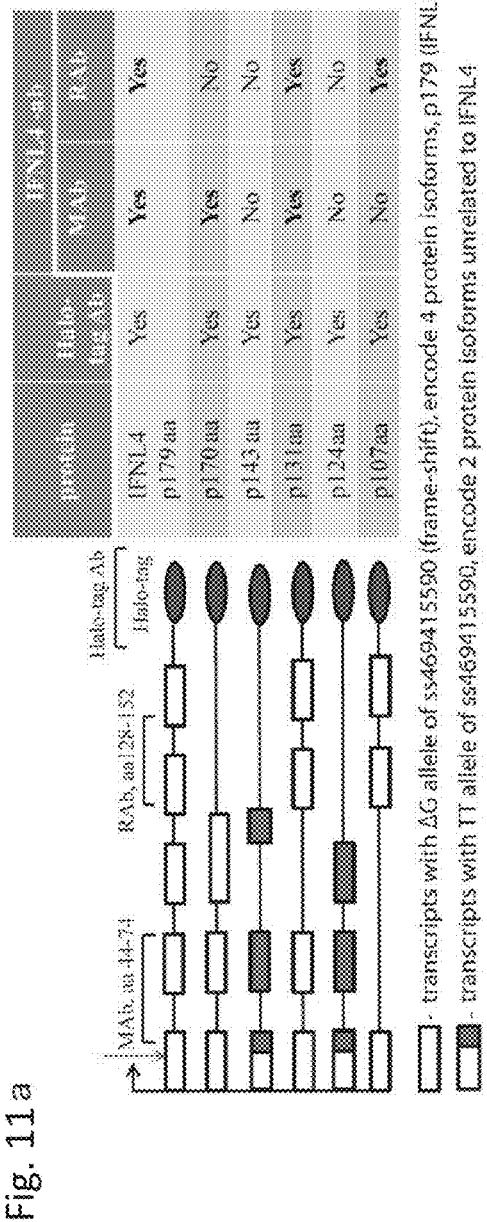
Figure 11B:
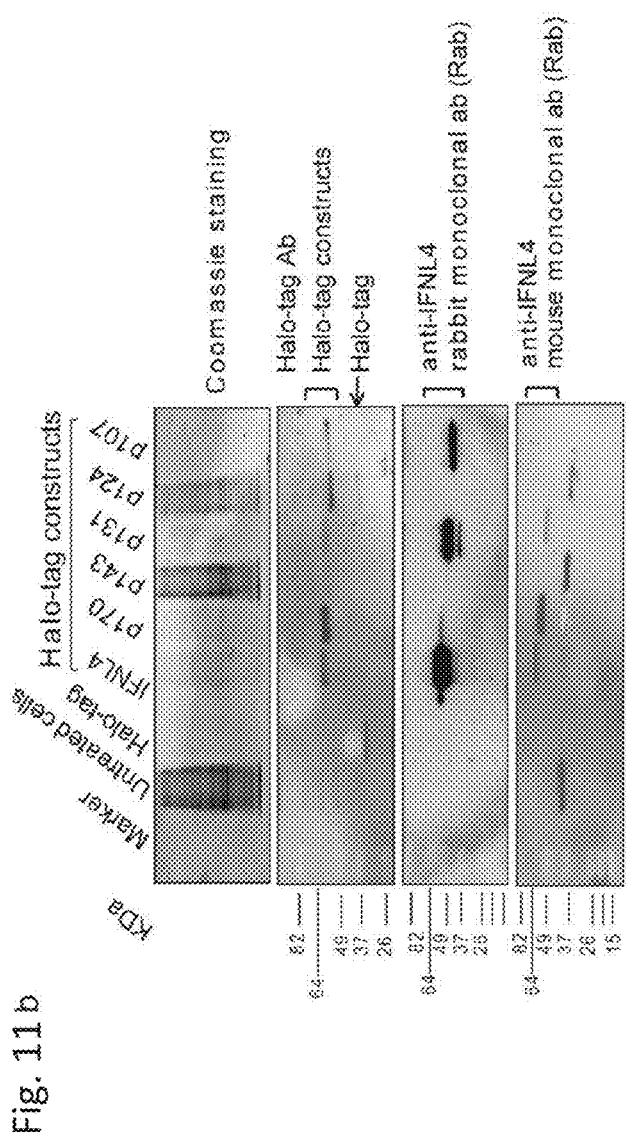

FIGS. 11a & 11b. Overview of the mouse and rabbit anti-IFNL4 monoclonal antibodies: location within protein and detection pattern of different protein isoforms after transient transfection of corresponding expression constructs in HepG2 cells.

Figure 12:
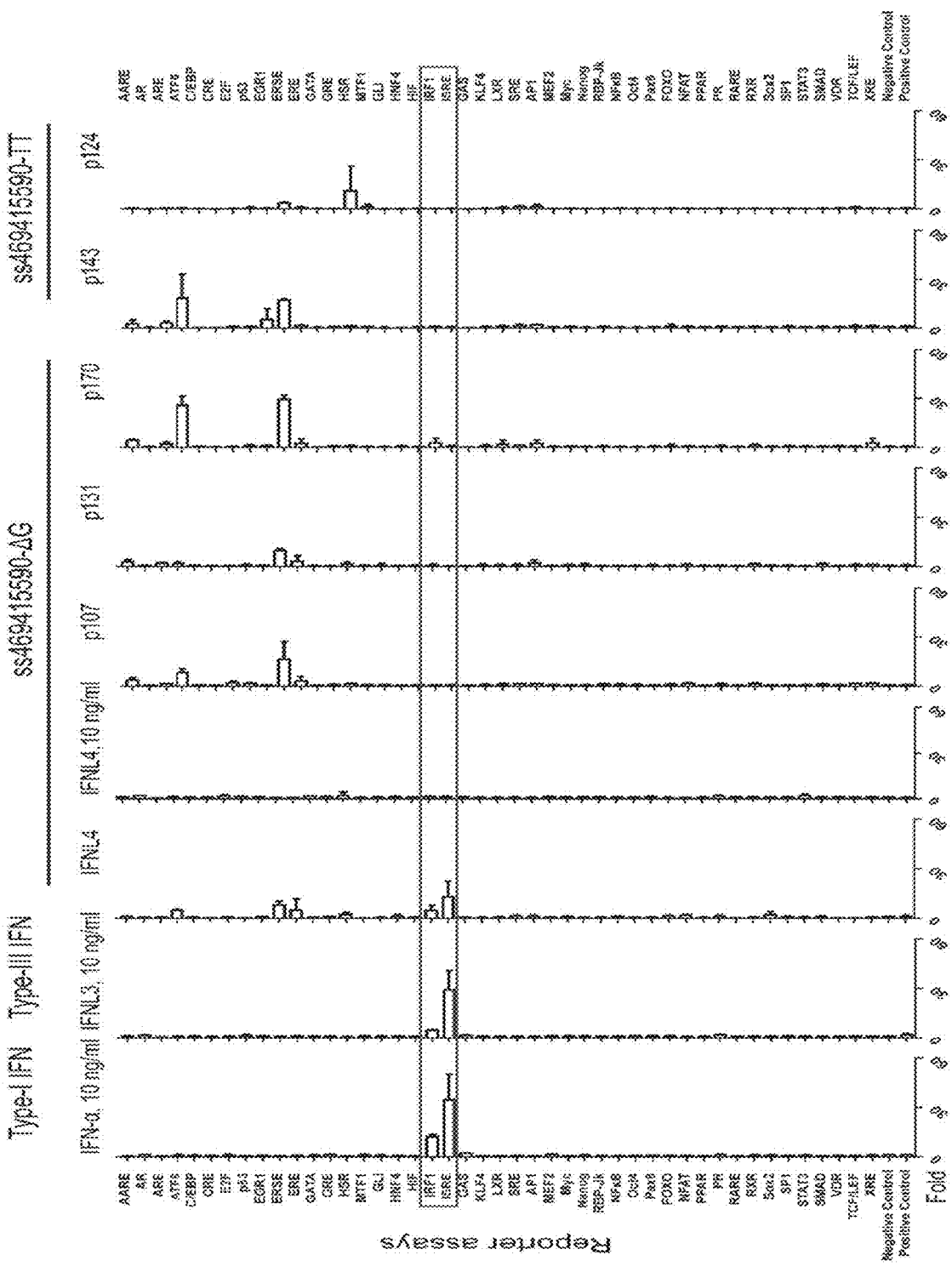

FIG. 12. Pathway Finder Analysis using luciferase reporter constructs representing 45 human signaling pathways in HepG2 cells. The cells were transiently transfected with expression constructs or an empty vector or treated with 10 ng/ml recombinant purified IFN-α, IFNL3, IFNL4 or with PBS. All results represent the mean values of two independent biological transfection and/or treatment replicates. Error bars, s.d. The rectangle marks reporters (ISRE-Luc and IRF3-Luc) significantly induced by treatment with IFN-α, IFNL3 and transient transfection with IFNL4 construct.

Figure 13:
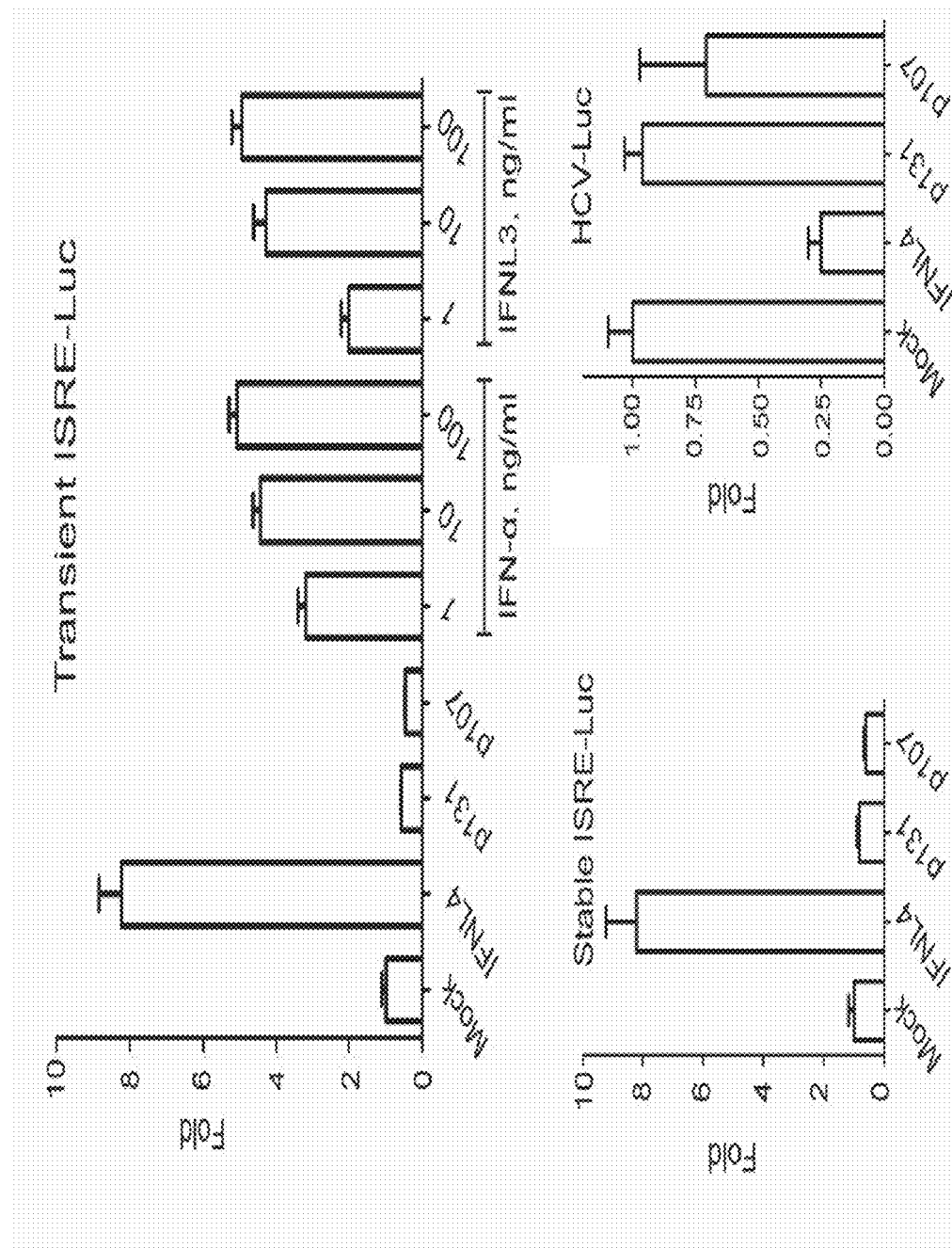

FIG. 13. Luciferase activity after transfection with construct expressing IFNL4, p131 or p107 and treatment with recombinant purified IFN-α or IFNL3 in the HepG2 cell line transiently cotransfected with the ISRE-Luc reporter. The results are normalized to the activity seen after transfection with empty vector (mock) and represent the mean values of eight biological replicates. Luciferase activity after transient transfection with construct expressing IFNL4, p131 or p107 in the HepG2 cell line stably expressing the ISRE-Luc reporter. The results are normalized to the activity seen after transfection with empty vector (mock) and represent the mean values of 11 biological replicates. Test for antiviral effects of the expression constructs for IFNL4, p131 and p107 transiently transfected into Huh7-Lunet cells stably expressing a subgenomic luciferase-expressing HCV replicon (HCV-Luc) compared to the effect seen after transfection with empty vector (mock). Results represent the mean values of four biological replicates. Error bars, s.e.m.

Figure 14:
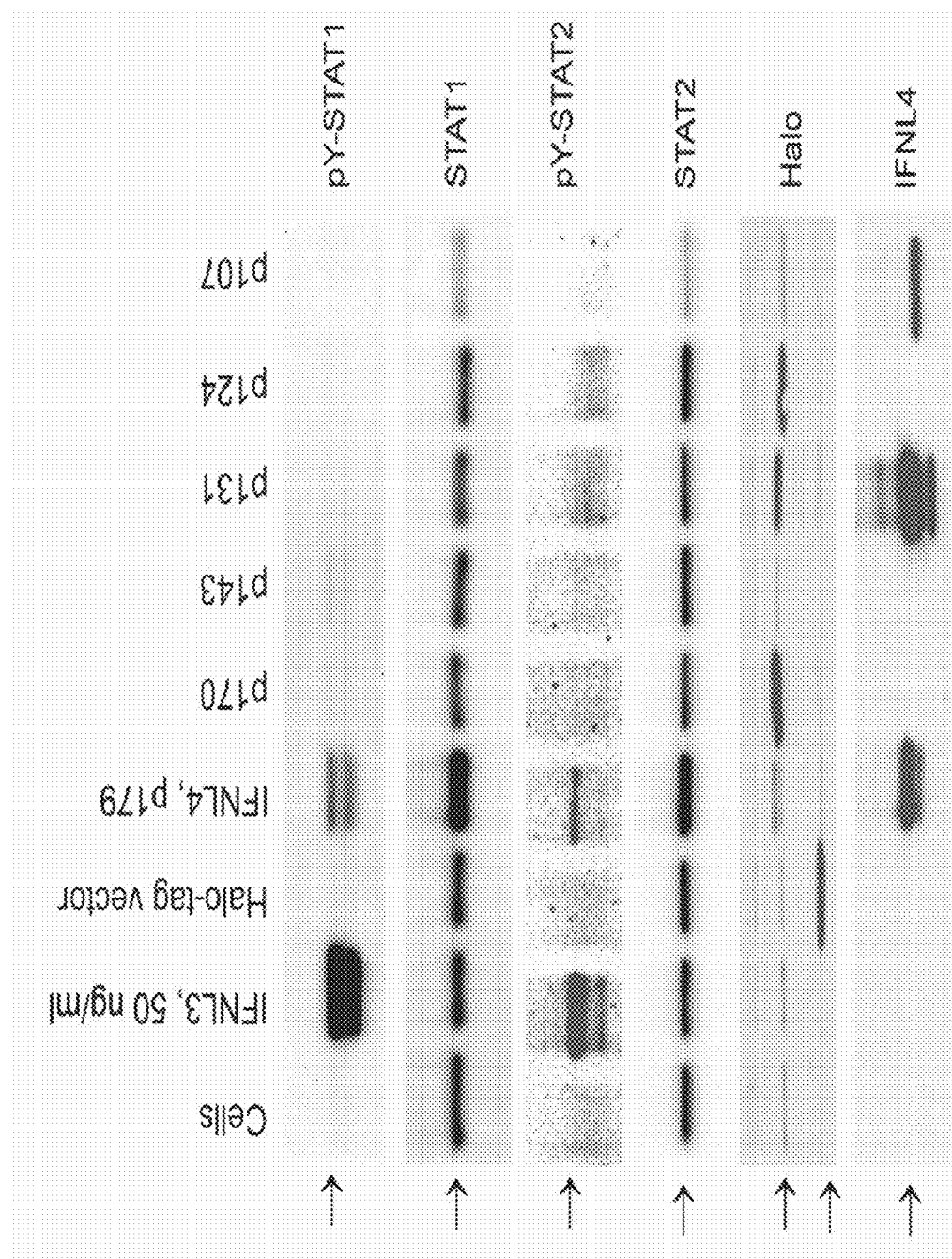

FIG. 14. Protein blot analysis of STAT1 phosphorylated at Tyr701 (pSTAT1) and STAT2 phosphorylated at Tyr689 (pSTAT2) in HepG2 cells transiently transfected with constructs expressing the six protein isoforms, including IFNL4-p179-Halo. All constructs are fused with the Halo tag and produce proteins detectable with an antibody for the Halo-tag; the rabbit monoclonal antibody to IFNL4 recognizes p179 as well as the nonfunctional isoforms p131 and p107.

Figure 15:
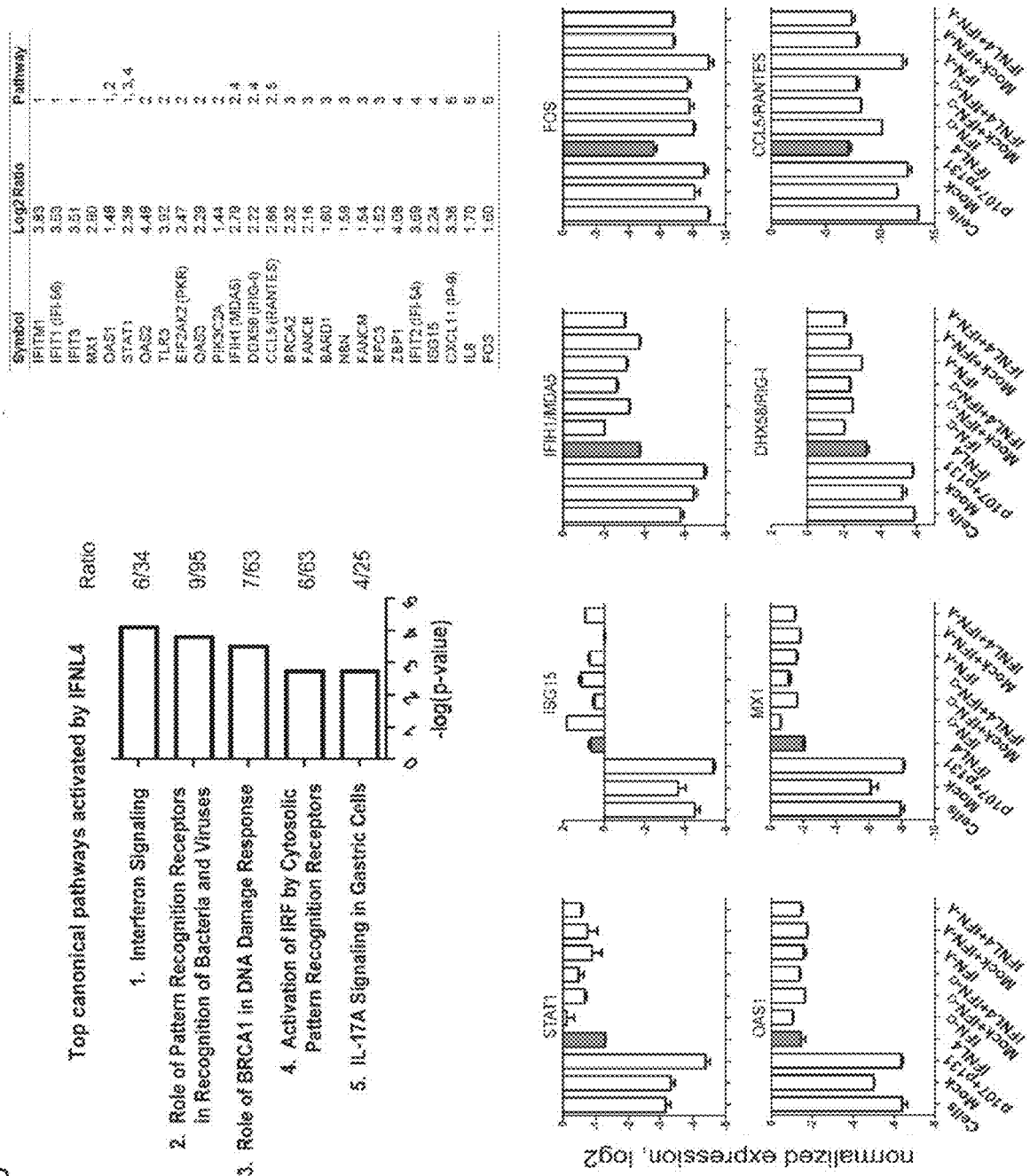

FIG. 15. Analysis of top canonical pathways and individual transcripts activated by transient overexpression of IFNL4 construct in HepG2 cells, based on global RNA-seq analysis.
Expression of selected ISGs in HepG2 cells in different conditions was analyzed in cells untreated, or transfected with empty vector (mock); IFNL4-p179, IFNL4-p131 or IFNL4-p107; or treated with 10 ng/ml of IFN-α or IFNL3 (IL28B) alone or after transfection with mock or IFNL4-p179. Expression of ISGs was analyzed by qRT-PCR with specific assays and normalized to expression of four endogenous controls measured in the same samples. The data is presented on log 2 scale—less negative values indicate higher expression. Error bars indicate mean values with 95% confidence intervals.

Figure 16:
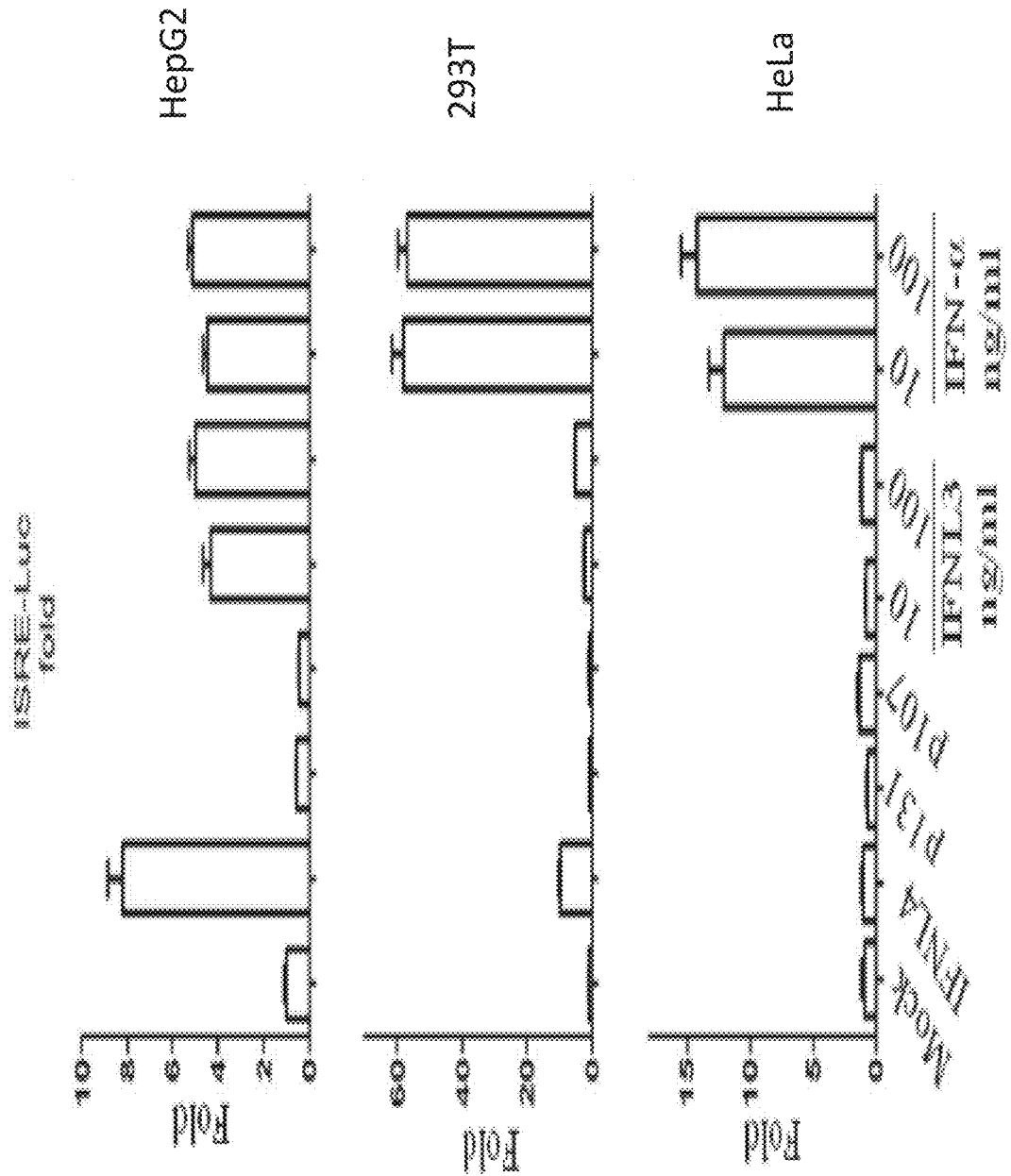

FIG. 16. Test for activation of the JAK/STAT pathway using ISRE-Luc Cignal reporter transiently transfected into HepG2, 293T and HeLa cells. Activation by transiently co-transfected IFNL4-p179, p107 and p131 expression constructs or by recombinant purified IFN-α and IFNL3 (IL28B) proteins at indicated concentrations. Fold response is for comparison to mock-control (transfection with empty vector). Error bars indicate mean values of 4-8 independent biological replicates with 95% confidence intervals.

Figure 17:
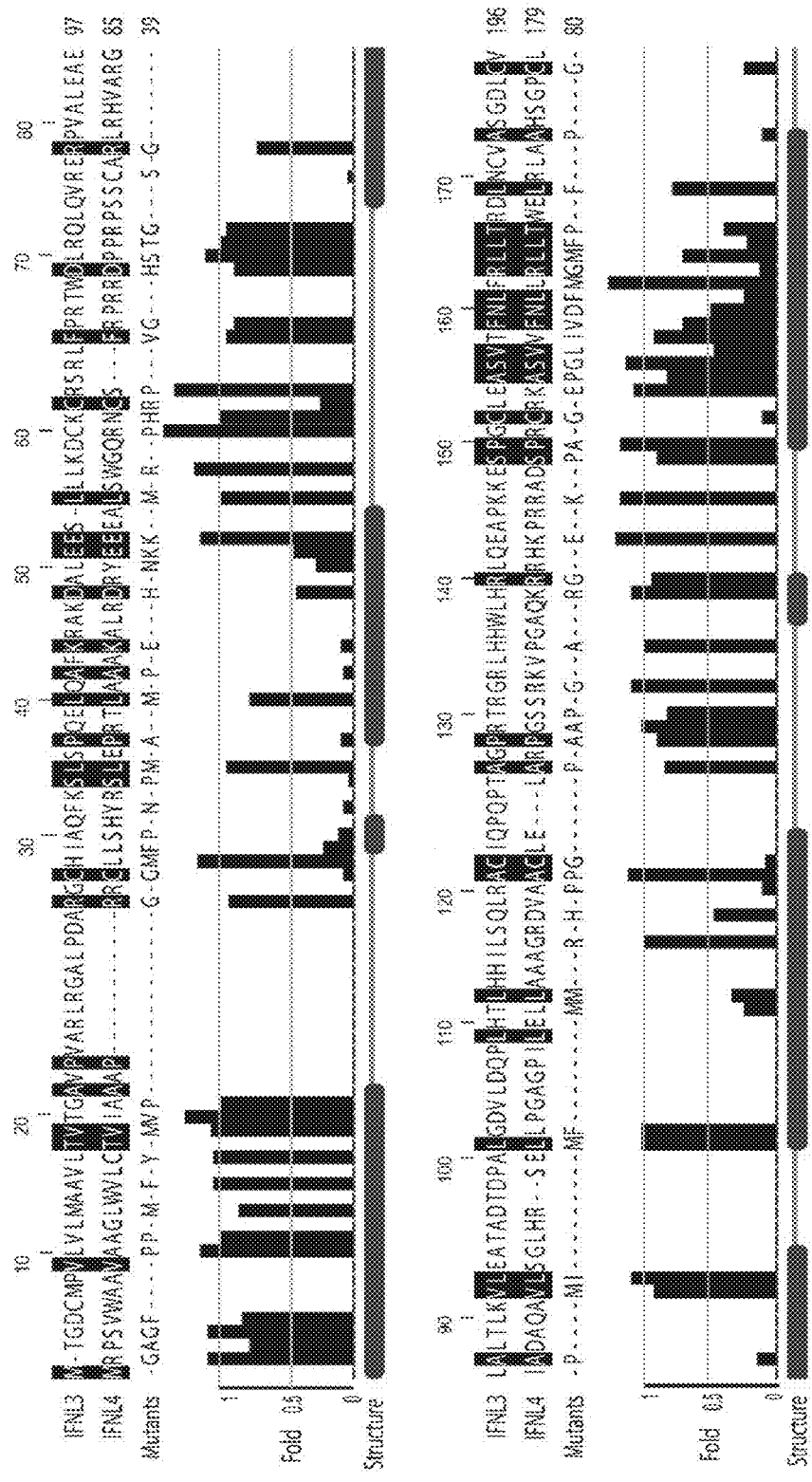

FIG. 17. Analysis of 83 site-directed mutants of IFNL4. Protein sequence of IFNL4 is aligned with IFNL3 and conserved amino acids are shaded; IFNL4 single-point mutations at specific positions are marked by amino acid numbers (above) and types of changes (below) the sequence. Biological activity is defined as the ability to activate JAK/STAT pathway measured as an induction of a transiently transfected ISRE-Luc Cignal reporter construct in HepG2 cells, with 4 biological replicates for each of the constructs. Results for all mutants are normalized to activity of the WT-IFNL4.

Figure 18:
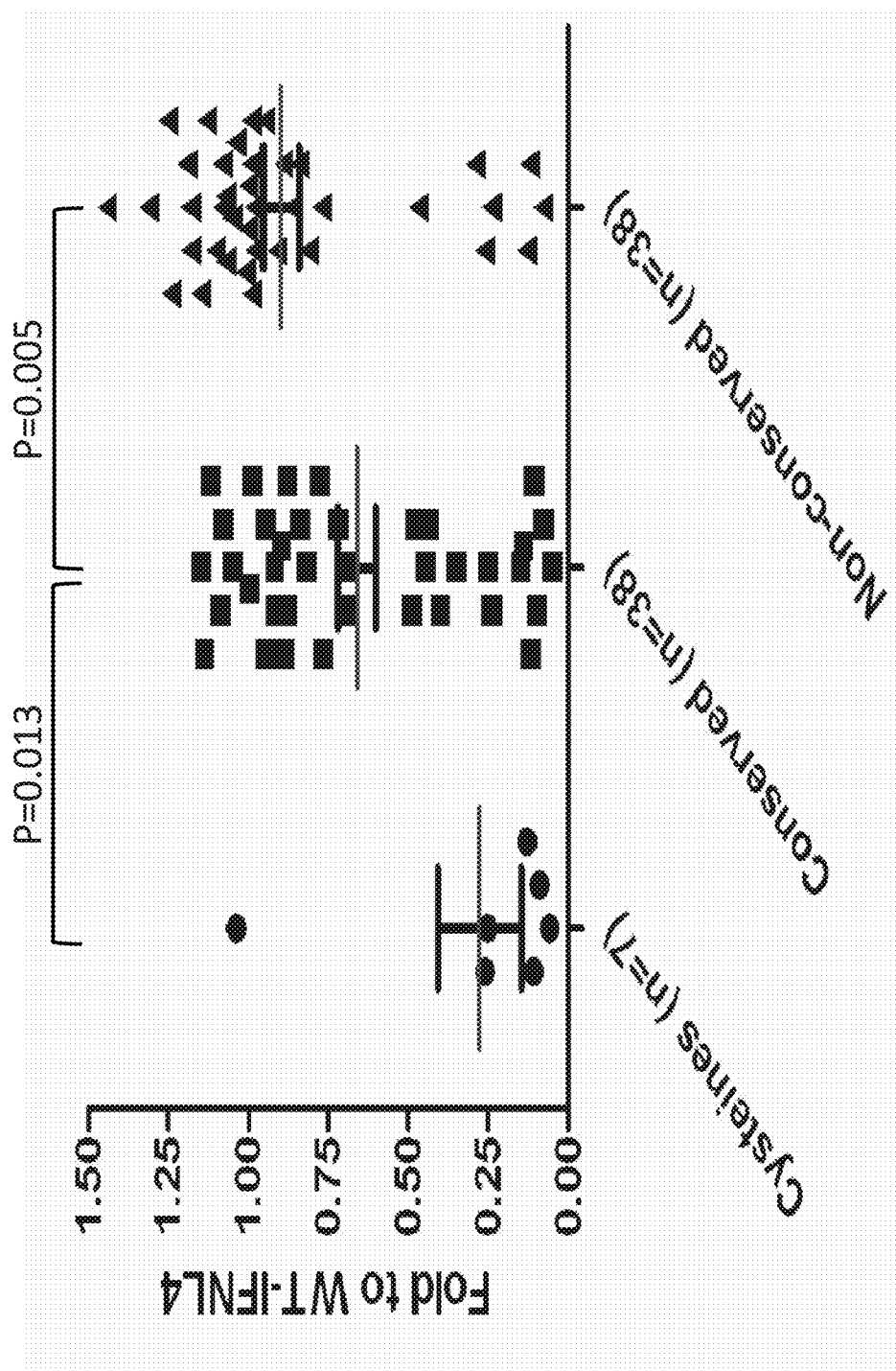

FIG. 18. Biological activity of 83 IFNL4 mutants in specific categories—cysteines residues (n=7) and non-cysteine residues conserved (n=38) or non-conserved (n=38) between IFNL3 and IFNL4. Mutations of any of the 6 non-polymorphic cysteines eliminate the activity of IFNL4. The exception is for a natural genetic variant Cys17Tyr which did not affect the ability of IFNL4 to activate ISRE-Luc reporter. Significantly higher (p=0.005 for a two-sided non-paired T-test) proportion of residues conserved between IFNL3 and IFNL4 suggests these residues are critical for retaining biological activity of IFNL4. Seven non-conserved IFNL4-specific residues were found of importance for biological activity for IFNL4.

FIG. 19. Amino acid changes caused by genetic variants within IFNL4 gene. Each of the amino acid changes belongs to a specific haplotype which carries the ΔG allele of the ss460415590 variant, thus, these amino acid changes only exist when IFNL4 protein is produced. No amino acid changes occur on haplotypes with the TT allele of the ss460415590, when IFNL4 is not produced.

Figure 20:
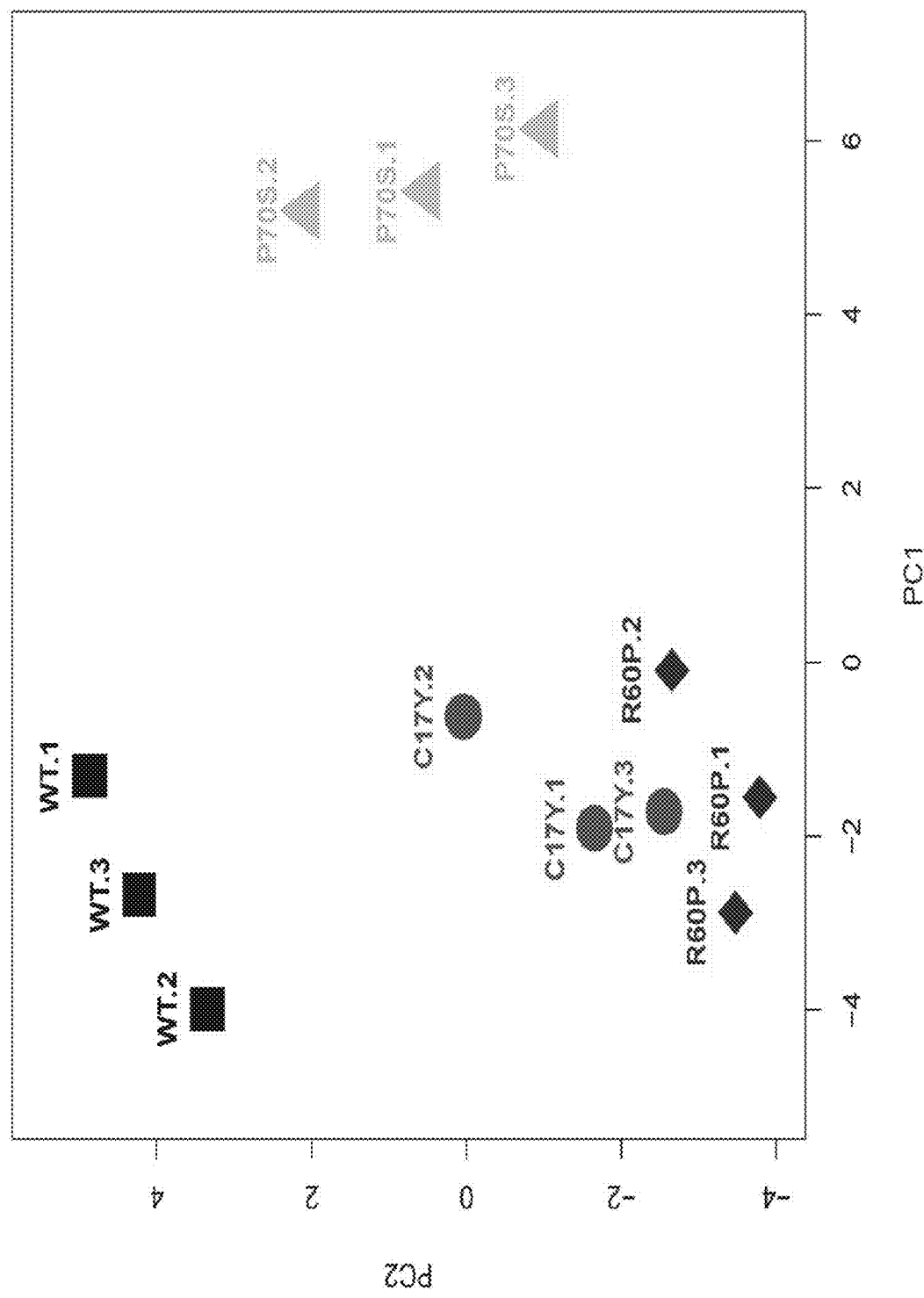

FIG. 20. Principal components analysis (PCA) based on expression of 33 transcripts involved in antiviral response and measured by qRT-PCR in HepG2 transiently transfected with specific allelic protein constructs (WT-IFNL4, Cys17Tyr, Arg60Pro and Pro70Ser), in three biological replicates. The PCA plot shows that Pro70Ser mutant differs from both the WT-IFNL4 protein and the group of Cys17Tyr and Arg60Pro mutants which cluster close to each other.

Figure 21:
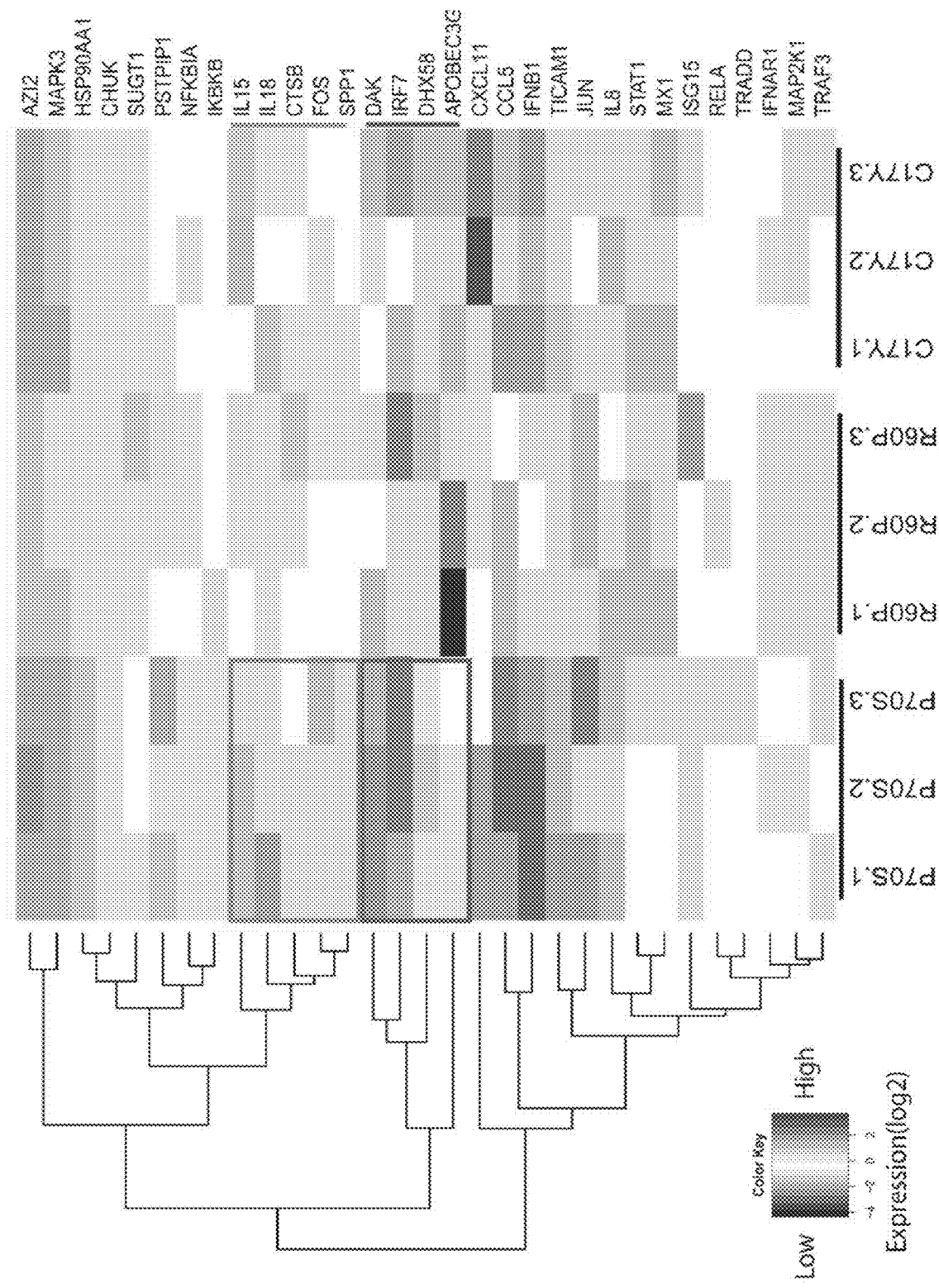

FIG. 21. Heatmap plot for transcripts with expression significantly affected by transient expression of IFNL4 allelic protein constructs (WT-IFNL4, Cys17Tyr, Arg60Pro and Pro70Ser) in HepG2 cells, based on results of experiment presented on FIG. 20. Mutants Cys17Tyr and Arg60Pro show similar effects on these transcripts, while Pro70Ser showed most difference with WT-IFNL4, causing lower expression of IL15, IL18, CTSB, FOS and SPP1 transcripts compared to cells transfected with WT-IFNL4, and higher expression of DAK, IRF7, DHX58 and APOBEC3G transcripts compared to cells transfected with WT-IFNL4. Color chart corresponds to log 2 scale expression changes caused by mutants compared to WT-IFNL4.

DESCRIPTION OF EMBODIMENTS

The present invention generally relates to a novel interferon gene referred to as IFNL4 and corresponding mRNA and protein generated in individuals that carry at least one deletion (ΔG) allele of the ss460415590 genetic variant. It also relates to methods of using IFNL4 mRNA or protein to determine the probability that an individual will spontaneously clear an HCV infection, or will respond to therapeutic treatment of an HCV infection. More specifically, the present invention relates to the discovery that the amount of IFNL4 mRNA or IFNL4 protein produced by an individual correlates with the probability that the individual will spontaneously clear an HCV infection, or will respond to treatment for an HCV infection. The present invention also relates to using IFNL4 protein to identify compounds that can be used to treat an individual with an HCV infection.

The present invention is an extension of the inventor's previous work, described in detail in U.S. Provisional Application No. 61/543,620, now International Application No. PCT/US12/59048, filed Oct. 5, 2012, which is incorporated herein by reference in its entirety. In their previous work, the inventors discovered a novel compound polymorphism referred to as ss469415590 (NCBI reference number NC_000019.9: [g.39739154delT;g.39739155T>G]). The ss469415590 polymorphism consists of two nucleotide variations that occur at positions 39,739,154 and 39,739,155 on human chromosome 19, the coordinates being based on the February 2009 human genome reference (GRch37/hg19). More specifically, the ss469415590 polymorphism consists of a single base deletion polymorphism (T/Δ) and a single base substitution polymorphism (T/G), which are in complete linkage disequilibrium ($r^2=1.0$). The inventors have also discovered that, following treatment with PolyI:C, novel mRNA transcripts are produced from this region (FIG.

Figure 2:
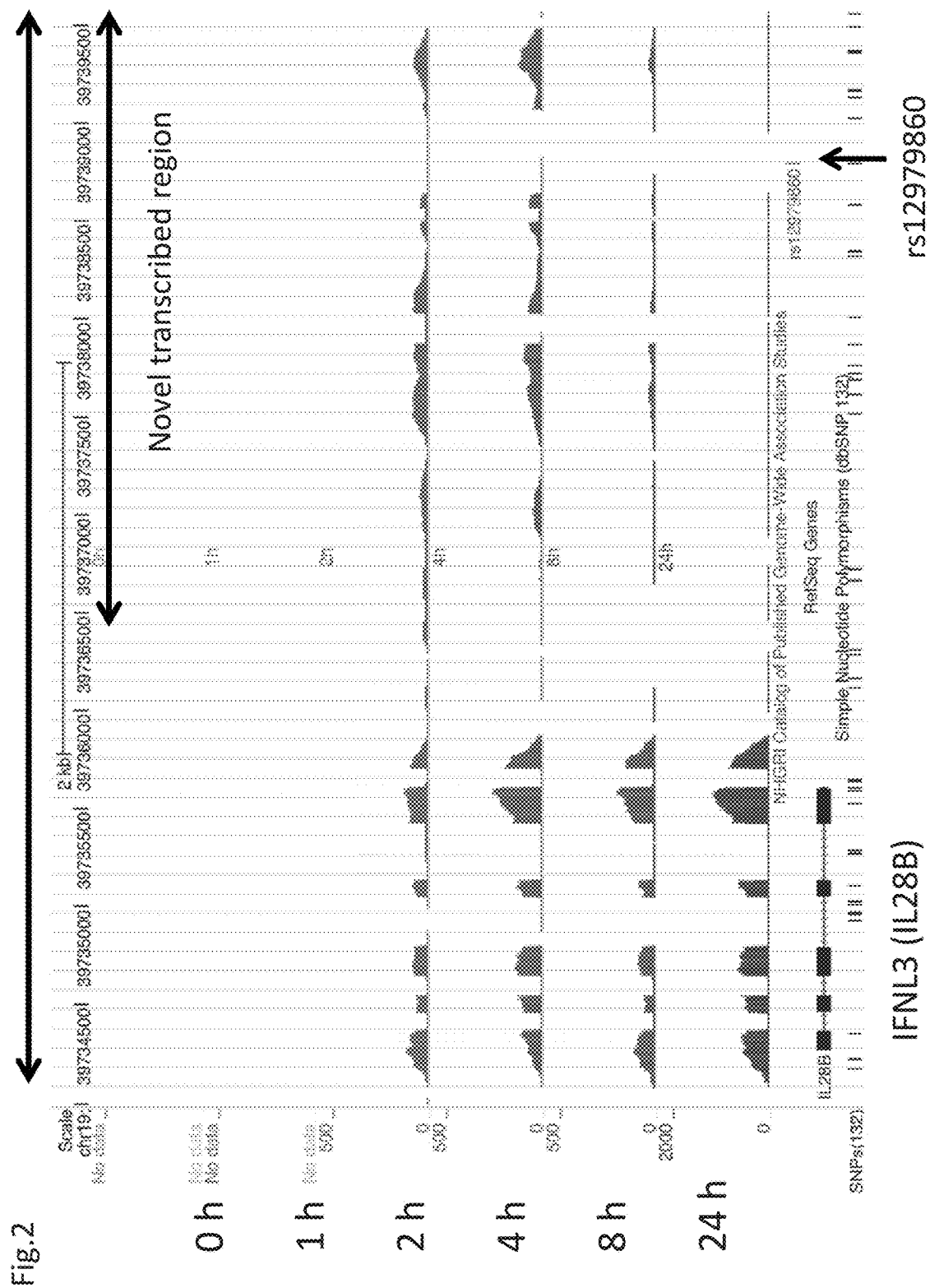
FIG. 2. Identification by RNA-seq of a novel IFNL4 gene encoding interferon-λ4 protein upstream of IFNL3 (IL28B) gene. The RNA-seq shows time-dependent activation of IFNL3 (IL28B) and a novel transcribed region in primary human hepatocytes treated with PolyI:C.
Figure 3:
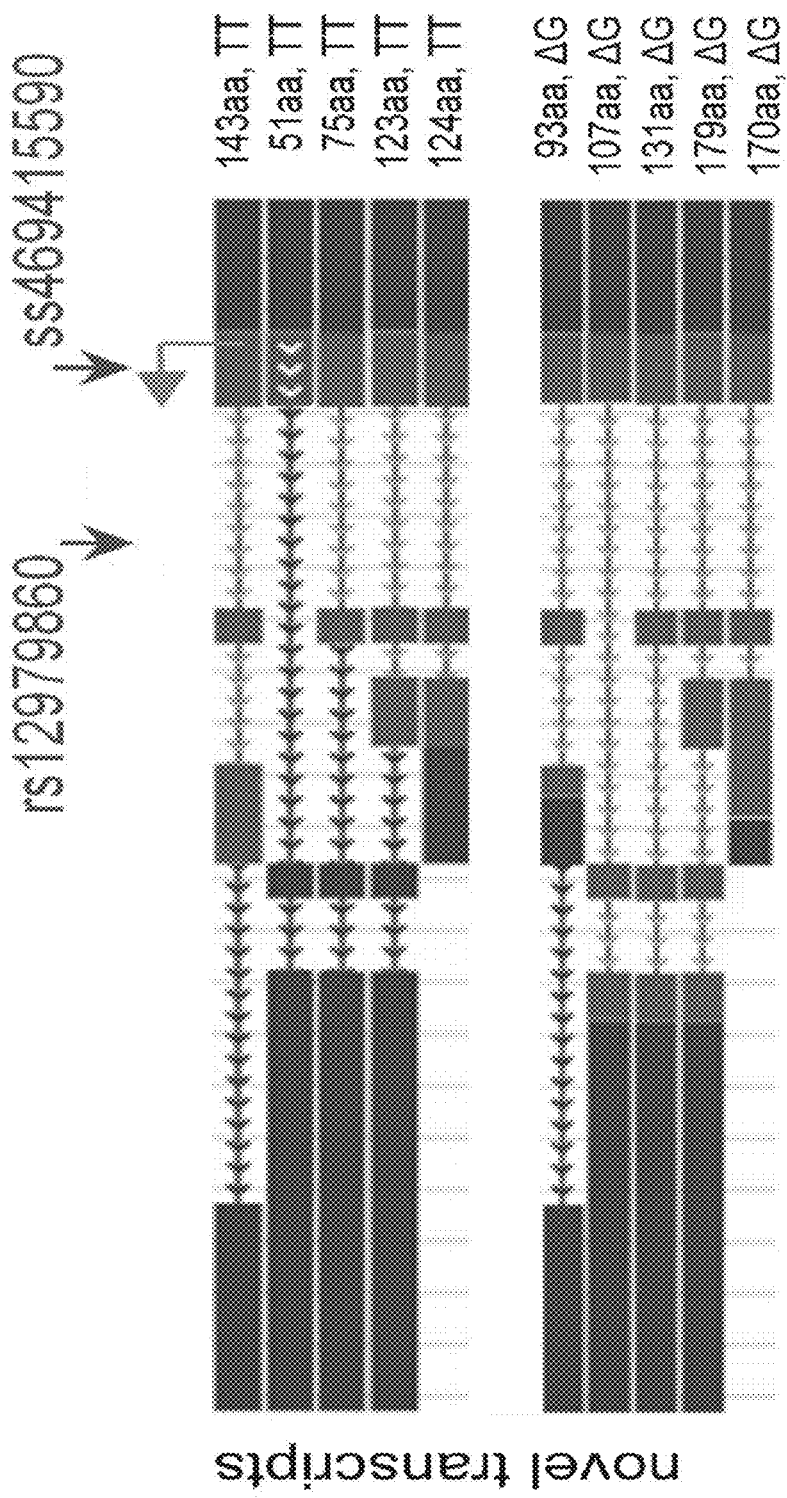
FIG. 3. Splicing architecture of the ten novel transcripts (NCBI accession numbers are presented in FIG. 4. The GWAS marker rs12979860 is located within intron 1, and a novel marker, ss469415590, with TT or ΔG alleles is located within exon 1 and is common to all transcripts. Translation start site is marked by an arrow; ORFs are shaded in blue; aa, amino acids. The IFNL4-specific protein-coding frame is created by a ΔG deletion allele of ss469415590 within the first exon of IFNL4 mRNA transcripts. The IFNL4 protein isoforms of 107, 131 or 179 aa are created by transcripts with 3, 4 or 5 exons.
Figure 7:
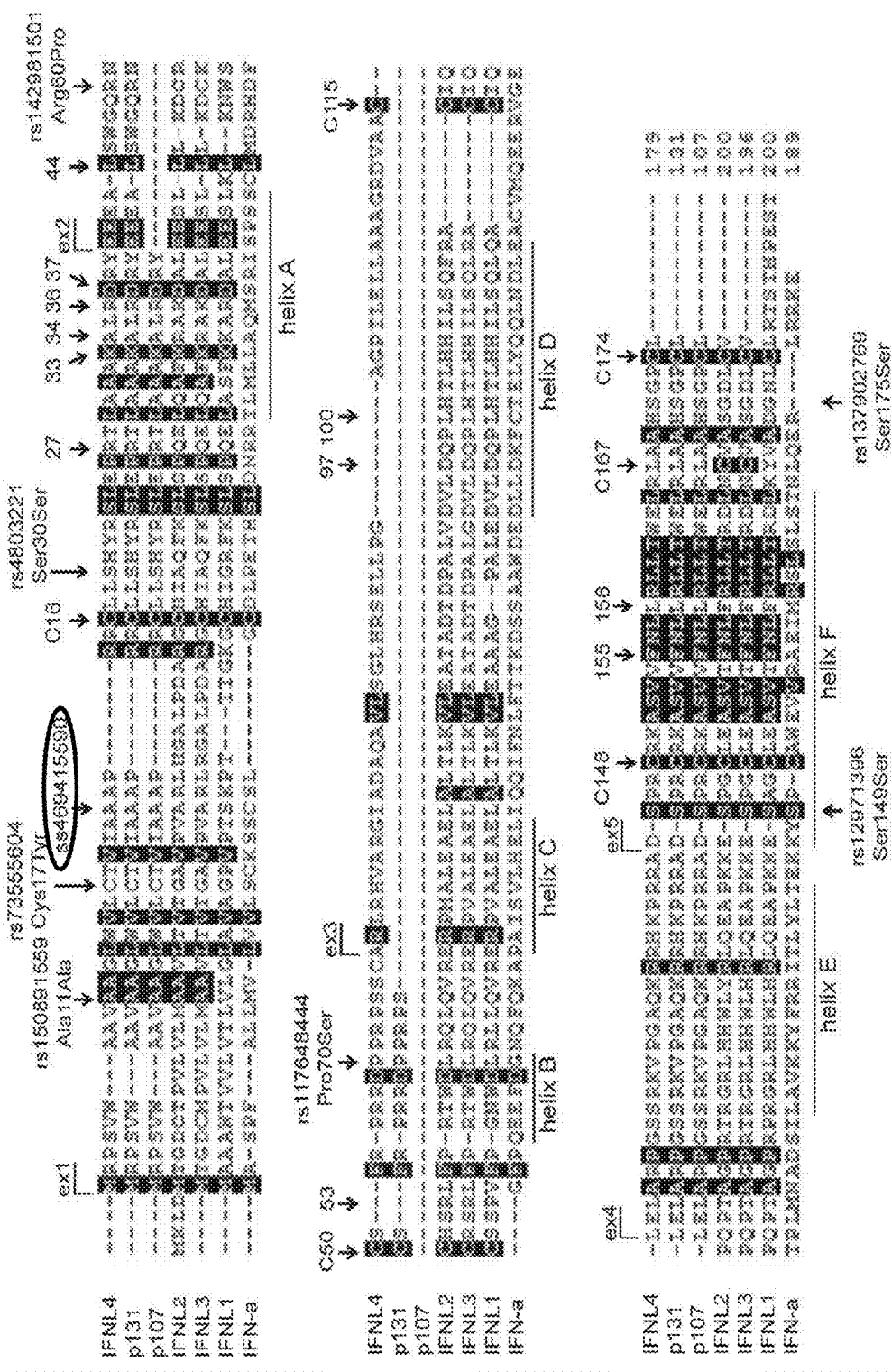
FIG. 7. Amino acid sequence alignment of IFNL4 protein isoforms p179, p131 and p107 and human IFNL1 (IL29), IFNL2 (IL28A), IFNL3 (IL28B) and IFN-α proteins. Shaded—identical amino acids; marked by arrows are positions of cysteines involved in disulfide bonds in IFNL3 (IL28B) protein (C16-C115, C50-C148, C167-C174); positions of frame-shift variant ss469415590, amino acids important for interaction with IL-28R1 (#27, 33, 34, 36, 37, 44, 53, 155, 158) and with IL-10R2(*97, *100) are indicated; numbering is based on mature IFNL3 (IL28B) protein (Q8IZI9), after removal of leader peptide (Gad H, Dellgren, C, et al. Inteferon-λ, is functionally an interferon but structurally related to the interleukin-10 family, the Journal of Biological Chemistry, 2009). Helical protein structure is marked according to Trivella et al. Structure and function of interleukin-22 and other members of the interleukin-10 family, Cell. Mol. Life Sci., 2010. Also indicated are positions of IFNL4 genetic variants.

1). Analysis of these transcripts resulted in the identification of a single transcription site, followed by a protein translation start site, suggesting that a novel protein is produced from this region (FIG. 2). Moreover, deletion of the thymidine at position 39,739,154 causes a frame shift at amino acid 22 of the putative protein, thereby altering the downstream reading frame (FIG. 3). Analysis of transcripts from this region showed that such a frame shift results in production of 6 putative proteins, including 3 novel related proteins: a protein of 179 amino acids (herein referred to as IFNL4-p179), as well as two isoforms of IFNL4, with 131 and 107 amino acids (p131 and p107, respectively) that differ by inclusion of alternative exons. In total, 10 transcripts were detected in the IFNL4 region and deposited to NCBI GenBank (FIG. 4). Expression of IFNL4 mRNA was detected only in PolyI:C-activated hepatocytes from an individual homozygous for a risk ss469415590 ΔG allele but not from an individual homozygous for a non-risk TT allele (FIG. 5). Analysis of the IFNL4-p179 sequence showed that the protein has strong similarity to the human IFN-λ, proteins, particularly to IFNL3 (IL28B), and some other class-2 cytokine family proteins (FIG. 6, FIG. 7).

Accordingly, one embodiment of the present invention is an isolated protein that comprises at least about 30 contiguous amino acids, at least about 40 contiguous amino acids, at least about 50 contiguous amino acids, at least about 60 contiguous amino acids, at least about 70 contiguous amino acids, at least about 80 contiguous amino acids, at least about 90 contiguous amino acids, or at least about 100 contiguous amino acids from an amino acid sequence selected from the group consisting of SEQ ID NO:2, SEQ ID NO:5 and SEQ ID NO:8. In one embodiment, the isolated protein comprises at least about 110 contiguous amino acids, at least about 120 contiguous amino acids, or an at least about 130 contiguous amino acids from an amino acid sequence selected from the group consisting of SEQ ID NO:2 and SEQ ID NO:5. In one embodiment, the isolated protein comprises at least about 140 contiguous amino acids or at least about 150 contiguous amino acids from SEQ ID NO:2. With regard to an amino acid sequence, as used herein, the term "about" means the number of contiguous amino acids can vary by up to 5%. Thus, about 40 contiguous amino acids means the isolated protein can comprise between 38-42 contiguous amino acids. In one embodiment, the isolated protein comprises an amino acid sequence selected from the group consisting of SEQ ID NO:2, SEQ ID NO:5 and SEQ ID NO:8.

Before further embodiments are described, it should be appreciated that, unless defined otherwise, all technical and scientific terms used herein have the same meaning as is commonly understood by one of skill in art to which the subject matter herein belongs. Moreover, in order to aid the reader, the following general definitions are supplied in order to facilitate the understanding of the present invention.

It is to be noted that the term "a" "an" "one or more" and "at least one" can be used interchangeably herein. The terms "comprising," "including," and "having" can also be used interchangeably. Furthermore, the phrase "selected from the group consisting of" refers to one or more members of the group in the list that follows, including mixtures (i.e. combinations) of two or more members. As used herein, "at least one" means one or more. The term "comprise" is generally used in the sense of "including", that is to say "permitting the presence of one or more features or components". It is to be further understood that where descriptions of various embodiments use the term comprising, those skilled in the art would understand that in some specific instances, an embodiment can be alternatively described using the phrase "consisting essentially of".

As used herein, the terms isolated, isolating, purified, and the like, do not necessarily refer to the degree of purity of a cell or molecule of the present invention. Such terms instead refer to cells or molecules that have been separated from their natural milieu or from components of the environment in which they are produced. For example, a naturally occurring cell or molecule (e.g., a DNA molecule, a protein, etc.) present in a living animal, including humans, is not isolated. However, the same cell, or molecule, separated from some or all of the coexisting materials in the animal, is considered isolated. As a further example, according to the present invention, protein molecules that are present in a sample of blood obtained from an individual would be considered isolated. It should be appreciated that protein molecules obtained from such a blood sample using further purification steps would also be referred to as isolated, in accordance with the notion that isolated does not refer to the degree of purity of the cells. Moreover, an isolated protein of the present invention can be obtained, for example, from its natural source (e.g., human), be produced using recombinant DNA technology, or be synthesized chemically.

It is understood by those skilled in the art that the sequence of a protein may vary, or may be altered, with little or no affect on the activity of that protein. According to the present invention, such proteins are referred to as variants, allelic variants, mutants, isoforms, or homologues. Such variants can arise naturally as a result of an individual carrying two different alleles that encode allelic variants, or they can be constructed using techniques such as genetic engineering. With regard to the nomenclature of proteins and their variants, one form of the protein may arbitrarily be designated as the reference form (e.g., wild-type) and other forms designated as mutants, variants, isoforms or homologues. For example, if a particular allele, and thus its encoded protein, is associated with a particular phenotypic characteristic (e.g., the absence of a disease), or is found in the majority of a population, the encoded form of the protein may be referred to as a "wild-type form", while other forms may be referred to as variants, mutants, isoforms, or homologues. With regard to the present invention, a protein comprising the sequence of SEQ ID NO:2, SEQ ID NO:5 or SEQ ID NO:8 will be considered the wild-type (wt) protein.

Thus, one embodiment of the present invention is an IFNL4 protein variant. More specifically, one embodiment of the present invention is an isolated protein that comprises a sequence of at least 50 contiguous amino acids, wherein the at least 50 contiguous amino acid sequence is at least 92% identical, at least 94% identical, at least 96% identical or at least 98% identical over its entire length to an at least 50 contiguous amino acid sequence from SEQ ID NO:2, SEQ ID NO:5 or SEQ ID NO:8. In a further embodiment, the isolated protein comprises a sequence of at least 100 contiguous amino acids, wherein the at least 100 contiguous amino acid sequence is at least 92% identical, at least 94% identical, at least 96% identical or at least 98% identical over its entire length to an at least 100 contiguous amino acid sequence from SEQ ID NO:2, SEQ ID NO:5 or SEQ ID NO:8. In yet a further embodiment, the isolated protein comprises a sequence of at least 150 contiguous amino acids, wherein the at least 150 contiguous amino acid sequence is at least 92% identical, at least 94% identical, at least 96% identical or at least 98% identical over its entire length to an at least 150 contiguous amino acid sequence from SEQ ID NO:2. In one embodiment, the isolated protein comprises an amino acid sequence at least 92% identical, at least 94% identical, at least 96% identical or at least 98% identical over the entire length of an amino acid sequence selected from the group consisting of SEQ ID NO:2, SEQ ID NO:5 and SEQ ID NO:8. Methods of determining the percent identity between two proteins, or nucleic acid molecules, are known to those skilled in the art.

With regard to such variants, any type of alteration in the amino acid sequence is permissible so long as the variant retains at least one IFNL4 protein activity described herein. Examples of such variations include, but are not limited to, amino acid deletions, amino acid insertions, amino acid substitutions and combinations thereof. For example, it is well understood by those skilled in the art that one or more (e.g., 2, 3, 4, 5, 6, 7, 8, 9 or 10), amino acids can often be removed from the amino and/or carboxy terminal ends of a protein without significantly affecting the activity of that protein. Similarly, one or more (e.g., 2, 3, 4, 5, 6, 7, 8, 9 or 10) amino acids can often be inserted into a protein without significantly affecting the activity of the protein.

As noted, isolated variant proteins of the present invention can also contain amino acid substitutions as compared to the wild-type IFNL4 disclosed herein. Any amino acid substitution is permissible so long as the activity of the protein is not significantly affected. In this regard, it is appreciated in the art that amino acids can be classified into groups based on their physical properties. Examples of such groups include, but are not limited to, charged amino acids, uncharged amino acids, polar uncharged amino acids, and hydrophobic amino acids. Preferred variants that contain substitutions are those in which an amino acid is substituted with an amino acid from the same group. Such substitutions are referred to as conservative substitutions.

Naturally occurring residues may be divided into classes based on common side chain properties:
1) hydrophobic: Met, Ala, Val, Leu, Ile;
2) neutral hydrophilic: Cys, Ser, Thr;
3) acidic: Asp, Glu;
4) basic: Asn, Gln, His, Lys, Arg;
5) residues that influence chain orientation: Gly, Pro; and
6) aromatic: Trp, Tyr, Phe.

For example, non-conservative substitutions may involve the exchange of a member of one of these classes for a member from another class. In preferred embodiments, such substituted residues may be introduced into human IFNL4 protein within regions non-homologous to IFN-α and IFN-λ, proteins, In making amino acid changes, the hydropathic index of amino acids may be considered. Each amino acid has been assigned a hydropathic index on the basis of its hydrophobicity and charge characteristics. The hydropathic indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The importance of the hydropathic amino acid index in conferring interactive biological function on a protein is generally understood in the art (Kyte et al., 1982, J. Mol. Biol. 157:105-31). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those within ±1 are particularly preferred, and those within ±0.5 are even more particularly preferred.

It is also understood in the art that the substitution of like amino acids can be made effectively on the basis of hydrophilicity, particularly where the biologically functionally equivalent protein or peptide thereby created is intended for use in immunological embodiments, as in the present case. The greatest local average hydrophilicity of a protein, as governed by the hydrophilicity of its adjacent amino acids, correlates with its immunogenicity and antigenicity, i.e., with a biological property of the protein. The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, the substitution of amino acids whose hydrophilicity values are within ±2 is preferred, those within ±1 are particularly preferred, and those within ±0.5 are even more particularly preferred. One may also identify epitopes from primary amino acid sequences on the basis of hydrophilicity.

Desired amino acid substitutions (whether conservative or non-conservative) can be determined by those skilled in the art at the time such substitutions are desired. For example, amino acid substitutions can be used to identify important residues of the IFNL4 protein, or to increase or decrease the affinity of the IFNL4 proteins described herein. Exemplary amino acid substitutions are shown below in Table 1.

TABLE 1

Amino Acid Substitutions

| Original Amino Acid | Exemplary Substitutions |
| --- | --- |
| Ala | Val, Leu, Ile |
| Arg | Lys, Gln, Asn |
| Asn | Gln |
| Asp | Glu |
| Cys | Ser, Ala |
| Gln | Asn |
| Glu | Asp |
| Gly | Pro, Ala |
| His | Asn, Gln, Lys, Arg |
| Ile | Leu, Val, Met, Ala |
| Leu | Ile, Val, Met, Ala |
| Lys | Arg, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala |

Thus, in one embodiment of the present invention, the IFNL4 protein variant comprises at least one amino acid substitution, wherein the substitution is a conservative substitution. In one embodiment, the original amino acid is substituted with an exemplary substitution shown in Table 1.

With regard to amino acid substitutions, it has previously been discussed that IFNL4 proteins of the present invention share up to 29% sequence identity (and 40% sequence similarity) with human IFN-λ, proteins. Moreover, it is understood by those skilled in the art, that interferon proteins have several amino acids that are conserved. The presently disclosed IFNL4 proteins contain many of these conserved amino acids. Such amino acids are highlighted in FIG. 7. Amino acids 27, 33, 34, 36, 37, 44, 53, 155 and 158 are important for IFNL3 (IL28B) interaction with its first receptor IFNLR1 (IL28R1), while amino acids 97 and 100 are important for interaction with the second receptor, IL10R2 (Gad H, Dellgren, C, et al. Inteferon-λ, is functionally an interferon but structurally related to the interleukin-10 family, the Journal of Biological Chemistry, 2009). Thus, in various embodiments, isolated variant proteins of the present invention contain at least one, or all, of these conserved interferon residues. Accordingly, one embodiment of the present invention is an isolated protein that comprises a sequence of at least 50 contiguous amino acids, wherein the at least 50 contiguous amino acid sequence is at least 92% identical, at least 94% identical, at least 96% identical or at least 98% identical over its entire length to an at least 50 contiguous amino acid sequence from SEQ ID NO:2, SEQ ID NO:5 or SEQ ID NO:8, and wherein the at least 50 contiguous amino acid sequence comprises at least one sequence feature selected from the group consisting of:

a. a cysteine residue at the position corresponding to position 27 of SEQ ID NO:2;
 b. an leucine residue at the position corresponding to position 29 of SEQ ID NO:2
 c. a serine residue at the position corresponding to position 30 of SEQ ID NO:2
 d. a tyrosine residue at the position corresponding to position 32 of SEQ ID NO:2
 e. a serine residue at the position corresponding to position 34 of SEQ ID NO:2
 f. a proline residue at the position corresponding to position 37 of SEQ ID NO:2;
 g. a leucine residue at the position corresponding to position 40 of SEQ ID NO:2;
 h. an alanine residue at the position corresponding to position 42 of SEQ ID
 i. a lysine residue at the position corresponding to position 44 of SEQ ID NO:2;
 j. an aspartic acid residue at the position corresponding to position 48 of SEQ ID NO:2;
 k. a tyrosine residue at the position corresponding to position 50 of SEQ ID NO:2;
 l. a leucine residue at the position corresponding to position 111 of SEQ ID NO:2;
 m. a leucine residue at the position corresponding to position 112 of SEQ ID NO:2;
 n. an aspartic acid residue at the position corresponding to position 118 of SEQ ID NO:2;
 o. an alanine residue at the position corresponding to position 120 of SEQ ID NO:2;
 p. a cysteine residue at the position corresponding to position 122 of SEQ ID NO:2;
 q. a cysteine residue at the position corresponding to position 152 of SEQ ID NO:2;
 r. a valine residue at the position corresponding to position 157 of SEQ ID NO:2;
 s. an asparagine residue at the position corresponding to position 160 of SEQ ID NO:2;
 t. a leucine residue at the position corresponding to position 161 of SEQ ID NO:2;
 u. an arginine residue at the position corresponding to position 163 of SEQ ID NO:2
 v. a leucine residue at the position corresponding to position 165 of SEQ ID NO:2;
 w. a threonine residue at the position corresponding to position 166 of SEQ ID NO:2;
 x. an alanine residue at the position corresponding to position 173 of SEQ ID NO:2; and
 y. a cysteine residue at the position corresponding to position 178 of SEQ ID NO:2.

One embodiment, the isolated protein comprises at least 2, 3, 4, 5, 5, 7, 8, 9, 10, 11, 12, 13, 14, 15, 16, 17, 18, 19, 20, 21, 22, 23, 24 or 25 of any of sequence elements a-y.

In one embodiment, the isolated protein comprises a sequence of at least 50 contiguous amino acids, wherein the at least 50 contiguous amino acid sequence is at least 92% identical, at least 94% identical, at least 96% identical or at least 98% identical over its entire length to an at least 50 contiguous amino acid sequence from SEQ ID NO:2, SEQ ID NO:5 or SEQ ID NO:8, and wherein the isolated protein comprises:

a. a cysteine residue at the position corresponding to position 27 of SEQ ID NO:2;
 b. an leucine residue at the position corresponding to position 29 of SEQ ID NO:2
 c. a serine residue at the position corresponding to position 30 of SEQ ID NO:2
 d. a tyrosine residue at the position corresponding to position 32 of SEQ ID NO:2
 e. a serine residue at the position corresponding to position 34 of SEQ ID NO:2
 f. a proline residue at the position corresponding to position 37 of SEQ ID NO:2;
 g. a leucine residue at the position corresponding to position 40 of SEQ ID NO:2;
 h. an alanine residue at the position corresponding to position 42 of SEQ ID NO:2;
 i. a lysine residue at the position corresponding to position 44 of SEQ ID NO:2;
 j. an aspartic acid residue at the position corresponding to position 48 of SEQ ID NO:2;
 k. a tyrosine residue at the position corresponding to position 50 of SEQ ID NO:2;
 l. a leucine residue at the position corresponding to position 111 of SEQ ID NO:2;
 m. a leucine residue at the position corresponding to position 112 of SEQ ID NO:2;
 n. an aspartic acid residue at the position corresponding to position 118 of SEQ ID NO:2;
 o. an alanine residue at the position corresponding to position 120 of SEQ ID NO:2;
 p. a cysteine residue at the position corresponding to position 122 of SEQ ID NO:2;
 q. a cysteine residue at the position corresponding to position 152 of SEQ ID NO:2;
 r. a valine residue at the position corresponding to position 157 of SEQ ID NO:2;
 s. an asparagine residue at the position corresponding to position 160 of SEQ ID NO:2;
 t. a leucine residue at the position corresponding to position 161 of SEQ ID NO:2;
 u. an arginine residue at the position corresponding to position 163 of SEQ ID NO:2
 v. a leucine residue at the position corresponding to position 165 of SEQ ID NO:2;
 w. a threonine residue at the position corresponding to position 166 of SEQ ID NO:2;
 x. an alanine residue at the position corresponding to position 173 of SEQ ID NO:2; and
 y. a cysteine residue at the position corresponding to position 178 of SEQ ID NO:2.

In one embodiment, the isolated protein comprises a sequence of at least 100 contiguous amino acids, wherein the at least 100 contiguous amino acid sequence is at least 92% identical, at least 94% identical, at least 96% identical or at least 98% identical over its entire length to an at least 100 contiguous amino acid sequence from SEQ ID NO:2, SEQ ID NO:5 or SEQ ID NO:8, and wherein the at least 100 contiguous amino acid sequence comprises at least one sequence feature selected from the group consisting of:
   a. a cysteine residue at the position corresponding to position 27 of SEQ ID NO:2;
   b. an leucine residue at the position corresponding to position 29 of SEQ ID NO:2
   c. a serine residue at the position corresponding to position 30 of SEQ ID NO:2
   d. a tyrosine residue at the position corresponding to position 32 of SEQ ID NO:2
   e. a serine residue at the position corresponding to position 34 of SEQ ID NO:2
   f. a proline residue at the position corresponding to position 37 of SEQ ID NO:2;
   g. a leucine residue at the position corresponding to position 40 of SEQ ID NO:2;
   h. an alanine residue at the position corresponding to position 42 of SEQ ID NO:2;
   i. a lysine residue at the position corresponding to position 44 of SEQ ID NO:2;
   j. an aspartic acid residue at the position corresponding to position 48 of SEQ ID NO:2;
   k. a tyrosine residue at the position corresponding to position 50 of SEQ ID NO:2;
   l. a leucine residue at the position corresponding to position 111 of SEQ ID NO:2;
   m. a leucine residue at the position corresponding to position 112 of SEQ ID NO:2;
   n. an aspartic acid residue at the position corresponding to position 118 of SEQ ID NO:2;
   o. an alanine residue at the position corresponding to position 120 of SEQ ID NO:2;
   p. a cysteine residue at the position corresponding to position 122 of SEQ ID NO:2;
   q. a cysteine residue at the position corresponding to position 152 of SEQ ID NO:2;
   r. a valine residue at the position corresponding to position 157 of SEQ ID NO:2;
   s. an asparagine residue at the position corresponding to position 160 of SEQ ID NO:2;
   t. a leucine residue at the position corresponding to position 161 of SEQ ID NO:2;
   u. an arginine residue at the position corresponding to position 163 of SEQ ID NO:2
   v. a leucine residue at the position corresponding to position 165 of SEQ ID NO:2;
   w. a threonine residue at the position corresponding to position 166 of SEQ ID NO:2;
   x. an alanine residue at the position corresponding to position 173 of SEQ ID NO:2; and
   y. a cysteine residue at the position corresponding to position 178 of SEQ ID NO:2.
In one embodiment, the isolated protein comprises at least 1, 2, 3, 4, 5, 6, 7, 8, 9, 10, 11, 12, 13, 14, 15, 16, 17, 18, 19, 20, 21, 22, 23, 24 or 25 of any of sequence elements a-y.

In one embodiment, the isolated protein comprises a sequence of at least 100 contiguous amino acids, wherein the at least 100 contiguous amino acid sequence is at least 92% identical, at least 94% identical, at least 96% identical or at least 98% identical over its entire length to an at least 100 contiguous amino acid sequence from SEQ ID NO:2, SEQ ID NO:5 or SEQ ID NO:8, and wherein the isolated protein comprises:
   a. a cysteine residue at the position corresponding to position 27 of SEQ ID NO:2;
   b. an leucine residue at the position corresponding to position 29 of SEQ ID NO:2
   c. a serine residue at the position corresponding to position 30 of SEQ ID NO:2
   d. a tyrosine residue at the position corresponding to position 32 of SEQ ID NO:2
   e. a serine residue at the position corresponding to position 34 of SEQ ID NO:2
   f. a proline residue at the position corresponding to position 37 of SEQ ID NO:2;
   g. a leucine residue at the position corresponding to position 40 of SEQ ID NO:2;
   h. an alanine residue at the position corresponding to position 42 of SEQ IDNO:2;
   i. a lysine residue at the position corresponding to position 44 of SEQ ID NO:2;
   j. an aspartic acid residue at the position corresponding to position 48 of SEQ ID NO:2;
   k. a tyrosine residue at the position corresponding to position 50 of SEQ ID NO:2;
   l. a leucine residue at the position corresponding to position 111 of SEQ ID NO:2;
   m. a leucine residue at the position corresponding to position 112 of SEQ ID NO:2;
   n. an aspartic acid residue at the position corresponding to position 118 of SEQ ID NO:2;
   o. an alanine residue at the position corresponding to position 120 of SEQ ID NO:2;
   p. a cysteine residue at the position corresponding to position 122 of SEQ ID NO:2;
   q. a cysteine residue at the position corresponding to position 152 of SEQ ID NO:2;
   r. a valine residue at the position corresponding to position 157 of SEQ ID NO:2;
   s. an asparagine residue at the position corresponding to position 160 of SEQ ID NO:2;
   t. a leucine residue at the position corresponding to position 161 of SEQ ID NO:2;
   u. an arginine residue at the position corresponding to position 163 of SEQ ID NO:2
   v. a leucine residue at the position corresponding to position 165 of SEQ ID NO:2;
   w. a threonine residue at the position corresponding to position 166 of SEQ ID NO:2;
   x. an alanine residue at the position corresponding to position 173 of SEQ ID NO:2; and
   y. a cysteine residue at the position corresponding to position 178 of SEQ ID NO:2.

In one embodiment, the isolated protein comprises a sequence of at least 130 contiguous amino acids, wherein the at least 130 contiguous amino acid sequence is at least 92% identical, at least 94% identical, at least 96% identical or at least 98% identical over its entire length to an at least 130 contiguous amino acid sequence from SEQ ID NO:2 or SEQ ID NO:5, and wherein the at least 130 contiguous amino acid sequence comprises at least one sequence feature selected from the group consisting of:
   a. a cysteine residue at the position corresponding to position 27 of SEQ ID NO:2;
   b. an leucine residue at the position corresponding to position 29 of SEQ ID NO:2 c. a serine residue at the position corresponding to position 30 of SEQ ID NO:2
d. a tyrosine residue at the position corresponding to position 32 of SEQ ID NO:2
e. a serine residue at the position corresponding to position 34 of SEQ ID NO:2
f. a proline residue at the position corresponding to position 37 of SEQ ID NO:2;
g. a leucine residue at the position corresponding to position 40 of SEQ ID NO:2;
h. an alanine residue at the position corresponding to position 42 of SEQ ID NO:2;
i. a lysine residue at the position corresponding to position 44 of SEQ ID NO:2;
j. an aspartic acid residue at the position corresponding to position 48 of SEQ ID NO:2;
k. a tyrosine residue at the position corresponding to position 50 of SEQ ID NO:2;
l. a glutamic acid residue at the position corresponding to position 51 of SEQ ID NO:2;
m. a cysteine residue at the position corresponding to position 62 of SEQ ID NO:2;
n. a leucine residue at the position corresponding to position 111 of SEQ ID NO:2;
o. a leucine residue at the position corresponding to position 112 of SEQ ID NO:2;
p. an aspartic acid residue at the position corresponding to position 118 of SEQ ID NO:2;
q. an alanine residue at the position corresponding to position 120 of SEQ ID NO:2;
r. a cysteine residue at the position corresponding to position 122 of SEQ ID NO:2;
s. a cysteine residue at the position corresponding to position 152 of SEQ ID NO:2;
t. a valine residue at the position corresponding to position 157 of SEQ ID NO:2;
u. an asparagine residue at the position corresponding to position 160 of SEQ ID NO:2;
v. a leucine residue at the position corresponding to position 161 of SEQ IDNO:2;
w. an arginine residue at the position corresponding to position 163 of SEQ ID NO:2
x. a leucine residue at the position corresponding to position 165 of SEQ ID NO:2;
y. a threonine residue at the position corresponding to position 166 of SEQ ID NO:2;
z. an alanine residue at the position corresponding to position 173 of SEQ ID NO:2; and
aa. a cysteine residue at the position corresponding to position 178 of SEQ ID NO:2.

In one embodiment, the isolated protein comprises at least 1, 2, 3, 4, 5, 6, 7, 8, 9, 10, 11, 12, 13, 14, 15, 16, 17, 18, 19, 20, 21, 22, 23, 24, 25, 26 or 27 of any of sequence elements a-aa.

In one embodiment, the isolated protein comprises a sequence of at least 130 contiguous amino acids, wherein the at least 130 contiguous amino acid sequence is at least 92% identical, at least 94% identical, at least 96% identical or at least 98% identical over its entire length to an at least 130 contiguous amino acid sequence from SEQ ID NO:2 or SEQ ID NO:5, and wherein the isolated protein comprises:
a. a cysteine residue at the position corresponding to position 27 of SEQ ID NO:2;
b. an leucine residue at the position corresponding to position 29 of SEQ ID NO:2
c. a serine residue at the position corresponding to position 30 of SEQ ID NO:2
d. a tyrosine residue at the position corresponding to position 32 of SEQ ID NO:2
e. a serine residue at the position corresponding to position 34 of SEQ ID NO:2
f. a proline residue at the position corresponding to position 37 of SEQ ID NO:2;
g. a leucine residue at the position corresponding to position 40 of SEQ ID NO:2;
h. an alanine residue at the position corresponding to position 42 of SEQ ID NO:2;
i. a lysine residue at the position corresponding to position 44 of SEQ ID NO:2;
j. an aspartic acid residue at the position corresponding to position 48 of SEQ ID NO:2;
k. a tyrosine residue at the position corresponding to position 50 of SEQ ID NO:2;
l. a glutamic acid residue at the position corresponding to position 51 of SEQ ID NO:2;
m. a cysteine residue at the position corresponding to position 62 of SEQ IDNO:2
n. a leucine residue at the position corresponding to position 111 of SEQ ID NO:2;
o. a leucine residue at the position corresponding to position 112 of SEQ ID NO:2;
p. an aspartic acid residue at the position corresponding to position 118 of SEQ ID NO:2;
q. an alanine residue at the position corresponding to position 120 of SEQ ID NO:2;
r. a cysteine residue at the position corresponding to position 122 of SEQ ID NO:2;
s. a cysteine residue at the position corresponding to position 152 of SEQ ID NO:2;
t. a valine residue at the position corresponding to position 157 of SEQ ID NO:2;
u. an asparagine residue at the position corresponding to position 160 of SEQ ID NO:2;
v. a leucine residue at the position corresponding to position 161 of SEQ ID NO:2;
w. an arginine residue at the position corresponding to position 163 of SEQ ID NO:2
x. a leucine residue at the position corresponding to position 165 of SEQ ID NO:2;
y. a threonine residue at the position corresponding to position 166 of SEQ ID NO:2;
z. an alanine residue at the position corresponding to position 173 of SEQ ID NO:2; and
aa. a cysteine residue at the position corresponding to position 178 of SEQ ID NO:2.

In one embodiment, the isolated protein comprises a sequence of at least 150 contiguous amino acids, wherein the at least 150 contiguous amino acid sequence is at least 92% identical, at least 94% identical, at least 96% identical or at least 98% identical over its entire length to an at least 150 contiguous amino acid sequence from SEQ ID NO:2, and wherein the at least 150 contiguous amino acid sequence comprises at least one sequence feature selected from the group consisting of:
a. a cysteine residue at the position corresponding to position 27 of SEQ ID NO:2;
b. an leucine residue at the position corresponding to position 29 of SEQ ID NO:2
c. a serine residue at the position corresponding to position 30 of SEQ ID NO:2
d. a tyrosine residue at the position corresponding to position 32 of SEQ ID NO:2
e. a serine residue at the position corresponding to position 34 of SEQ ID NO:2 f. a proline residue at the position corresponding to position 37 of SEQ ID NO:2;
g. a leucine residue at the position corresponding to position 40 of SEQ ID NO:2;
h. an alanine residue at the position corresponding to position 42 of SEQ ID NO:2;
i. a lysine residue at the position corresponding to position 44 of SEQ ID NO:2;
j. an aspartic acid residue at the position corresponding to position 48 of SEQ ID NO:2;
k. a tyrosine residue at the position corresponding to position 50 of SEQ ID NO:2;
l. a glutamic acid residue at the position corresponding to position 51 of SEQ ID NO:2;
m. a cysteine residue at the position corresponding to position 62 of SEQ ID NO:2;
n. a cysteine residue at the position corresponding to position 76 of SEQ ID NO:2;
o. an alanine residue at the position corresponding to position 87 of SEQ ID NO:2;
p. a leucine residue at the position corresponding to position 111 of SEQ ID NO:2;
q. a leucine residue at the position corresponding to position 112 of SEQ ID NO:2;
r. an aspartic acid residue at the position corresponding to position 118 of SEQ ID NO:2;
s. an alanine residue at the position corresponding to position 120 of SEQ ID NO:2;
t. a cysteine residue at the position corresponding to position 122 of SEQ ID NO:2;
u. a cysteine residue at the position corresponding to position 152 of SEQ ID NO:2;
v. a valine residue at the position corresponding to position 157 of SEQ ID NO:2;
w. an asparagine residue at the position corresponding to position 160 of SEQ ID NO:2;
x. a leucine residue at the position corresponding to position 161 of SEQ ID NO:2;
y. an arginine residue at the position corresponding to position 163 of SEQ ID NO:2
z. a leucine residue at the position corresponding to position 165 of SEQ ID NO:2;
aa. a threonine residue at the position corresponding to position 166 of SEQ ID NO:2;
bb. an alanine residue at the position corresponding to position 173 of SEQ ID NO:2; and
cc. a cysteine residue at the position corresponding to position 178 of SEQ ID NO:2.

In one embodiment the isolated protein comprises at least 1, 2, 3, 4, 5, 6, 7, 8, 9, 10, 11, 12, 13, 14, 15, 16, 17, 18, 19, 20, 21, 22, 23, 24, 25, 26, 27, 28 or 29 of any of sequence elements a-cc.

In one embodiment, the isolated protein comprises a sequence of at least 150 contiguous amino acids, wherein the at least 150 contiguous amino acid sequence is at least 92% identical, at least 94% identical, at least 96% identical or at least 98% identical over its entire length to an at least 150 contiguous amino acid sequence from SEQ ID NO:2, and wherein the isolated protein comprises:
a. a cysteine residue at the position corresponding to position 27 of SEQ ID NO:2;
b. an leucine residue at the position corresponding to position 29 of SEQ ID NO:2
c. a serine residue at the position corresponding to position 30 of SEQ ID NO:2
d. a tyrosine residue at the position corresponding to position 32 of SEQ ID NO:2
e. a serine residue at the position corresponding to position 34 of SEQ ID NO:2
f. a proline residue at the position corresponding to position 37 of SEQ ID NO:2;
g. a leucine residue at the position corresponding to position 40 of SEQ ID NO:2;
h. an alanine residue at the position corresponding to position 42 of SEQ ID NO:2;
i. a lysine residue at the position corresponding to position 44 of SEQ ID NO:2;
j. an aspartic acid residue at the position corresponding to position 48 of SEQ ID NO:2;
k. a tyrosine residue at the position corresponding to position 50 of SEQ ID NO:2;
l. a glutamic acid residue at the position corresponding to position 51 of SEQ ID NO:2;
m. a cysteine residue at the position corresponding to position 62 of SEQ ID
n. a cysteine residue at the position corresponding to position 76 of SEQ ID NO:2;
o. an alanine residue at the position corresponding to position 87 of SEQ ID NO:2;
p. a leucine residue at the position corresponding to position 111 of SEQ ID NO:2;
q. a leucine residue at the position corresponding to position 112 of SEQ ID NO:2;
r. an aspartic acid residue at the position corresponding to position 118 of SEQ ID NO:2;
s. an alanine residue at the position corresponding to position 120 of SEQ ID NO:2;
t. a cysteine residue at the position corresponding to position 122 of SEQ ID NO:2;
u. a cysteine residue at the position corresponding to position 152 of SEQ ID NO:2;
v. a valine residue at the position corresponding to position 157 of SEQ ID NO:2;
w. an asparagine residue at the position corresponding to position 160 of SEQ ID NO:2;
x. a leucine residue at the position corresponding to position 161 of SEQ ID NO:2;
y. an arginine residue at the position corresponding to position 163 of SEQ ID NO:2
z. a leucine residue at the position corresponding to position 165 of SEQ ID NO:2;
aa. a threonine residue at the position corresponding to position 166 of SEQ ID NO:2;
bb. an alanine residue at the position corresponding to position 173 of SEQ ID NO:2; and
cc. a cysteine residue at the position corresponding to position 178 of SEQ ID NO:2.

One embodiment of the present invention is an isolated protein comprising an amino acid sequence at least 85% identical, at least 90% identical, at least 92% identical, at least 94% identical, at least 96% identical or at least 98% identical over its entire length to SEQ ID NO:8, wherein the isolated protein comprises at least one sequence feature selected from the group consisting of:
a. a cysteine residue at the position corresponding to position 27 of SEQ ID NO:2;
b. an leucine residue at the position corresponding to position 29 of SEQ ID NO:2
c. a serine residue at the position corresponding to position 30 of SEQ ID NO:2
d. a tyrosine residue at the position corresponding to position 32 of SEQ ID NO:2
e. a serine residue at the position corresponding to position 34 of SEQ ID NO:2 f. a proline residue at the position corresponding to position 37 of SEQ ID NO:2;
g. a leucine residue at the position corresponding to position 40 of SEQ ID NO:2;
h. an alanine residue at the position corresponding to position 42 of SEQ ID NO:2;
i. a lysine residue at the position corresponding to position 44 of SEQ ID NO:2;
j. an aspartic acid residue at the position corresponding to position 48 of SEQ ID NO:2;
k. a tyrosine residue at the position corresponding to position 50 of SEQ ID NO:2;
l. a leucine residue at the position corresponding to position 111 of SEQ ID NO:2;
m. a leucine residue at the position corresponding to position 112 of SEQ ID NO:2;
n. an aspartic acid residue at the position corresponding to position 118 of SEQ ID NO:2;
o. an alanine residue at the position corresponding to position 120 of SEQ ID NO:2;
p. a cysteine residue at the position corresponding to position 122 of SEQ ID NO:2;
q. a cysteine residue at the position corresponding to position 152 of SEQ ID NO:2;
r. a valine residue at the position corresponding to position 157 of SEQ ID NO:2;
s. an asparagine residue at the position corresponding to position 160 of SEQ ID NO:2;
t. a leucine residue at the position corresponding to position 161 of SEQ ID NO:2;
u. an arginine residue at the position corresponding to position 163 of SEQ ID NO:2
v. a leucine residue at the position corresponding to position 165 of SEQ ID NO:2;
w. a threonine residue at the position corresponding to position 166 of SEQ IDNO:2;
x. an alanine residue at the position corresponding to position 173 of SEQ ID NO:2; and
y. a cysteine residue at the position corresponding to position 178 of SEQ ID NO:2.

In one embodiment, the isolated protein comprises at least 2, 3, 4, 5, 5, 7, 8, 9, 10, 11, 12, 13, 14, 15, 16, 17, 18, 19, 20, 21, 22, 23, 24 or 25 of any of sequence elements a-y.

One embodiment of the present invention is an isolated protein comprising an amino acid sequence at least 85% identical, at least 90% identical, at least 92% identical, at least 94% identical, at least 96% identical or at least 98% identical over its entire length to SEQ ID NO:8, wherein the isolated protein comprises:
a. a cysteine residue at the position corresponding to position 27 of SEQ ID NO:2;
b. an leucine residue at the position corresponding to position 29 of SEQ ID NO:2
c. a serine residue at the position corresponding to position 30 of SEQ ID NO:2
d. a tyrosine residue at the position corresponding to position 32 of SEQ ID NO:2
e. a serine residue at the position corresponding to position 34 of SEQ ID NO:2
f. a proline residue at the position corresponding to position 37 of SEQ ID NO:2;
g. a leucine residue at the position corresponding to position 40 of SEQ ID NO:2;
h. an alanine residue at the position corresponding to position 42 of SEQ ID NO:2;
i. a lysine residue at the position corresponding to position 44 of SEQ ID NO:2;
j. an aspartic acid residue at the position corresponding to position 48 of SEQ ID NO:2;
k. a tyrosine residue at the position corresponding to position 50 of SEQ ID NO:2;
l. a leucine residue at the position corresponding to position 111 of SEQ ID NO:2;
m. a leucine residue at the position corresponding to position 112 of SEQ ID NO:2;
n. an aspartic acid residue at the position corresponding to position 118 of SEQ ID NO:2;
o. an alanine residue at the position corresponding to position 120 of SEQ ID NO:2;
p. a cysteine residue at the position corresponding to position 122 of SEQ IDNO:2;
q. a cysteine residue at the position corresponding to position 152 of SEQ ID NO:2;
r. a valine residue at the position corresponding to position 157 of SEQ ID NO:2;
s. an asparagine residue at the position corresponding to position 160 of SEQ ID NO:2;
t. a leucine residue at the position corresponding to position 161 of SEQ ID NO:2;
u. an arginine residue at the position corresponding to position 163 of SEQ ID NO:2
v. a leucine residue at the position corresponding to position 165 of SEQ ID NO:2;
w. a threonine residue at the position corresponding to position 166 of SEQ ID NO:2;
x. an alanine residue at the position corresponding to position 173 of SEQ ID NO:2; and
y. a cysteine residue at the position corresponding to position 178 of SEQ ID NO:2.

One embodiment of the present invention is an isolated protein comprising an amino acid sequence at least 85% identical, at least 90% identical, at least 92% identical, at least 94% identical, at least 96% identical or at least 98% identical over its entire length to SEQ ID NO:5, wherein the isolated protein comprises at least one sequence feature selected from the group consisting of:
a. a cysteine residue at the position corresponding to position 27 of SEQ ID NO:2;
b. an leucine residue at the position corresponding to position 29 of SEQ ID NO:2
c. a serine residue at the position corresponding to position 30 of SEQ ID NO:2
d. a tyrosine residue at the position corresponding to position 32 of SEQ ID NO:2
e. a serine residue at the position corresponding to position 34 of SEQ ID NO:2
f. a proline residue at the position corresponding to position 37 of SEQ ID NO:2;
g. a leucine residue at the position corresponding to position 40 of SEQ ID NO:2;
h. an alanine residue at the position corresponding to position 42 of SEQ ID NO:2;
i. a lysine residue at the position corresponding to position 44 of SEQ ID NO:2;
j. an aspartic acid residue at the position corresponding to position 48 of SEQ IDNO:2;
k. a tyrosine residue at the position corresponding to position 50 of SEQ ID NO:2;
l. a glutamic acid residue at the position corresponding to position 51 of SEQ ID NO:2;
m. a cysteine residue at the position corresponding to position 62 of SEQ ID NO:2;
n. a leucine residue at the position corresponding to position 111 of SEQ ID NO:2;

o. a leucine residue at the position corresponding to position 112 of SEQ ID NO:2;
p. an aspartic acid residue at the position corresponding to position 118 of SEQ ID NO:2;
q. an alanine residue at the position corresponding to position 120 of SEQ ID NO:2;
r. a cysteine residue at the position corresponding to position 122 of SEQ ID NO:2;
s. a cysteine residue at the position corresponding to position 152 of SEQ ID NO:2;
t. a valine residue at the position corresponding to position 157 of SEQ ID NO:2;
u. an asparagine residue at the position corresponding to position 160 of SEQ ID NO:2;
v. a leucine residue at the position corresponding to position 161 of SEQ ID NO:2;
w. an arginine residue at the position corresponding to position 163 of SEQ ID NO:2
x. a leucine residue at the position corresponding to position 165 of SEQ ID NO:2;
y. a threonine residue at the position corresponding to position 166 of SEQ ID NO:2;
z. an alanine residue at the position corresponding to position 173 of SEQ ID NO:2; and
aa. a cysteine residue at the position corresponding to position 178 of SEQ ID NO:2.

In one embodiment the isolated protein comprises at least 1, 2, 3, 4, 5, 6, 7, 8, 9, 10, 11, 12, 13, 14, 15, 16, 17, 18, 19, 20, 21, 22, 23, 24, 25, 26 or 27 of any of sequence elements a-aa.

One embodiment of the present invention is an isolated protein comprising an amino acid sequence at least 85% identical, at least 90% identical, at least 92% identical, at least 94% identical, at least 96% identical or at least 98% identical over its entire length to SEQ ID NO:5, wherein the isolated protein comprises:
a. a cysteine residue at the position corresponding to position 27 of SEQ ID NO:2;
b. an leucine residue at the position corresponding to position 29 of SEQ ID NO:2
c. a serine residue at the position corresponding to position 30 of SEQ ID NO:2
d. a tyrosine residue at the position corresponding to position 32 of SEQ ID NO:2
e. a serine residue at the position corresponding to position 34 of SEQ ID NO:2
f. a proline residue at the position corresponding to position 37 of SEQ ID NO:2;
g. a leucine residue at the position corresponding to position 40 of SEQ ID NO:2;
h. an alanine residue at the position corresponding to position 42 of SEQ ID NO:2;
i. a lysine residue at the position corresponding to position 44 of SEQ ID NO:2;
j. an aspartic acid residue at the position corresponding to position 48 of SEQ ID NO:2;
k. a tyrosine residue at the position corresponding to position 50 of SEQ ID NO:2;
l. a glutamic acid residue at the position corresponding to position 51 of SEQ ID NO:2;
m. a cysteine residue at the position corresponding to position 62 of SEQ ID NO:2;
n. a leucine residue at the position corresponding to position 111 of SEQ ID NO:2;
o. a leucine residue at the position corresponding to position 112 of SEQ ID NO:2;
p. an aspartic acid residue at the position corresponding to position 118 of SEQ ID NO:2;
q. an alanine residue at the position corresponding to position 120 of SEQ ID NO:2;
r. a cysteine residue at the position corresponding to position 122 of SEQ ID NO:2;
s. a cysteine residue at the position corresponding to position 152 of SEQ ID NO:2;
t. a valine residue at the position corresponding to position 157 of SEQ ID NO:2;
u. an asparagine residue at the position corresponding to position 160 of SEQ ID NO:2;
v. a leucine residue at the position corresponding to position 161 of SEQ IDNO:2;
w. an arginine residue at the position corresponding to position 163 of SEQ ID NO:2
x. a leucine residue at the position corresponding to position 165 of SEQ ID NO:2;
y. a threonine residue at the position corresponding to position 166 of SEQ ID NO:2;
z. an alanine residue at the position corresponding to position 173 of SEQ ID NO:2; and
aa. a cysteine residue at the position corresponding to position 178 of SEQ ID NO:2.

In one embodiment, the isolated protein comprises an amino acid sequence at least 85% identical, at least 90% identical, at least 92% identical, at least 94% identical, at least 96% identical or at least 98% identical over its entire length to SEQ ID NO:2, wherein the isolated protein comprises at least one sequence feature selected from the group consisting of:
a. a cysteine residue at the position corresponding to position 27 of SEQ ID NO:2;
b. an leucine residue at the position corresponding to position 29 of SEQ ID NO:2
c. a serine residue at the position corresponding to position 30 of SEQ ID NO:2
d. a tyrosine residue at the position corresponding to position 32 of SEQ ID NO:2
e. a serine residue at the position corresponding to position 34 of SEQ ID NO:2
f. a proline residue at the position corresponding to position 37 of SEQ ID NO:2;
g. a leucine residue at the position corresponding to position 40 of SEQ ID NO:2;
h. an alanine residue at the position corresponding to position 42 of SEQ ID NO:2;
i. a lysine residue at the position corresponding to position 44 of SEQ ID NO:2;
j. an aspartic acid residue at the position corresponding to position 48 of SEQ ID NO:2;
k. a tyrosine residue at the position corresponding to position 50 of SEQ ID NO:2;
l. a glutamic acid residue at the position corresponding to position 51 of SEQ ID NO:2;
m. a cysteine residue at the position corresponding to position 62 of SEQ ID NO:2;
n. a cysteine residue at the position corresponding to position 76 of SEQ IDNO:2;
o. an alanine residue at the position corresponding to position 87 of SEQ ID NO:2;
p. a leucine residue at the position corresponding to position 111 of SEQ ID NO:2;
q. a leucine residue at the position corresponding to position 112 of SEQ ID NO:2;
r. an aspartic acid residue at the position corresponding to position 118 of SEQ ID NO:2;

s. an alanine residue at the position corresponding to position 120 of SEQ ID NO:2;
t. a cysteine residue at the position corresponding to position 122 of SEQ ID NO:2;
u. a cysteine residue at the position corresponding to position 152 of SEQ ID NO:2;
v. a valine residue at the position corresponding to position 157 of SEQ ID NO:2;
w. an asparagine residue at the position corresponding to position 160 of SEQ ID NO:2;
x. a leucine residue at the position corresponding to position 161 of SEQ ID NO:2;
y. an arginine residue at the position corresponding to position 163 of SEQ ID NO:2
z. a leucine residue at the position corresponding to position 165 of SEQ ID NO:2;
aa. a threonine residue at the position corresponding to position 166 of SEQ ID NO:2;
bb. an alanine residue at the position corresponding to position 173 of SEQ ID NO:2; and
cc. a cysteine residue at the position corresponding to position 178 of SEQ ID NO:2.

In one embodiment the isolated protein comprises at least 1, 2, 3, 4, 5, 6, 7, 8, 9, 10, 11, 12, 13, 14, 15, 16, 17, 18, 19, 20, 21, 22, 23, 24, 25, 26, 27, 28 or 29 of any of sequence elements a-cc.

In one embodiment, the isolated protein comprises an amino acid sequence at least 85% identical, at least 90% identical, at least 92% identical, at least 94% identical, at least 96% identical or at least 98% identical over its entire length to SEQ ID NO:2, wherein the isolated protein comprises:
a. a cysteine residue at the position corresponding to position 27 of SEQ ID NO:2;
b. an leucine residue at the position corresponding to position 29 of SEQ ID NO:2
c. a serine residue at the position corresponding to position 30 of SEQ ID NO:2
d. a tyrosine residue at the position corresponding to position 32 of SEQ ID NO:2
e. a serine residue at the position corresponding to position 34 of SEQ ID NO:2
f. a proline residue at the position corresponding to position 37 of SEQ ID NO:2;
g. a leucine residue at the position corresponding to position 40 of SEQ ID NO:2;
h. an alanine residue at the position corresponding to position 42 of SEQ ID NO:2;
i. a lysine residue at the position corresponding to position 44 of SEQ ID NO:2;
j. an aspartic acid residue at the position corresponding to position 48 of SEQ ID NO:2;
k. a tyrosine residue at the position corresponding to position 50 of SEQ ID NO:2;
l. a glutamic acid residue at the position corresponding to position 51 of SEQ ID NO:2;
m. a cysteine residue at the position corresponding to position 62 of SEQ ID NO:2;
n. a cysteine residue at the position corresponding to position 76 of SEQ ID NO:2;
o. an alanine residue at the position corresponding to position 87 of SEQ ID NO:2;
p. a leucine residue at the position corresponding to position 111 of SEQ ID NO:2;
q. a leucine residue at the position corresponding to position 112 of SEQ ID NO:2;
r. an aspartic acid residue at the position corresponding to position 118 of SEQ ID NO:2;
s. an alanine residue at the position corresponding to position 120 of SEQ ID NO:2;
t. a cysteine residue at the position corresponding to position 122 of SEQ ID NO:2;
u. a cysteine residue at the position corresponding to position 152 of SEQ ID NO:2;
v. a valine residue at the position corresponding to position 157 of SEQ ID NO:2;
w. an asparagine residue at the position corresponding to position 160 of SEQ IDNO:2;
x. a leucine residue at the position corresponding to position 161 of SEQ ID NO:2;
y. an arginine residue at the position corresponding to position 163 of SEQ ID NO:2
z. a leucine residue at the position corresponding to position 165 of SEQ ID NO:2;
aa. a threonine residue at the position corresponding to position 166 of SEQ ID NO:2;
bb. an alanine residue at the position corresponding to position 173 of SEQ ID NO:2; and
cc. a cysteine residue at the position corresponding to position 178 of SEQ ID NO:2.

As noted above, IFNL4 proteins of the present invention have particular activities that make them useful tools for diagnosing, and developing treatments for individuals infected with HCV and individuals at risk for such infection. Examples of such activity include:
1) the ability to elicit an antibody that selectively binds a protein consisting of SEQ ID NO:2;
2) selectively binding an antibody generated against a protein consisting of SEQ ID NO:2;
3) selectively binding a compound that binds to a protein consisting of SEQ ID NO:2, and;
4) the ability of IFNL4 to induce the JAK/STAT pathway.

Methods of measuring induction of the JAK/STAT pathway are known to those skilled in the art. One such method is an assay based on the ability of IFNL4 protein to stimulate expression of interferon stimulated genes (ISGs).

In one embodiment, an isolated protein of the present invention is able to elicit an antibody that selectively binds to a protein consisting of SEQ ID NO:2. In one embodiment, a specific mouse anti-IFNL4 antibody was raised to recognize a synthetic peptide corresponding to amino acids 44-74 of human IFNL4. The specific detection by Western blot was demonstrated using recombinant purified IFNL4 protein (FIG. 8) and confocal imaging of HepG2 cells transiently transfected with IFNL4-Halo construct, and primary human hepatocytes from an individual heterozygous for ss469415590 activated by treatment with PolyI:C or by in-vitro infection of HCV (FIG. 9) Thus, embodiments of the invention include antibodies that specifically recognize and bind to the IFNL4 protein, or fragments thereof (FIG. 11). In a specific embodiment, the antibodies may be monoclonal antibodies, raised in the mouse or rabbit.

In one embodiment, an isolated protein of the present invention is able to bind a compound that binds to a protein consisting of SEQ ID NO:2. In one embodiment, an isolated protein of the present invention is able to induce the JAK/STAT pathway.

As used herein, the phrase without significantly affecting the activity of a protein means that the variant has at least 80%, at least 90% or at least 95% of the activity of a protein consisting of SEQ ID NO:2. Thus, in one embodiment, the isolated protein has at least 80%, at least 90% or at least 95% of the activity of a protein consisting of SEQ ID NO:2. In one embodiment, the isolated protein has at least 98% of the activity of a protein consisting of SEQ ID NO:2. In some cases, variations in the amino acid sequence of the isolated protein will increase the activity of the protein. Thus, one embodiment of the present invention is an isolated protein that has at least 1.25×, at least 1.5×, at least 1.75×, at last 2×, at last 4×, at least 6×, at least 8× or at least 10× the level of activity of a protein consisting of SEQ ID NO:2. The measurement and comparison of such activities can be accomplished using methods known in the art. For example, the ability to elicit an antibody to a protein is generally accomplished by immunizing an animal (e.g., a mouse) with an isolated protein of the present invention, and then testing the resulting antibodies for their ability to selectively bind a protein, such as a protein consisting of SEQ ID NO:2. As used herein, the terms selectively, selective, specific, and the like, indicate the antibody has a greater affinity for an isolated IFNL4 protein than it does for proteins unrelated to IFNL4. More specifically, the terms selectively, selective, specific, and the like indicate that the affinity of the antibody for an isolated IFNL4 protein is statistically significantly higher than its affinity for a negative control (e.g., an unrelated protein, such as, for example, albumin) as measured using a standard assay (e.g., ELISA). Likewise, similar techniques, known to those skilled in the art, exist for measuring the ability of a compound to bind IFNL4 proteins of the present invention.

In addition to testing for the ability to elicit an antibody, IFNL4 proteins of the present invention can be tested for their ability to activate the JAK/STAT pathway. Such assays are generally performed by measuring the activity of components of the JAK/STAT system. For example, luciferase assays may be used to measure activity of a reporter gene that serves as a measure of JAK/STAT activity. In these assays, the luciferase protein is used as a reporter gene under regulation of an interferon-stimulated responsive element (ISRE) Among 45 human signaling pathways tested, only the ISRE-Luc and IRF3-Luc reporters were activated by type I and III interferons (IFN-a and IFNL3) and a transiently transfected expression construct for IFNL4, but not purified recombinant IFNL4 protein or expression constructs for other protein isoforms (FIG. 12). This was validated by an individual ISRE-Luc assay in HepG2 cells transiently or stably transfected with ISRE-Luc (FIG. 13). IFNL4 also showed anti-viral response in a specific experiment in a Huh7 cell line expressing Luciferase reporter linked with a subgenomic HCV replicon (FIG. 13). In another embodiment, protein activity (measured for example by Western blot) of JAK/STAT pathway protein components may be measured. For example, tyrosine phosphorylation of STAT1 protein may be measured by Western blot as an indicator of the activity of the cytokine receptor signaling pathways. In another embodiment, the activity of the JAK/STAT pathway may be measured by the expression level of interferon stimulated genes, ISGs, i.e., measurement of gene expression levels of genes directly or indirectly stimulated by interferons, resulting in activation of the JAK/STAT pathway. Only transiently transfected IFNL4, but not other protein isoforms, caused STAT1 and STAT2 phosphorylation, similar to that caused by IFNL3 (FIG. 14).

Suitable techniques for assaying for the IFNL4 protein biological activities are disclosed herein and are known to those skilled in the art. Such assays can be in vitro or in vivo assays. Examples of useful assays include, but are not limited to, an enzyme-linked immunoassay, a competitive enzyme-linked immunoassay, a radioimmunoassay, a fluorescence immunoassay, a chemiluminescent assay, a lateral flow assay, a flow-through assay, an agglutination assay, a particulate-based assay (e.g., using particulates such as, but not limited to, magnetic particles or plastic polymers, such as latex or polystyrene beads), an immunoprecipitation assay, an immunoblot assay (e.g., a western blot), a phosphorescence assay, a flow-through assay, a chromatography assay, a polyacrylamide gel electrophoresis (PAGE)-based assay, a surface plasmon resonance assay, a spectrophotometric assay, a particulate-based assay, an electronic sensory assay and a flow cytometric assay. Methods of performing such assays are well known to those skilled in the art. Assays can be designed to give qualitative, quantitative or semi-quantitative results, depending on how they are used and the type of result that is desired.

While isolated proteins of the present invention can consist entirely of the sequences disclosed herein, and the disclosed variants thereof, such proteins may additionally contain amino acid sequences that do not confer IFNL4 activity, but which have other useful functions. Any useful, additional amino acid sequence can be added to the isolated protein sequence, so long as the additional sequences do not have an unwanted effect on the protein's ability to elicit an antibody to a protein consisting of SEQ ID NO:2, selectively bind an antibody that selectively binds to a protein consisting of SEQ ID NO:2, bind a compound that binds to a protein consisting of SEQ ID NO:2, or activate expression of the JAK/STAT pathway. For example, isolated proteins of the present invention can contain amino acid sequences that are useful for visualizing or purifying the peptide. Such sequences act as labels (e.g., enzymes) or tags (antibody binding sites). Examples of such labels and tags include, but are not limited to, β-galactosidase, luciferase, glutathione-s-transferase, thioredoxin, HIS-tags, biotin tags, and fluorescent tags. Other useful sequences for labeling and tagging proteins are known to those of skill in the art.

In addition to the modifications described above, isolated proteins of the present invention can be further modified, so long as such modification does not significantly affect the ability of the protein to elicit an antibody to a protein consisting of SEQ ID NO:2, selectively bind an antibody that selectively binds to a protein consisting of SEQ ID NO:2, bind a compound that binds to a protein consisting of SEQ ID NO:2, or activate expression of the JAK/STAT pathway. Such modifications can be made, for example, to increase the stability, solubility or absorbability of the protein. Examples of such modifications include, but are not limited to pegylation, glycosylation, phosphorylation, acetylation, myristylation, palmitoylation, amidation and/or other chemical modification of the peptide.

Isolated proteins of the present invention can be obtained from nature (e.g., obtained from plants, animals or microorganisms) or they can be produced in a laboratory (e.g., recombinantly or synthetically). Also encompassed are peptides that are combinations of natural and synthetic molecules. General methods for producing and isolating recombinant or synthetic peptides are known to those skilled in the art.

Proteins of the present invention are encoded by isolated nucleic acid molecules of the present invention. In accordance with the present invention, an isolated nucleic acid molecule is one that has been removed from its natural milieu (i.e., that has been subject to human manipulation). As such, isolated does not reflect the extent to which the nucleic acid molecule has been purified. An isolated nucleic acid molecule of the present invention can be obtained from its natural source either as an entire (i.e., complete) gene, or as some portion thereof that encodes an isolated protein of the present invention. Alternatively, an isolated nucleic acid molecule of the present invention can be obtained through synthesis (e.g., chemical synthesis, solid-phase synthesis, polymerase chain reaction). Further, isolated nucleic acid molecules of the present invention can be a combination of molecules obtained from a natural source, and molecules obtained through synthesis (e.g., cloning of genome fragments encoding an isolated protein of the present invention). In addition, an isolated nucleic acid molecule of the present invention can include DNA, RNA or derivatives thereof.

An isolated nucleic acid molecule of the present invention can be produced using a number of methods known to those skilled in the art (see, for example, Sambrook et al., *Molecular Cloning: A Laboratory Manual, Third Edition*, 2001, which is incorporated herein by reference in its entirety). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule variants can be selected from a mixture of modified nucleic acids by screening for the function of the protein encoded by the nucleic acid (e.g., the ability of the protein to ability to elicit an antibody to a protein consisting of SEQ ID NO:2, bind a compound that binds to a protein consisting of SEQ ID NO:2, or activate expression of the JAK/STAT pathway). Such screening methods have been described herein and are routinely performed by those skilled in the art.

Thus, one embodiment of the present invention is a nucleic acid molecule comprising a nucleic acid sequence that encodes an isolated protein comprising at least about 30 contiguous amino acids, at least about 40 contiguous amino acids, at least about 50 contiguous amino acids, at least about 60 contiguous amino acids, at least about 70 contiguous amino acids, at least about 80 contiguous amino acids, at least about 90 contiguous amino acids, or at least about 100 contiguous amino acids from an amino acid sequence selected from the group consisting of SEQ ID NO:2, SEQ ID NO:5 and SEQ ID NO:8. In one embodiment, the isolated nucleic acid molecule comprise a nucleic acid sequence that encodes an isolated protein comprising at least about 110 contiguous amino acids, at least about 120 contiguous amino acids, or an at least about 130 contiguous amino acids from an amino acid selected from the group consisting of SEQ IDNO:2 and SEQ ID NO:5. In one embodiment, the isolated nucleic acid molecule comprise a nucleic acid sequence that encodes an isolated protein comprising at least about 140 contiguous amino acids or at least about 150 contiguous amino acids from SEQ ID NO:2. In one embodiment, the isolated nucleic acid molecule comprises at least 90, 100, 125, 150, 175, 200, 250, 300, 350, 400, 450, or 500 contiguous nucleotides from a nucleic acid sequence selected form the group consisting of SEQ ID NO:1, SEQ ID NO:4 and SEQ ID NO:7. Also encompassed are nucleic acid molecules comprising nucleic acid sequences fully complementary to nucleic acid sequences present in nucleic acid molecules of the present invention. Thus, one embodiment of the present invention is an isolated nucleic acid molecule comprising at least 90, 100, 125, 150, 175, 200, 250, 300, 350, 400, 450, or 500 contiguous nucleotides from a nucleic acid sequence selected form the group consisting of SEQ ID NO:3, SEQ ID NO:6 and SEQ ID NO:8.

As has been discussed, the present invention encompasses variants of proteins comprising the sequence of SEQ ID NO:2, SEQ ID NO:5, or SEQ ID NO:8. Thus, one embodiment of the present invention is an isolated nucleic acid molecule that encodes a protein comprising a sequence of at least 50 contiguous amino acids, wherein the at least 50 contiguous amino acid sequence is at least 92% identical, at least 94% identical, at least 96% identical or at least 98% identical over its entire length to an at least 50 contiguous amino acid sequence from SEQ ID NO:2, SEQ ID NO:5 or SEQ ID NO:8. In a further embodiment, the isolated nucleic acid molecule encodes a protein comprising a sequence of at least 100 contiguous amino acids, wherein the at least 100 contiguous amino acid sequence is at least 92% identical, at least 94% identical, at least 96% identical or at least 98% identical over its entire length to an at least 100 contiguous amino acid sequence from SEQ ID NO:2, SEQ ID NO:5 or SEQ ID NO:8. In yet a further embodiment, the isolated nucleic acid molecule encodes a protein comprising a sequence of at least 150 contiguous amino acids, wherein the at least 150 contiguous amino acid sequence is at least 92% identical, at least 94% identical, at least 96% identical or at least 98% identical over its entire length to an at least 150 contiguous amino acid sequence from SEQ ID NO:2. In one embodiment, the isolated nucleic acid molecule encodes a protein comprising an amino acid sequence at least 92% identical, at least 94% identical, at least 96% identical or at least 98% identical over the entire length of an amino acid sequence selected from the group consisting of SEQ ID NO:2, SEQ ID NO:5 and SEQ ID NO:8. In one embodiment, the isolated nucleic acid molecule comprises at least 90, at least 100, at least 125, at least 150, at least 175, at least 200, at least 250, at least 300, at least 350, at least 400, at least 450, or at least 500 contiguous nucleotides that are at least 90%, at least 92%, at least 94%, at least 96% or at least 98% identical over their entire length to at least 90, at least 100, at least 125, at least 150, at least 175, at least 200, at least 250, at least 300, at least 350, at least 400, at least 450, or at least 500 contiguous nucleotides from a nucleic acid sequence selected form the group consisting of SEQ ID NO:1, SEQ ID NO:4 and SEQ ID NO:7. In various embodiments, the isolated nucleic acid molecules encode proteins comprising the conserved amino acids disclosed herein.

The present invention also includes nucleic acid molecules that are oligonucleotides capable of hybridizing, under stringent conditions, with complementary regions of other, preferably longer, nucleic acid molecules of the present invention that encode at least a portion of an IFNL4 protein, or variants thereof. A preferred oligonucleotide is capable of hybridizing, under stringent conditions, with a nucleic acid molecule that is capable of encoding a protein comprising at least 30 contiguous amino acids from SEQ ID NO:2, or a variant protein thereof. Certain preferred oligonucleotides are capable of hybridizing to nucleic acid molecules comprising at least 90, 100, 125, 150, 175, 200, 250, 300, 350, 400, 450, or 500 contiguous nucleotides from a nucleic acid sequence selected from the group consisting of SEQ ID NO:1, SEQ ID NO:4 and SEQ ID NO:7, or complements thereof. Preferred oligonucleotides are those having at least 92%, at least 94%, at least 96% or at least 98% identity over their entire length with at least a portion of SEQ ID NO:1, SEQ ID NO:3, SEQ ID NO:4, SEQ ID NO:6, SEQ ID NO:7 or SEQ ID NO:9.

Oligonucleotides of the present invention can be RNA, DNA, or derivatives of either. The minimal size of such oligonucleotides is the size required to form a stable hybrid between a given oligonucleotide and the complementary sequence on another nucleic acid molecule of the present invention. The size of the oligonucleotide must also be sufficient for the use of the oligonucleotide in accordance with the present invention. Oligonucleotides of the present invention can be used in a variety of applications including, but not limited to, as probes to identify additional nucleic acid molecules, as primers to amplify or extend nucleic acid molecules or in therapeutic applications to inhibit, for example, expression of IFNL4 protein. Such therapeutic applications include the use of such oligonucleotides in, for example, antisense, triplex formation, ribozyme and/or RNA drug-based technologies. Such technologies are known to those skilled in the art. The present invention, therefore, includes such oligonucleotides and methods to interfere with the production of IFNL4 proteins by use of one or more of such technologies.

The present invention also includes recombinant constructs, which comprise nucleic acid molecule of the present invention inserted into any vector capable of delivering the nucleic acid molecule into a host cell. Such a construct contains heterologous nucleic acid sequences, that is nucleic acid sequences that are not naturally found adjacent to IFNL4 protein encoding nucleic acid molecules of the present invention. The vector can be either RNA or DNA, either prokaryotic or eukaryotic, and typically is a virus or a plasmid. Recombinant vectors can be used in the cloning, sequencing, and/or otherwise manipulating of IFNL4 protein and/or IFNL4 nucleic acid molecules of the present invention. One type of recombinant construct herein referred to as a recombinant molecule and described in more detail below, can be used in the expression of nucleic acid molecules of the present invention. Preferred recombinant vectors are capable of replicating in the transformed cell lines.

A preferred nucleic acid molecule to include in a recombinant vector of the present invention is a nucleic acid molecule that encodes at least a portion of at least one IFNL4 protein of the present invention, or variants thereof. A specific nucleic acid molecule to include in a recombinant vector is a nucleic acid molecules encoding at least about 30 contiguous amino acids, at least about 40 contiguous amino acids, at least about 50 contiguous amino acids, at least about 60 contiguous amino acids, at least about 70 contiguous amino acids, at least about 80 contiguous amino acids, at least about 90 contiguous amino acids, or at least about 100 contiguous amino acids from an amino acid sequence selected from the group consisting of SEQ ID NO:2, SEQ ID NO:5 and SEQ ID NO:8, or variants thereof. As such, also included are nucleic acid molecules comprising at least 90, 100, 125, 150, 175, 200, 250, 300, 350, 400, 450, or 500 contiguous nucleotides from a nucleic acid sequence selected from the group consisting of SEQ ID NO:1, SEQ ID NO:4 and SEQ ID NO:7, complements thereof, and variants thereof.

In one embodiment, an IFNL4 protein of the present invention is produced by culturing a cell capable of expressing the protein under conditions effective to produce the protein, and recovering the protein. A preferred cell to culture is a recombinant cell that is capable of expressing the IFNL4 protein, the recombinant cell being produced by transforming a host cell with one or more nucleic acid molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Nucleic acid molecules with which to transform a host cell are as disclosed herein for including in recombinant vectors of the present invention.

Suitable host cells to transform include any cell that can be transformed and that can express the introduced IFNL4 protein. Such cells are, therefore, capable of producing IFNL4 proteins of the present invention after being transformed with at least one nucleic acid molecule of the present invention. Host cells can be either untransformed cells or cells that are already transformed with at least one nucleic acid molecule. Suitable host cells of the present invention can include bacterial, fungal (including yeast), insect, animal and plant cells. Preferred host cells include bacterial, yeast, insect and mammalian cells, with bacterial (e.g., *E. coli*) and insect (e.g., *Spodoptera*) cells being particularly preferred.

A recombinant cell is preferably produced by transforming a host cell with one or more recombinant molecules, each comprising one or more nucleic acid molecules of the present invention operatively linked to an expression vector containing one or more transcription control sequences. The phrase "operatively linked" refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, insect, animal, and/or plant cells. As such, nucleic acid molecules of the present invention can be operatively linked to expression vectors containing regulatory sequences such as promoters, operators, repressors, enhancers, termination sequences, origins of replication, and other regulatory sequences that are compatible with the recombinant cell and that control the expression of nucleic acid molecules of the present invention. As used herein, a transcription control sequence includes a sequence which is capable of controlling the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, helminth, insect and mammalian cells, such as, but not limited to, tac, lac, trp, trc, oxy-pro, omp/lpp, rrnB, bacteriophage lambda ($\lambda$) (such as $\lambda p_L$ and $\lambda p_R$ and fusions that include such promoters), bacteriophage T7, T7 lac, bacteriophage T3, bacteriophage SP6, bacteriophage SP01, metallothionein, alpha mating factor, *Pichia* alcohol oxidase, alphavirus subgenomic promoters (such as Sindbis virus subgenomic promoters), baculovirus, *Heliothis zea* insect virus, vaccinia virus, herpesvirus, poxvirus, adenovirus, simian virus 40, retrovirus actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with a DNA sequence encoding an IFNL4 protein.

Expression vectors of the present invention may also contain secretory signals (i.e., signal segment nucleic acid sequences) to enable an expressed protein to be secreted from the cell, or any heterologous signal segment capable of directing the secretion of an IFNL4 protein, including fusion proteins, of the present invention. Preferred signal segments include, but are not limited to, tissue plasminogen activator (t-PA), interferon, interleukin, growth hormone, histocompatibility and viral envelope glycoprotein signal segments.

Expression vectors of the present invention may also contain fusion sequences which lead to the expression of inserted nucleic acid molecules of the present invention as fusion proteins. Inclusion of a fusion sequence as part of a nucleic acid molecule of the present invention can enhance the stability during production, storage and/or use of the protein encoded by the nucleic acid molecule. Furthermore, a fusion segment can function as a tool to simplify purification of an IFNL4 protein, such as to enable purification of the resultant fusion protein using affinity chromatography. A suitable fusion segment can be a domain of any size that has the desired function (e.g., increased stability and/or purification tool). It is within the scope of the present invention to use one or more fusion segments. Fusion segments can be joined to amino and/or carboxyl termini of an IFNL4 protein. Linkages between fusion segments and IFNL4 proteins can be constructed to be susceptible to cleavage to enable straight-forward recovery of the IFNL4 proteins. Fusion proteins are preferably produced by culturing a recombinant cell transformed with a fusion nucleic acid sequence that encodes a protein including the fusion segment attached to either the carboxyl and/or amino terminal end of an IFNL4 protein.

A recombinant molecule of the present invention is a molecule that can include at least one of any nucleic acid molecule heretofore described operatively linked to at least one of any transcription control sequence capable of effectively regulating expression of the nucleic acid molecule(s) in the cell to be transformed. A preferred recombinant molecule includes one or more nucleic acid molecules that encode at least about 30 contiguous amino acids, at least about 40 contiguous amino acids, at least about 50 contiguous amino acids, at least about 60 contiguous amino acids, at least about 70 contiguous amino acids, at least about 80 contiguous amino acids, at least about 90 contiguous amino acids, or at least about 100 contiguous amino acids from an amino acid sequence selected from the group consisting of SEQ ID NO:2, SEQ ID NO:5 and SEQ ID NO:8, or variants thereof. Particularly preferred nucleic acid molecules to include in a recombinant molecule are as disclosed herein for including in a recombinant vector of the present invention.

A recombinant cell of the present invention includes any cells transformed with at least one of any nucleic acid molecules of the present invention. A preferred recombinant cell is a cell transformed with at least one nucleic acid molecule that encodes at least about 30 contiguous amino acids, at least about 40 contiguous amino acids, at least about 50 contiguous amino acids, at least about 60 contiguous amino acids, at least about 70 contiguous amino acids, at least about 80 contiguous amino acids, at least about 90 contiguous amino acids, or at least about 100 contiguous amino acids from an amino acid sequence selected from the group consisting of SEQ ID NO:2, SEQ ID NO:5 and SEQ ID NO:8, or variants thereof.

It will be appreciated by those skilled in the art that use of recombinant DNA technologies can improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant protein production during fermentation. The activity of an expressed recombinant protein of the present invention may be improved by fragmenting, modifying, or derivatizing the resultant protein.

In accordance with the present invention, recombinant cells can be used to produce an IFNL4 protein of the present invention by culturing such cells under conditions effective to produce such a protein, and recovering the protein. Effective conditions to produce a protein include, but are not limited to, appropriate media, bioreactor, temperature, pH and oxygen conditions that permit protein production. An appropriate, or effective, medium refers to any medium in which a cell of the present invention, when cultured, is capable of producing an IFNL4 protein. Such a medium is typically an aqueous medium comprising assimilable carbohydrate, nitrogen and phosphate sources, as well as appropriate salts, minerals, metals and other nutrients, such as vitamins. The medium may comprise complex nutrients or may be a defined minimal medium.

Cells of the present invention can be cultured in conventional fermentation bioreactors, which include, but are not limited to, batch, fed-batch, cell recycle, and continuous fermentors. Culturing can also be conducted in shake flasks, test tubes, microtiter dishes, and petri plates. Culturing is carried out at a temperature, pH and oxygen content appropriate for the recombinant cell. Such culturing conditions are well within the expertise of one of ordinary skill in the art.

Depending on the vector and host system used for production, resultant IFNL4 proteins may either remain within the recombinant cell; be secreted into the fermentation medium; be secreted into a space between two cellular membranes, such as the periplasmic space in *E. coli*; or be retained on the outer surface of a cell or viral membrane. The phrase "recovering the protein" refers simply to collecting the whole fermentation medium containing the protein and need not imply additional steps of separation or purification. IFNL4 proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, chromatofocusing and differential solubilization.

The present invention also includes isolated (i.e., removed from their natural milieu) antibodies that selectively bind to isolated IFNL4 proteins of the present invention and/or IFNL4 proteins present in an individual or a sample from an individual. Isolated antibodies of the present invention can include antibodies in serum, or antibodies that have been purified to varying degrees. Antibodies of the present invention can be polyclonal or monoclonal, or can be functional equivalents such as antibody fragments and genetically-engineered antibodies, including single chain antibodies or chimeric antibodies that can bind to one or more epitopes on IFNL4 proteins of the present invention. A suitable method to produce antibodies effective for use in the present invention includes (a) administering to an animal an effective amount of an IFNL4 protein, or fragment thereof, to produce the antibodies and (b) recovering the antibodies. Antibodies raised against defined proteins or fragments can be advantageous because such antibodies are not substantially contaminated with antibodies against other substances that might otherwise cause interference in a diagnostic assay. Methods to produce such antibodies are known in the art and are described in detail in Harlow et al., Antibodies, a Laboratory Manual (Cold Spring Harbor Labs Press, 1988), and include immunizing animals to produce preparations of polyclonal antibodies that are recovered from, for example, ascites fluid and purified by methods known in the art to yield preparations that are reactive to IFNL4 protein. Many species have proteins sharing related sequences and therefore it may be difficult using standard immunization protocols to produce antibodies that recognize a protein from only one specie. Therefore, modification of standard methods used to produce antibodies, such as, for example, subtractive hybridization techniques, are also contemplated. Such modifications are known to those skilled in the art. In another method, antibodies for use in the present invention are produced recombinantly using techniques disclosed in Sambrook et al., Molecular Cloning: A Laboratory Manual, (Cold Spring Harbor Labs Press, 1989).

One embodiment of the present invention is an antibody that selectively binds to a variant of an IFNL4 protein. In one embodiment, the antibody selectively binds a variant selected from the group consisting of Cys17Tyr), Arg60Pro) and Pro70Ser).

Other suitable methods include producing monoclonal antibodies. Briefly, monoclonal antibodies are produced from the fusion of spleen cells from an immunized animal and myeloma cells to produce a hybridoma. Hybridomas can be screened for production of the proper antibody, then cultured and the antibodies harvested. Methods to produce and screen such hybridomas are known to those skilled in the art and are described in Harlow, et al., supra. Moreover, methods to prepare an antigen so that antibodies produced will be reactive with IFNL4 protein are known in the art and are described, for example, in Harlow, et al., supra. Preparation of the antigen material for injection into the animal includes any technique known in the art, and include, for example, using the full-length protein, using peptides selected from immunogenic regions of the protein, modifying the antigen by methods such as, for example, dinitrophenol coupling, arsynyl coupling, denaturation of the antigen, coupling antigen to protein carriers such as, for example, keyhole limpet hemacyanin, peptides containing Class II-T-cell receptor binding sites, to beads, and any other method known in the art. See Harlow, et al., supra.

Antibodies of the present invention can include multi-functional antibodies, for example a bifunctional antibody having at least one functional portion that specifically binds to an IFNL4 protein. Such multifunctional antibodies can include, for example, a chimeric molecule comprising a portion of the molecule that binds to an IFNL4 protein and a second portion that enables the chimeric molecule to be bound to a substrate or to be detected in such a manner that the binding to the IFNL4 protein is unimpaired. Examples of suitable second portions include, but are not limited to, a fragment of an immunoglobulin molecule, a fluorescent protein or an enzyme.

An antibody used in the present invention can be contained in a formulation. For example, an antibody can be combined with a buffer in which the antibody is solubilized, and/or with a carrier. Suitable buffers and carriers are known to those skilled in the art. Examples of suitable buffers include any buffer in which an antibody can function to selectively bind to an IFNL4 protein, such as, but not limited to, phosphate buffered saline, water, saline, phosphate buffer, HEPES buffer (N-2-hydroxyethylpiperazine-N'-2-ethansulfonic acid buffered saline) TES buffer (Tris-EDTA buffered saline), Tris buffer and TAE buffer (Tris-acetate-EDTA). Examples of carriers include, but are not limited to, polymeric matrices, toxoids, and serum albumins, such as bovine serum albumin. Carriers can be combined with an antibody or conjugated (i.e. attached) to an antibody in such a manner as to not substantially interfere with the ability of the antibody to selectively bind to an IFNL4 protein.

As has been described, IFNL4 protein is produced as a result of an individual carrying a specific allele (i.e., the deletion allele) of the ss469415590 polymorphism. As has also been described, the inventors have previously discovered that carrying at least one deletion allele of the ss469415590 polymorphism increases the likelihood that an individual will be unable to spontaneously clear an HCV infection, and the likelihood that the individual will fail to respond to treatment of an HCV infection (as described in U.S. Provisional Application No. 61/543,620, now International Application No. PCT/US12/59048, filed Oct. 5, 2012). Thus, the presence, absence and/or level of IFNL4 protein present in an individual can be used to determine the likelihood that the individual will spontaneously clear an HCV infection and/or the likelihood the individual will respond to treatment for an HCV infection.

Accordingly, one embodiment of the present invention is a method for predicting the likelihood of an individual to spontaneously clear an HCV infection by analyzing a biological sample from an individual to determine the presence or absence of an IFNL4 protein of the present invention in the sample. The presence of an IFNL4 protein of the present invention in sample indicates that the individual is less likely to spontaneously clear an HCV infection.

In one embodiment, the absence of IFNL4 protein in the sample indicates the individual is predicted to be more likely to spontaneously clear an HCV infection. In one embodiment, the presence of IFNL4 protein in the sample indicates that the individual is predicted to be less likely to spontaneously clear an HCV infection.

Another embodiment of the present invention is a method for predicting the likelihood that an individual will respond to a treatment for HCV infection, by analyzing a biological sample from an individual to determine the presence or absence of an IFNL4 protein of the present invention in the individual. The presence of an IFNL4 protein of the present invention indicates the likelihood that the individual will not respond to treatment for an HCV infection, or benefit from the administration of a treatment for an HCV infection.

In one embodiment, the absence of IFNL4 protein in the sample indicates the individual is predicted to be more likely to respond to treatment for an HCV infection. In one embodiment, the presence of IFNL4 protein in the sample indicates that the individual is predicted to be less likely to respond to treatment for an HCV infection.

As has been described, the IFNL4 protein is encoded by a gene on human chromosome 19. It will be appreciated by those skilled in the art that because mammals have pairs of chromosomes, they have two copies of this gene, the sequences of which are not necessarily identical. That is, while this region on one chromosome may contain one allele of a polymorphism (e.g., rs67272382), the same region of the other chromosome may contain the same or a different allele of that polymorphism. In instances where two loci in an individual contain different sequences (e.g. an allele and the wild-type sequence, two different alleles), the individual is referred to as being heterozygous for that loci. In instances where two loci in an individual contain the same sequence (e.g., both contain the same allele), the individual is referred to as being homozygous for that loci. The presence of one copy of a polymorphism can have a different affect on the likelihood of spontaneously clearing an HCV infection, or responding to an HCV treatment, than the presence of two copies of the same polymorphism. For example, if both chromosomes contain the insertion allele (and therefore lack the deletion allele) the individual will not produce the IFNL4 protein. However, if one chromosome contains the insertion allele, and the sister chromosome contains the deletion allele, the individual will produce some amount of IFNL4 protein. Finally, if an individual has two copies of the deletion allele, such an individual may produce more IFNL4 protein than does an individual that is heterozygous for that allele. Consequently, an individual who has two copies of the insertion allele is more likely to spontaneously clear an HCV infection, or respond to a treatment for HCV infection, than is an individual who only has one copy of such an allele. Likewise, an individual who has one copy of an insertion allele and one copy of a deletion allele is more likely to spontaneously clear an HCV infection, or respond to treatment for HCV, than is an individual who has two copies of the deletion allele.

In one embodiment, an individual who is heterozygous for an insertion allele of the present invention is more likely to clear an HCV infection, or respond to an HCV treatment, than is an individual who does not carry such an allele. In another embodiment, an individual who is homozygous for an insertion allele of the present invention is more likely to clear an HCV infection, or respond to an HCV treatment, than is an individual who is heterozygous for such an allele. In one embodiment, an individual who is heterozygous for a deletion allele of the present invention is less likely to spontaneously clear an HCV infection, or respond to treatment for an HCV infection, than is an individual who does not carry any deletion alleles of the present invention. In another embodiment, an individual who is homozygous for a deletion allele of the present invention is even less likely to spontaneously clear an HCV infection, or respond to treatment for an HCV infection, than is an individual who is heterozygous for a deletion allele of the present invention.

Accordingly, one embodiment of the present invention is a method for predicting the likelihood of an individual to spontaneously clear an HCV infection, by analyzing a biological sample from an individual to determine the level of IFNL4 mRNA or protein present in the sample, if any. The level of IFNL4 protein present in the sample is indicative of the likelihood the individual to spontaneously clear an HCV infection.

Another embodiment of the present invention is a method for predicting the likelihood of an individual to respond to treatment for an HCV infection by analyzing a biological sample from individual in order to determine the level of IFNL4 mRNA or protein present in the sample, if any. The level of IFNL4 protein present in the sample is indicative of the likelihood that the individual to respond to a treatment for an HCV infection.

The terms individual, subject, and patient are well-recognized in the art, and are herein used interchangeably to refer to a mammal, including dog, cat, rat, mouse, monkey, cow, horse, goat, sheep, pig, camel, and, most preferably, a human. In some embodiments, the subject is in need of a hepatitis C treatment. For example, in one embodiment the subject is infected with HCV. However, in other embodiments, the subject is not infected with HCV. In one embodiment, the subject is at risk for infection with HCV. In one embodiment, the subject has been exposed to HCV. As used herein, the terms exposed, exposure, and the like, indicate the subject has come in contact with bodily fluid from another individual who is infected with HCV. Contact can occur through such things as, for example, a needle stick, sexual contact, or the birthing process.

The terms individual, subject, and patient by themselves do not denote a particular age, sex, race, and the like. Thus, individuals of any age, whether male or female, are intended to be covered by the present disclosure. Likewise, the methods of the present invention can be applied to any race, including, for example, Caucasian (white), African-American (black), Native American, Native Hawaiian, Hispanic, Latino, Asian, and European. In some embodiments of the present invention, such characteristics are significant. In such cases, the significant characteristic(s) (age, sex, race, etc.) will be indicated.

The term hepatitis C virus, or HCV, is used herein to define an RNA viral species of which pathogenic strains cause hepatitis C, also known as non-A, non-B hepatitis. Based on genetic differences between HCV isolates, the hepatitis C virus species is classified into six major genotypes (1-6) with several subtypes within each genotype. Subtypes are further broken down into quasi species based on their genetic diversity. The preponderance and distribution of HCV genotypes varies globally. For example, in North America, genotype 1a predominates followed by 1b, 2a, 2b, and 3a. In Europe, genotype 1b is predominant followed by 2a, 2b, 2c, and 3a. Genotypes 4 and 5 are found almost exclusively in Africa. The viral genotype may be clinically important in determining potential response to interferon-based therapy and the required duration of such therapy. Genotypes 1 and 4 are generally less responsive to interferon-based treatment than are the other genotypes (2, 3, 5 and 6). It is to be noted that genotypes 5 and 6 are rare in the U.S. population.

As used herein, hepatitis C is an infectious disease affecting the liver, which is caused by the hepatitis C virus (HCV). The initial infection with HCV may produce acute symptoms or the individual may be asymptomatic (without symptoms), but once established, chronic hepatitis C infection can progress to scarring of the liver (fibrosis), and advanced scarring (cirrhosis) which is generally apparent after many years. In some cases, those with chronic hepatitis C will go on to develop liver failure or other complications of chronic hepatitis C, including liver cancer.

According to the present invention, chronic hepatitis C refers to an infection with HCV that persists for more than six months. Clinically, it is often asymptomatic and it is often discovered accidentally. The natural course of chronic hepatitis C varies considerably from one person to another. Although almost all people infected with HCV have evidence of inflammation on liver biopsy, the rate of progression of liver scarring (fibrosis) shows significant variability among individuals. Accurate estimates of the risk over time are difficult to establish because of the limited time that tests for this virus have been available.

In some embodiments, the individual is co-infected with at least one other organism such as, for example, hepatitis B virus, hepatitis A virus, *staphylococcus aureus*, and/or the human immunodeficiency virus (HIV).

As used herein, spontaneous clearance refers to the ability of an infected individual to clear HCV from their blood without the need for administration of a therapeutic treatment designed to aid such clearance. If an individual is capable of spontaneously clearing an HCV infection, such clearance is typically observed during an acute infection. Authoritative clinical reviews have generally quoted clearance rates as low as 10-15%.

As used herein, the terms treat, treatment, and the like, refer to therapeutic treatment and prophylactic treatment, or preventative measures, wherein the object is to prevent or slow down (lessen) an undesired physiological condition or disease, or obtain beneficial or desired clinical results. In this regard, treatment refers to the administration of a therapeutic agent to slow down or prevent an undesired physiological condition or disease, or the symptoms associated with the above conditions or diseases. In one embodiment, the treatment is one that helps a patient responsive to such treatment reduce the level of HCV RNA present in their body. By association, such a reduction reflects a reduction in the level of HCV present in the patient's body. In one embodiment, the treatment reduces the amount of HCV RNA in the patient's body by at least 50%, at least 75%, at least 85%, at least 95%, or at least 99% during the course of treatment. In one embodiment, treatment completely eliminates HCV RNA from the patient.

With regard to treatments for HCV, methods of the present invention can be used to predict the response to any therapeutic agent useful for treating HCV infections. Generally, treatment for an HCV infection is an interferon based treatment. Thus, in one embodiment, treatment is an interferon-based treatment. In various preferred embodiments, the interferon-based treatment is selected from the group comprising IFN-α, IFN-λ, or any pegylated-interferon. In another embodiment, the interferon-based treatment is combined with ribavirin. In various embodiments, further combinations can include antiprotease drugs and/or other antiviral drugs. In one embodiment, the treatment comprises IFN, ribavirin and an HCV protease inhibitor.

While a treatment for an HCV infection can be administered to help a patient clear an HCV infection, not all patients are responsive to such treatment. That is, in some patients, while the treatment may cause some reduction in the level of HCV RNA, it does not result in a sustained virological response. A patient for whom treatment does not result in a sustained virological response is referred to as a non-responder. Likewise, a patient for whom treatment results in a sustained virological response is referred to as a responder. A sustained virological response is defined as the lack of HCV RNA in the blood 24 weeks after the cessation of treatment. In determining such a result, the HCV RNA level is typically measured at several times points during the course of treatment in order to measure the treatment response. The lower the HCV RNA level is at these time points, the more likely it is that a patient will achieve a sustained virological response.

As used herein, predicting a clinical response refers to knowing the likelihood that a patient will spontaneously clear an HCV infection prior to, or during, the acute phase of infection with HCV. It also refers to knowing the likelihood that a treatment for HCV infection will cause a sufficient reduction in the level of HCV RNA in a patient, before the treatment is administered to the patient. With regard to the present invention, predicting the clinical response may also be referred to as determining the susceptibility of a patient to response, or non-response, to a treatment for HCV infection, or the susceptibility of a patient to spontaneously clearing the virus.

As used herein the terms susceptible, susceptibility, and the like, refer to the likelihood, or probability, an individual will spontaneously clear an HCV infection, or will respond to treatment for such an infection. Such likelihood can also be referred to as a predisposition. In the context of the present invention, the likelihood of spontaneously clearing an HCV infection and/or responding to a treatment need not be absolute. That is, for example, while the presence of IFNL4 protein in the individual decreases the likelihood that the individual will spontaneously clear an HCV infection, or respond to treatment, in a population of patients, all of whom carry the ss469415590 deletion allele (and therefore produce mRNA or IFNL4 protein), some percentage of such population may spontaneously clear an HCV infection or respond to treatment. This is likely due to a combination of other factors such as, for example, the genotype of the virus, race, age, gender, and the genetic makeup of the individual at loci other than those in the IFNL4 gene. Thus, in one embodiment, the absence of IFNL4 protein in a sample from an individual indicates the individual is more likely to spontaneously clear an HCV infection than is a patient that produces the IFNL4 mRNA and protein. In one embodiment, the absence of IFNL4 protein in a sample from an individual indicates the individual is more likely to respond to treatment for an HCV infection than is a patient that produces the IFNL4 protein. Thus, a patient that does not produce the IFNL4 protein is more likely to benefit from administration of a treatment than is a patient that produces IFNL4. In other embodiments, the presence of IFNL4 protein in a sample from an individual indicates the individual is less likely to spontaneously clear an HCV infection than is a patient that does not produce IFNL4. In yet another embodiment, the presence of IFNL4 mRNA and protein in a sample from an individual indicates the individual is less likely to respond to a treatment for an HCV infection than is a patient that does not produce IFNL4 mRNA and protein. Thus, a patient that produces IFNL4 protein is less likely to benefit from administration of a treatment than is a patient not having the particular.

Thus, it will be appreciated by those skilled in the art that, likelihood, susceptibility, predisposition, and the like, are relative terms. Methods and terminology for quantifying and reporting the likelihood of a patient to respond to treatment, or spontaneously clear an HCV infection, are known to those skilled in the art. For example, one such method is a relative indication determined by comparing the number of individuals that produce the IFNL4 mRNA and protein and that spontaneously clear an HCV infection, with the number of individuals that do not produce the IFNL4 mRNA and protein and that also spontaneously clear HCV infection. A similar comparison can be made between individuals that produce the IFNL4 protein and who respond to treatment for an HCV infection, and the number of individuals that do not produce the IFNL4 protein and who respond to treatment for an HCV infection. Such a relative comparison can be illustrated using a fold increase; for example, 1.5 fold (1.5×), 2×, 3×, 5×, etc. Such relative comparison can also be illustrated using a percent increase. For example, if the number of patients that do not produce the IFNL4 protein and that respond to treatment, or spontaneously clear HCV, is twice the number of patients that produce the IFNL4 protein and that respond to treatment, or spontaneously clear the virus, it could be said that individuals lacking the IFANAN protein are 100% more likely to respond to treatment or spontaneously clear HCV. Thus, in various embodiments, an individual that does not produce IFNL4 protein is at least 1.5× (fold), 2.0×, 2.5×, 3.0×, 4.0×, or 5.0×. Thus if an individual is determined to be 2× more likely to spontaneously clear an HCV infection, such a relative number means that in a population representative of the individual, it would be expected that twice as many individuals would spontaneously clear an HCV infection as the number of individuals that would not spontaneously clear an HCV infection.

Relative comparisons can also be illustrated using an odds ratio, which is a statistical method for relative comparisons that is used when selection of study subjects is based on the clinical outcome of interest. In one embodiment, the likelihood of an individual spontaneously clearing an HCV infection, or responding to a treatment for HCV, has an odds ratio of at least about 1.2, at least about 1.4, at least about 1.6, at least about 1.8, at least about 2.0, at least about 2.2, at least about 2.4, at least about 2.6, at least about 2.8, at least about 3.0, at least about 3.2, at least about 3.4, at least about 2.6, at least about 3.8, at least about 4.0, at least about 4.2, at least about 4.4, at least about 4.6, at least about 4.8 or at least about 5.0. Methods of calculating an odds ratio are known to those skilled in the art and are exemplified in Rothman, Kenneth J.; Greenland, Sander; Lash, Timothy L. (2008). Modern Epidemiology, Lippincott Williams & Wilkins, Third edition, which is incorporated herein in its entirety.

In various embodiments, the level of IFNL4 protein in the sample is compared to reference levels of IFNL4 protein (also referred to as reference standards). Such reference standards can be obtained from various sources. For example, the reference standard can be from an individual known to be able to spontaneously clear an HCV infection or respond to treatment for an HCV infection. In another example, the reference standard can be from an individual known to be unable to spontaneously clear an HCV infection or respond to treatment for an HCV infection. Ideally, reference standards represent the average level of protein present in a population of individuals that can, or cannot, clear an HCV infection or respond to treatment for an HCV infection.

In one embodiment, if the level of IFNL4 protein present in the sample from a first individual is less than the level of IFNL4 protein present in a reference standard from a second individual, known to be able to clear an HCV infection or respond to treatment for an HCV infection, or a population of such individuals, then the first individual is predicted to be able to clear an HCV infection or respond to treatment for an HCV infection. In one embodiment, if the level of IFNL4 protein present in the sample from a first individual is greater than the level of IFNL4 protein present in a reference standard from a second individual, known to be able to clear an HCV infection or respond to treatment for an HCV infection, or a population of such individuals, then the first individual is predicted to be unable to clear an HCV infection or respond to treatment for an HCV infection.

As used herein, a biological sample refers to any fluid or tissue from an individual that can be analyzed the activity of the IFNL4 protein, including expression level, protein level or a biological activity of the IFNL4 protein. Examples of the type of sample that can be used to practice the present invention include, but are not limited to, a blood sample, a urine samples, a tear sample, a tissue sample, and a buccal swab. Preferred samples for extracting DNA and genotyping are blood and buccal swab samples. Samples useful for detecting the presence, absence or level of mRNA and protein levels are known to those skilled in the art. Moreover, methods of obtaining such samples are also known to those skilled in the art. IFNL4 expression may be determined in liver biopsies of carriers of a risk genotype and infected by HCV.

Once a sample has been obtained, it is analyzed to determine the presence, absence or level of IFNL4 mRNA and proteins of the present invention. As used herein, the terms "determine," "determine the level of IFNL4 mRNA and protein," "determine the amount of IFNL4 mRNA and protein," "determine the IFNL4 mRNA and protein level", and the like, are meant to encompass any technique which can be used to detect or measure the presence of IFNL4 in a sample. In this context, IFNL4 is an example of an analyte. Such techniques may give qualitative or quantitative results. IFNL4 levels can be determined by detecting the entire IFNL4 mRNA and protein or by detecting fragments, degradation products or reaction products of IFNL4. In a preferred method, the level of IFNL4 is determined using a suitable IFNL4-binding compound.

In the case of a method for determining the likelihood of a response to a treatment for an HCV infection, or resistance to such treatment, according to the present invention, the presence, absence or level of an IFNL4 protein of the present invention indicates the likelihood of the individual to respond to such treatment. In the case of a method of determining the likelihood of spontaneously clearing an HCV infection, according to the present invention, the presence, absence or level of an IFNL4 protein of the present invention indicates the likelihood of the individual spontaneously clearing an HCV infection.

Any known method of analyzing a sample for an analyte can be used to practice the present invention, so long as the method detects the presence, absence, or amount of IFNL4 protein. Examples of such methods include, but are not limited to, immunological detection assays and non-immunological methods (e.g., enzymatic detection assays). In an immunological detection assay, the sample to be tested for the presence, absence or level of an analyte is contacted with a binding molecule, such as an antibody. As used herein, the term contact, contacted, contacting, and the like, refers to the introduction of a sample putatively containing IFNL4 to an IFNL4-binding compound, for example, by combining or mixing the sample with the IFNL4-binding compound. One example of an IFNL4-binding compound is an antibody that selectively binds to IFNL4. However, other molecules that bind to IFNL4 are also encompassed. For example, a receptor to which IFNL4 binds can be used as an IFNL4-binding compound in assays of the present invention.

When IFNL4 is present in the sample, an IFNL4-compound complex is then formed. Such complex formation refers to the ability of an IFNL4-binding compound to selectively bind to the IFNL4 in order to form a stable complex that can be detected. Detection can be qualitative, quantitative, or semi-quantitative. Binding of IFNL4 in the sample to the IFNL4-binding compound is accomplished under conditions suitable to form a complex. Such conditions (e.g., appropriate concentrations, buffers, temperatures, reaction times) as well as methods to optimize such conditions are known to those skilled in the art. Binding can be measured using a variety of methods standard in the art including, but not limited to, enzyme immunoassays (e.g., ELISA), immunoprecipitations, immunoblot assays and other immunoassays as described, for example, in Sambrook et al., supra, and Harlow, et al., supra. These references also provide examples of complex formation conditions.

In one embodiment, the IFNL4/IFNL4-binding compound complex, also referred to herein as an IFNL4-compound complex, or simply the complex, can be formed in solution. In another embodiment, a complex can be formed while the IFNL4-binding compound is immobilized on (e.g., coated onto) a substrate. Immobilization techniques are known to those skilled in the art. Suitable substrate materials include, but are not limited to, plastic, glass, gel, celluloid, fabric, paper, and particulate materials. Examples of substrate materials include, but are not limited to, latex, polystyrene, nylon, nitrocellulose, agarose, cotton, PVDF (polyvinylidene-fluoride), and magnetic resin. Suitable shapes for substrate material include, but are not limited to, a well (e.g., microtiter dish well), a microtiter plate, a dipstick, a strip, a bead, a lateral flow apparatus, a membrane, a filter, a tube, a dish, a celluloid-type matrix, a magnetic particle, and other particulates. Particularly preferred substrates include, for example, an ELISA plate, a dipstick, an immunodot strip, a radioimmunoassay plate, an agarose bead, a plastic bead, a latex bead, a sponge, a cotton thread, a plastic chip, an immunoblot membrane, an immunoblot paper and a flow-through membrane. In one embodiment, a substrate, such as a particulate, can include a detectable marker. For descriptions of examples of substrate materials, see, for example, Kemeny, D. M. (1991) A Practical Guide to ELISA, Pergamon Press, Elmsford, N.Y. pp 33-44, and Price, C. and Newman, D. eds. Principles and Practice of Immunoassay, 2nd edition (1997) Stockton Press, NY, N.Y., both of which are incorporated herein by reference in their entirety.

In one embodiment, an IFNL4-binding compound is immobilized on a substrate, such as a microtiter dish well, a dipstick, an immunodot strip, or a lateral flow apparatus. A sample collected from an individual is applied to the substrate and incubated under conditions suitable (i.e., sufficient) to allow the formation of a complex between the binding compound and any IFNL4 present in the sample.

In accordance with the present invention, once formed, the complex is then detected. As used herein, the term "detecting complex formation" refers to identifying the presence of IFNL4-binding compound complexed to IFNL4. If complexes are formed, the amount of complexes formed can, but need not be, quantified. Complex formation, or selective binding, between a putative IFNL4-composition with an IFNL4-binding compound can be measured (i.e., detected, determined) using a variety of methods standard in the art (see, for example, Sambrook et al. supra.), examples of which are disclosed herein. A complex can be detected in a variety of ways including, but not limited to use of one or more of the following assays: an enzyme-linked immunoassay, a competitive enzyme-linked immunoassay, a radioimmunoassay, a fluorescence immunoassay, a chemiluminescent assay, a lateral flow assay, a flow-through assay, an agglutination assay, a particulate-based assay (e.g., using particulates such as, but not limited to, magnetic particles or plastic polymers, such as latex or polystyrene beads), an immunoprecipitation assay, a BIACORE™ assay (e.g., using colloidal gold), an immunodot assay (e.g., CMG's Immunodot System, Fribourg, Switzerland), and an immunoblot assay (e.g., a western blot), an phosphorescence assay, a flow-through assay, a chromatography assay, a PAGE-based assay, a surface plasmon resonance assay, a spectrophotometric assay, a particulate-based assay, and an electronic sensory assay. Such assays are well known to those skilled in the art.

Assays can be used to give qualitative or quantitative results depending on how they are used. The assay results can be based on detecting the entire IFNL4 molecule or fragments, degradation products or reaction products of IFNL4. Some assays, such as agglutination, particulate separation, and immunoprecipitation, can be observed visually (e.g., either by eye or by a machines, such as a densitometer or spectrophotometer) without the need for a detectable marker.

In other assays, conjugation (i.e., attachment) of a detectable marker to the anti-IFNL4 compound or to a reagent that selectively binds to the anti-IFNL4 compound aids in detecting complex formation. A detectable marker can be conjugated to the anti-IFNL4 compound or reagent at a site that does not interfere with ability of the anti-IFNL4 compound to bind IFNL4 protein. Methods of conjugation are known to those of skill in the art. Examples of detectable markers include, but are not limited to, a radioactive label, a fluorescent label, a chemiluminescent label, a chromophoric label, an enzyme label, a phosphorescent label, an electronic label; a metal sol label, a colored bead, a physical label, or a ligand. A ligand refers to a molecule that binds selectively to another molecule. Preferred detectable markers include, but are not limited to, fluorescein, a radioisotope, a phosphatase (e.g., alkaline phosphatase), biotin, avidin, a peroxidase (e.g., horseradish peroxidase), beta-galactosidase, and biotin-related compounds or avidin-related compounds (e.g., streptavidin or IMMUNOPURE™ NeutrAvidin).

Means of detecting such markers are well known to those of skill in the art. Thus, for example, radiolabels may be detected using photographic film or scintillation counters; fluorescent markers may be detected using a photodetector to detect emitted light. Enzymatic markers are typically detected by providing the enzyme with a substrate and detecting the reaction product produced by the action of the enzyme on the substrate, and colorimetric markers are detected by simply visualizing the colored label.

In one embodiment, an IFNL4-compound complex can be detected by contacting a sample with an antibody specific for the compound, wherein the antibody is conjugated to a detectable marker. A detectable marker can also be conjugated to an anti-IFNL4 antibody or other compound which binds the IFNL4-binding-compound in such a manner as not to block the ability of the anti-compound antibody or other compound to bind to the IFNL4-binding compound being detected. Preferred detectable markers include, but are not limited to, fluorescein, a radioisotope, a phosphatase (e.g., alkaline phosphatase), biotin, avidin, a peroxidase (e.g., horseradish peroxidase), beta-galactosidase, and biotin-related compounds or avidin-related compounds (e.g., streptavidin or IMMUNOPURE™ NeutrAvidin).

In another embodiment, a complex is detected by contacting the complex with an indicator molecule. Suitable indicator molecules include molecules that can bind to the IFNL4/IFNL4-binding molecule complex or to the IFNL4 protein. As such, an indicator molecule can comprise, for example, an IFNL4-binding reagent, such as an antibody. Preferred indicator molecules that are antibodies include, for example, antibodies reactive with the antibodies from species of animal in which the anti-IFNL4 antibodies are produced. An indicator molecule itself can be attached to a detectable marker of the present invention. For example, an antibody can be conjugated to biotin, horseradish peroxidase, alkaline phosphatase or fluorescein.

The present invention can further comprise one or more layers and/or types of secondary molecules or other binding molecules capable of detecting the presence of an indicator molecule. For example, an untagged (i.e., not conjugated to a detectable marker) secondary antibody that selectively binds to an indicator molecule can be bound to a tagged (i.e., conjugated to a detectable marker) tertiary antibody that selectively binds to the secondary antibody. Suitable secondary antibodies, tertiary antibodies and other secondary or tertiary molecules can be readily selected by those skilled in the art. Preferred tertiary molecules can also be selected by those skilled in the art based upon the characteristics of the secondary molecule. The same strategy can be applied for subsequent layers.

Preferably, the indicator molecule is conjugated to a detectable marker. A developing agent is added, if required, and the substrate is submitted to a detection device for analysis. In some protocols, washing steps are added after one or both complex formation steps in order to remove excess reagents. If such steps are used, they involve conditions known to those skilled in the art such that excess reagents are removed but the complex is retained.

One embodiment of the present invention involves the use of a lateral flow assay, examples of which are described in U.S. Pat. No. 5,424,193, issued Jun. 13, 1995, to Pronovost et al.; U.S. Pat. No. 5,415,994, issued May 16, 1995, by Imrich et al; WO 94/29696, published Dec. 22, 1994, by Miller et al.; and WO 94/01775, published Jan. 20, 1994, by Pawlak et al.; all of which are incorporated by reference herein. A lateral flow assay is an example of a single-step assay. In a single-step assay, once the sample has been obtained and made ready for testing, only a single action is necessary on the part of the user to detect the present of an analyte. For example, the sample, in whole or part, can be applied to a device that measures analyte in the sample. In one embodiment, a sample is placed in a lateral flow apparatus that includes the following components: (a) a support structure defining a flow path; (b) a labeling reagent comprising a bead conjugated to a specific antibody, the labeling reagent being impregnated within the support structure in a labeling zone; and (c) a capture reagent. Preferred antibodies include those disclosed herein. The capture reagent is located downstream of the labeling reagent within a capture zone fluidly connected to the labeling zone in such a manner that the labeling reagent can flow from the labeling zone into the capture zone. The support structure comprises a material that does not impede the flow of the beads from the labeling zone to the capture zone. Suitable materials for use as a support structure include ionic (i.e., anionic or cationic) material. Examples of such a material include, but are not limited to, nitrocellulose, PVDF, or carboxymethylcellulose. The support structure defines a flow path that is lateral and is divided into zones, namely a labeling zone and a capture zone. The apparatus can further include a sample receiving zone located along the flow path, preferably upstream of the labeling reagent. The flow path in the support structure is created by contacting a portion of the support structure downstream of the capture zone, preferably at the end of the flow path, to an absorbent capable of absorbing excess liquid from the labeling and capture zones.

In another embodiment, a lateral flow apparatus used to detect IFNL4 includes: (a) a support structure defining a flow path; (b) a labeling reagent comprising a anti-IFNL4 antibody as described above, the labeling reagent impregnated within the support structure in a labeling zone; and (c) a capture reagent, the capture reagent being located downstream of the labeling reagent within a capture zone fluidly connected to the labeling zone in such a manner that the labeling reagent can flow from the labeling zone into the capture zone. The apparatus preferably also includes a sample receiving zone located along the flow path, preferably upstream of the labeling reagent. The apparatus preferably also includes an absorbent located at the end of the flow path. One preferred embodiment includes a capture reagent comprising anti-IFNL4 antibody.

One embodiment of the present invention is a "dipstick" device that can detect IFNL4 in individuals. Dipsticks may be constructed in a variety of ways that partly depend on the way in which they will be used. They may be held directly in a sample (e.g., a urine stream), dipped directly in sample contained in a collection vessel, or have sample applied to a strip contained in a plastic cassette or platform. Another example of a dipstick is a "flow-through" device, an example of which is a heterogenous immunometric assay system based on a capture antibody immobilized onto a membrane attached to an absorbent reservoir, A "bead" refers to a particulate substrate composed of a matrix such as latex or polystyrene, which can be covalently or non-covalently cross-linked to a detection molecule. A preferred embodiment of the "dipstick" assay is an immunometric system, described in U.S. Pat. No. 5,656,502, issued on Aug. 12, 1997, to MacKay and Fredrickson, and U.S. Pat. No. 6,001,658, issued Dec. 14, 1999 to Fredrickson, both incorporated herein by reference. Particularly preferred is an IMMUNODIP™ device available from Diagnostic Chemicals Ltd., PEI, CA.

Once a sample has been analyzed to determine the presence, absence or level of IFNL4, the individual can be selected, or identified, as being able to, or not being able to, spontaneously clear an HCV infection or respond to treatment for such an infection. Such a selection is made using the results from the analysis step of the disclosed method. For example, a person obtaining the result of the analysis step could then decide if the person is able to respond to a treatment for HCV infection and, if not, decide to use an alternative treatment. As a further example, a person reviewing the data obtained from the analysis step could then decide if the person is able to spontaneously clear an HCV infection and, if not, decide to begin administration of a treatment. In one embodiment, the selection is made using a device. For example, a device could be designed such that when the IFNL4 protein is present in the sample, the output of the device indicates the individual is unable to spontaneously clear an HCV infection or respond to treatment for such an infection. In one embodiment, the device is an electronic device. For example, a device that analyzes the results of an ELISA assay could be designed to display the result with regard to the ability of an individual to spontaneously clear an HCV infection or respond to treatment for such an infection. In one embodiment, the device comprises a microprocessor. In one embodiment, the device is a computer.

It has been disclosed herein that when IFNL4 is created by the ss469415590-AG allele, the protein may carry non-synonymous variants that affect the biological activity of the protein. Examples of such variants include (rs73555604 (Cys17Tyr) in exon 1, rs142981501 (Arg60Pro) and rs117648444 (Pro70Ser) in exon 2). It will be appreciated by those skilled in the art that such variations in sequence, when present in the coding portion of the IFNL4 locus, may affect IFNL4 activity and thereby alter the overall impact of an individuals ability to clear the virus or respond to treatment. For example, in a limited population study, the presence of the rs117648444 (Pro70Ser) appeared to correlate with an increased rate of spontaneous clearance as compared to individuals who lacked this variant. Further, this variant has a significantly different Heatmap profile (FIG. 21) as compared to the profiles of rs142981501 (Arg60Pro) and rs117648444 (Pro70Ser). Thus, in one embodiment, if IFNL4 is detected, the method comprises the further step of analyzing the detected IFNL4 for the present of one or more sequence variations, wherein the presence of one or more sequence variations is indicative of the likelihood that an individual will spontaneously clear an HCV infection and/or the likelihood an individual will respond to treatment for an HCV infection.

Since methods of the present invention can be used to predict an individual's response to a therapeutic treatment, such methods can be incorporated into a treatment plan. Thus, one embodiment of the present invention is a method for treating a patient suffering from a chronic hepatitis C virus infection, by analyzing a biological sample from an individual to determine the presence, absence or level of IFNL4 protein present in the biological sample. The decision to administer treatment for a hepatitis C virus infection to the individual is based on the presence, absence or amount of IFNL4 protein present in the sample.

In one embodiment, the patient has an acute HCV infection. In one embodiment, the patient has a chronic HCV infection. In one embodiment, the absence of IFNL4 protein in the sample indicates the individual is likely to respond to a treatment for an HCV infection and thus a treatment is administered. In another embodiment, the presence of IFNL4 protein in the sample indicates that the individual is unlikely to respond to administration of a treatment for an HCV infection, and treatment is not administered. In one embodiment, a level of IFNL4 protein present in the sample is less than the level observed in a reference sample from a second individual, or pool of individuals, known to respond to treatment, indicating that the individual is likely to respond to a treatment for an HCV infection and thus a treatment is administered. In one embodiment, a level of IFNL4 protein present in the sample is higher than the level observed in a reference sample from a second individual, or pool of individuals, known to be unable to respond to treatment or otherwise lacking in response to a treatment for an HCV infection, indicating that the individual is unlikely to respond to a treatment for an HCV infection, and thus a treatment is administered.

The determination of IFNL4 levels in a patient suffering from chronic hepatitis C will enable medical personnel to establish the best hepatitis C treatment regimen for that patient (e.g., nature, dose and duration of hepatitis C treatment and/or other antiviral drugs). For example, if the above method reveals that the patient produces IFNL4 protein, indicating that said subject is unlikely to respond to a hepatitis C treatment, then this subject can be considered as good candidate for newer treatment strategies (such as therapy with higher doses of currently available drugs, longer treatment duration with currently available drugs and/or newer drugs).

The present invention also covers additional methods of treatment using molecules of the present invention. For example, as will be appreciated by now, the presence of IFNL4 protein in an individual results in the individual being unable to spontaneously clear an HCV infection, or respond to treatment for such an infection. Without being bound by theory, the inventors believe that such an effect results from actions of the IFNL4 protein in one or more immunological pathways, for example, activation of the JAK/STAT pathway. Consequently, elimination of such actions should remove the effect. Thus, individuals producing IFNL4, and thus unable to spontaneously clear an HCV infection, or respond to treatment for such an infection, upon administration of a therapeutic compound that eliminates IFNL4 activity should be able to spontaneously clear an HCV infection, or respond to treatment for such an infection. Accordingly, one embodiment of the present invention is a method to treat a patient for an HCV infection, the method comprising administering a compound to the patient, wherein the compound selectively binds to IFNL4 protein in the patient, and wherein such binding results in reducing or eliminating IFNL4 activity in the patient.

One example of such a therapeutic compound is an antibody of the present invention that selectively binds to IFNL4. Administration of such an antibody will result in the antibody binding and forming a complex with IFNL4. Such binding would eliminate IFNL4 activity in at least one of two ways. Physical binding of the antibody to IFNL4 can result in actual physical inhibition of IFNL4 activity. Second, IFNL4-antibody complexes will be recognized by the body and removed there from. IFNL4-binding compounds identified using methods of the present invention can also be used to eliminate or reduce IFNL4 activity in a patient.

In addition to IFNL4-binding compounds, reduction of IFNL4 activity can be achieved by reducing or eliminating the production of mRNA transcripts that encode IFNL4. Such reduction or elimination can be achieved by administration of small interfering RNAs that are specific for mRNA molecules that encode IFNL4. Accordingly, one embodiment of the present invention is a method to treat a patient for an HCV infection, the method comprising administering a small interfering RNA to the patient, wherein the small interfering RNA that is selective for mRNA encoding IFNL4, whereby such administration results in reducing or eliminating IFNL4 activity in the patient.

The present invention also encompasses methods of identifying compounds that regulate IFNL4 activity. Such compounds are referred to as regulators. For example, as previously discussed, the inventors have shown that IFNL4 activates the JAK/STAT pathway, a reaction that can easily be performed using an ELISA assay format. Thus, regulators of IFNL4 activity can be identified by performing a JAK/STAT pathway activation assay using IFNL4 proteins of the present invention, and adding to the assay a test compound. The results of such assay are then compared to the results of a second JAK/STAT activation assay that lacks any test compound, or to which has been added a compound that is known have no effect on IFNL4 activity. Accordingly, one embodiment of the present invention is a method for identifying regulators of IFNL4 protein activity, by incubating IFNL4 protein under conditions that allow measurement of IFNL4 protein activity and measuring the resultant IFNL4 protein activity. The IFNL4 protein can then be incubated in the presence of a test compound under the same conditions used in the initial protein activity assay and the resulting IFNL4 protein activity is measured. The two protein activities are then compared. If the difference between the IFNL4 activity obtained in the absence and the presence of the test compound is statistically significant, the test compound is identified as a regulator of IFNL4 activity.

As used herein, regulators refer to compounds that affect the functional activity of an IFNL4 protein in vitro and/or in vivo. Regulators can be agonists and antagonists of an IFNL4 protein and can be compounds that exert their effect on the IFNL4 protein via the expression, via post-translational modifications, by direct interaction with the IFNL4 protein or by other means. Agonists of IFNL4 protein are molecules that, when bound to IFNL4 protein increase or prolong the functional activity of the protein. Agonists of IFNL4 protein include proteins, nucleic acids, carbohydrates, small molecules, or any other molecule that activate IFNL4 protein. Antagonists of IFNL4 protein are molecules that, when bound to IFNL4 protein, decrease the amount or the duration of the functional activity of the protein. Antagonists include proteins, nucleic acids, carbohydrates, antibodies, small molecules, or any other molecule that decrease the activity of IFNL4 protein.

The term modulate, as it appears herein, refers to a change in the activity of IFNL4 protein. For example, modulation may cause an increase or a decrease in functional activity, binding characteristics, or any other biological, functional, or immunological properties of IFNL4 protein.

Regulators of IFNL4 activity are identified either in assays that employ cells that expressing IFNL4, either naturally or as a result of genetic manipulation (e.g., recombinant cells) (cell-based assays) or in assays with isolated IFNL4 protein (cell-free assays). The various assays can employ a variety of variants of IFNL4 protein (e.g., full-length IFNL4 protein, a biologically active fragment of IFNL4 protein, or a fusion protein that includes all or a portion of IFNL4 protein). The assay can be a binding assay entailing direct or indirect measurement of the binding of a test compound or a known ligand for IFNL4 protein. The assay can also be an activity assay entailing direct or indirect measurement of the IFNL4 protein activity. The assay can also be an expression assay entailing direct or indirect measurement of the expression of mRNA encoding IFNL4 protein, or the IFNL4 protein itself.

Suitable test compounds for use in the screening assays of the invention can be obtained from any suitable source, e.g., conventional compound libraries. The test compounds can also be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. Examples of methods for the synthesis of molecular libraries can be found in the art. Libraries of compounds may be presented in solution or on beads, bacteria, spores, plasmids or phage.

Also included in the present invention are kits useful for practicing the disclosed methods of the present invention. Thus, one embodiment of the present invention is a kit for determining the likelihood of response to a hepatitis C treatment in a subject, in accordance with the present invention, said kit comprising i) reagents for selectively detecting the presence, absence or level of, at least, IFNL4 mRNA or protein in a sample obtained from the subject and ii) instructions for using the kit.

One embodiment of the present invention is a kit for determining the likelihood of spontaneous clearance of hepatitis C virus in a subject infected with the virus, in accordance with the present invention, said kit comprising i) reagents for selectively detecting the presence, absence or level of, at least, IFNL4 protein in a sample obtained from the subject and ii) instructions for using the kit.

Kits of the present invention will contain at least some of the reagents required to determine the presence, absence or level of IFNL4 protein. Reagents for kits of the present invention can include, but are not limited to, isolated nucleic acid molecules of ht present invention, an IFNL4 protein of the present invention, and an IFNL4-binding compound (e.g., an antibody that selectively binds to IFNL4). In some embodiments, the IFNL4 protein and/or IFNL4-binding compounds may be fixed to a solid substrate. The kits may further comprise control proteins. One skilled in the art will, without undue experiments, be able to select the necessary reagents from the disclosure herein, in accordance with the usual requirements. Reagents of the kit may also comprise a molecular label or tag.

Kits of the present invention can also comprise various reagents, such as buffers, necessary to practice the methods of the invention, as known in the art. These reagents or buffers may, for example, be useful to extract and/or purify the IFNL4 mRNA/protein from the biological sample obtained from the subject. The kit may also comprise all the necessary material such as microcentrifuge tubes necessary to practice the methods of the invention.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

It should be appreciated that although methods and materials similar or equivalent to those described herein can be used in the practice or testing of the present invention, suitable methods and materials are described below. All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

EXAMPLES

Example 1. Analysis of the Inducible Expression Landscape in the IFNL3 (IL28B) Region in Primary Human Hepatocytes Activation of Normal Human Hepatocytes Primary cultures of freshly isolated, normal human hepatocytes from HCV-non-infected livers were purchased from Lonza Inc. (Walkersville, Md.). The cells were plated onto six-well, collagen-coated, tissue culture plates and showed high viability. The cells were then treated with PolyI:C at a final concentration of 50 µg/mL for 0, 1, 2, 4, 8 or 24 hours. PolyI:C (polyinosinic:polycytidylic acid) is a Toll-like receptor-3 (TLR3) agonist that simulates viral infection (Alexopoulou L, Holt A C, Medzhitov R, Flavell R A. (2001) Recognition of double-stranded RNA and activation of NF-kappa B by Toll-like receptor 3. *Nature* 413(6857):732-8). PolyI:C is structurally similar to double-stranded RNA, which represents an intermediate phase in the replication cycle of many types of viruses. PolyI:C has been used extensively as a synthetic agent to mimic viral infection, and it induces expression of both type-I (IFN-α) and type-III (IFN-λ) interferons in many cell types (Doyle S E, Vaidya S A, O'Connell R, Dadgostar H, Dempsey P W, Wu T, Rao G, Sun R, Haberland M E, Modlin R L, Cheng G. (2002) IRF3 mediates a TLR3/TLR4-specific antiviral gene program. *Immunity* 17(3):251-63; Doyle S E, O'Connell R, Vaidya S A, Chow E K, Yee K, Cheng G. (2003) Toll-like receptor 3 mediates a more potent anti-viral response than Toll-like receptor 4. *J. Immunol.* 170(7):3565-71). After treating the hepatocyte cultures with PolyI:C for the indicated time periods, the cells were harvested, and DNA and RNA extracts were prepared by standard methods. The quality and quantity of DNA and RNA was measured by Nanodrop and Bioanalyzer analysis.

RNA-sequencing

One microgram of total RNA was used for each of the hepatocyte samples treated with PolyI:C for 0, 1, 2, 4, 8, 24 hours. After PolyA mRNA selection, the RNA samples were fragmented and ligated to 65 bp adaptors to prepare paired end (PE) cDNA libraries with fragments of 200-250 bp, according to a standard Illumina protocol. The libraries were enriched by 12 PCR cycles and sequenced at a concentration of 4.5 pM, using one Genome Analyzer (GAII) lane per sample, generating 107 bp sequencing reads. In average, 47.2±6.6 million PE RNA-seq reads were generated per sample. The human reference genome for the analysis was built based on UCSC hg19 index using Bowtie software. The sequenced reads were processed using Illumina Pipeline OLB 1.9.0 and CASAVA 1.7.0 and aligned to the reference genome using TopHat v1.2.0 after removing some reads according to standard quality control settings. A library of all human transcripts from Ensemble database, version GRCh37.61: useast.ensembl.org/info/data/ftp/index, was used to generate a library of exon junctions and reconstruct splicing forms. Default TopHat algorithm removes from analysis RNA-seq reads that map to more than one genomic region. Considering complexity of the region surrounding IFNL3 (IL28B) gene, we implemented a special strategy. To allow non-exclusive mapping of reads to regions of high similarity, such as IFNL1 (IL29), IFNL2 (IL28A), IFNL3 (IL28B), we changed TopHat settings to allow multiple alignments (up to 10). The mapping identified expression clusters, representing potential exons. Based on the created database of potential splice junctions, previously unmapped reads were re-mapped by TopHat v1.2.0. To detect novel transcripts, the final aligned read files were processed by Cufflinks v0.9.3. Relative abundances of transcripts were measured with fragments per kilobase of exon per million fragments mapped algorithm (FPKM). Confidence intervals for FPKM estimates were calculated using a Bayesian inference method. In the presence of splicing forms, the highest expressing form of each gene was assigned a ratio 1, and all other forms expressed at least at 1% level of the main form (ratio >0.01) were used for analysis. The TopHat alignment algorithm brakes sequence reads into 25-bp segments that are independently mapped and reconstructed back into sequence reads if all individual segments are mapped correctly. To discover possible genetic variants, we allowed 2 or 3 mismatches per segment. Mapping results were visualized using both the UCSC genome browser and a local copy of the Integrative Genomics Viewer (IGV) software: broadinstitute.org/igv/. Genetic variants in the region were visualized by IGV and then examined manually. The results of this analysis are shown in FIG. 1.

Figure 1:
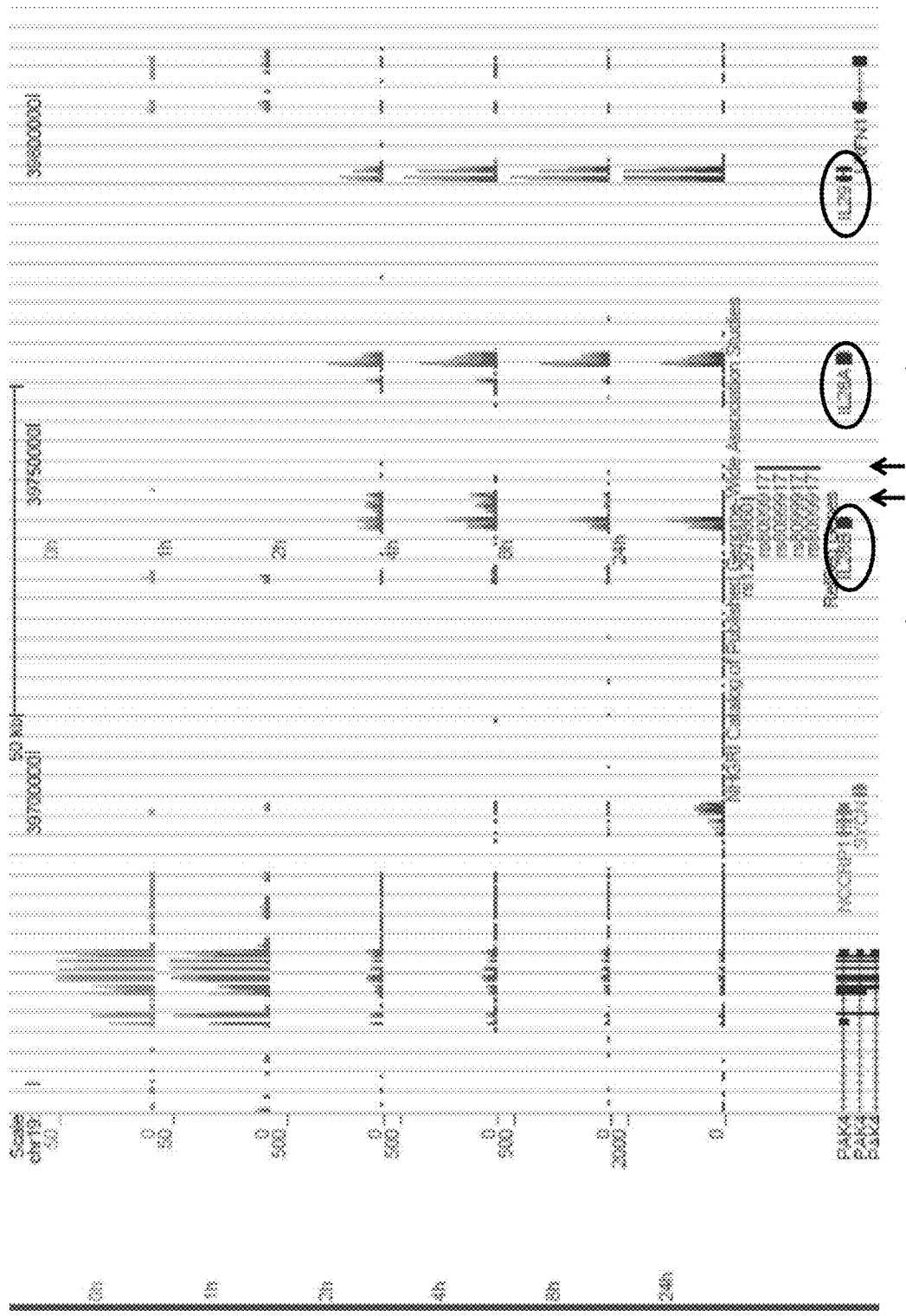
FIG. 1. Results of RNA-sequencing (RNA-seq) in normal primary human hepatocytes activated with 50 ug/ml of PolyI:C for 0, 1, 2, 4, 8, or 24 hours. The results are presented for the 150 Kb genomic region of human chromosome 19 that includes IFNL1 (IL29), IFNL2 (IL28A), IFNL3 (IL28B) and several other genes used as unrelated controls. Location of associated genetic variants rs12979860 and rs8099917 is indicated.

Detailed analysis of the 150 Kb region surrounding the IFNL3 (IL28B) gene showed no expression of known IFN-λ, genes IFNL1 (IL29), IFNL2 (IL28A), IFNL3 (IL28B) after 0 or 1 hour of treatment, but strong activation of these genes after 2-24 hours of treatment (FIG. 1, 2). This analysis also resulted in the identification of a novel, ~2.5 kb long transcribed region located near rs12979860 (FIG. 1, 2, 3). Expression of this region was not detected without, or after 1 hour of, PolyI:C treatment, but was induced after 2, 4 or 8 hours and then strongly decreased at 24 hours. Analysis of paired-end RNA-seq reads identified one splice junction site present in all of the putative transcripts in this region. This sequence was used as a starting point for 5'RACE analysis. Such analysis resulted in the identification of a single transcription start site, followed by a protein translation start site 277 bp downstream (FIG. 3).

Example 2. Analysis of IFNL4 mRNA Expression

An allele-specific TaqMan assay for quantification of IFNL4 mRNA was designed with the Primer Express Software and manufactured by Applied Biosystems on demand. The assay consists of primers:

```
                                         (SEQ ID NO: 13)
IFNL4-p179_forw:     GCCTGCTGCAGAAGCAGAGAT;

(SEQ ID NO: 14)
IFNL4-p179_rev:      AGCCGAGCGCAGGACGA;
``` and probes

```
                                              (SEQ ID NO: 15)
IFNL4_VIC AA (non-risk allele):    ATCGCAGAAGGCC
and
                                              (SEQ ID NO: 16)
IFNL4 FAM-C (risk allele):         ATCGCAGCGGCCC.
```

This assay should provide a fragment of 255 bp with cDNA and no product should be obtained using DNA. The assay is highly specific for the transcript encoding IFNL4-p179 and doesn't detect any other transcripts (IFNL4-p131, p107, etc). FAM fluorofore labels the deletion allele and thus is specific for IFNL4-p179 expression, while detection with VIC fluorofore serves as a negative control, as no IFNL4 p179 should not be detected in mRNA transcripts with the insertion allele.

Due to very high specificity, this assay allows detection even in non-DNAse I treated RNA samples. An alternative expression assay is:

```
                                      (SEQ ID NO: 17)
IFNL4_alt_F: GCCTGCTGCAGAAGCAGAGAT;

(SEQ ID NO: 18)
IFNL4_alt_R: GCTCCAGCGAGCGGTAGTG;
``` and probes

```
                                             (SEQ ID NO: 19)
IFNL4_alt_VIC AA (non-risk allele):   ATCGCAGAAGGCC;

(SEQ ID NO: 20)
IFNL4_alt_FAM-C (risk allele):        ATCGCAGCGGCCC.
```

This assay is has higher efficiency but is less specific than IFNL4-p179. FAM fluorofore detects expression of all forms with risk allele and VIC—all forms with non-risk allele (VIC).

Example 3. Identification and Sequence Analysis of Novel IFNL4 Gene

The full-length open reading frame for IFNL4 transcript was PCR amplified from cDNA of PolyI:C-treated primary human hepatocytes with primers:

```
                                      (SEQ ID NO: 21)
IFNL4 forw: ATGCGGCCGAGTGTCTGGGCC;

(SEQ ID NO: 22)
IFNL4 rev:  GAGGCAAGGCCCAGAGTGTGCAG.
```

Additional sequences were added to primers for cloning into specific vectors. Due to very high GC content of this amplicon, PCR reactions were performed with AmpliTaq Gold 360 Master Mix and 360 GC Enhancer using the touchdown PCR program which includes initial denaturation step with 10 minutes at 95° C., followed by 20 cycles (30 seconds at 95° C., 45 seconds for 2 cycles at each temperature from 70° through 60° C. decreasing by 1° C. at each step, 45 seconds at 72° C.); 25 additional cycles (30 seconds at 95° C., 45 seconds at 60° C. and 45 seconds at 72° C.); and final extension time of 7 minutes at 72° C.

Gel-purified PCR fragments (FIG. 5) were cloned into a C-terminal pFC14A-Halo tag expression vector (Promega) and sequenced for validation. In agreement with RNA-seq data, 3 splicing forms of IFNL4 transcript were detected, including 5, 4 and 3 exons and encoding open reading frames of 179 (SEQ ID NO:2), 131 (SEQ ID NO:5) and 107 (SEQ ID NO:8) amino acids, respectively. FIG. 6 and Table 2 below lists the sequence identifiers assigned to the various open reading frames and the related nucleic acid molecules, as well as other sequences disclosed herein.

TABLE 2

Sequence Identifiers

| SEQ ID NO. | Organism | | Description |
|---|---|---|---|
| 1 | Homo sapiens | | p179 DNA encoding sequence (NCBI accession JN806234) |
| 2 | Homo sapiens | | protein translation of SEQ ID NO: 1 |
| 3 | Homo sapiens | | complement of SEQ ID NO: 1 |
| 4 | Homo sapiens | | p131 DNA encoding sequence (NCBI accession JN806225) |
| 5 | Homo sapiens | | protein translation of SEQ ID NO: 4 |
| 6 | Homo sapiens | | complement of SEQ ID NO: 4 |
| 7 | Homo sapiens | | p107 DNA encoding sequence (NCBI accession JN806226) |
| 8 | Homo sapiens | | protein translation of SEQ ID NO: 7 |
| 9 | Homo sapiens | | complement of SEQ ID NO: 7 |
| 10 | Homo sapiens | from FIG. 7: IFNL binding site 1 | CLMDRHDFG |
| 11 | Homo sapiens | from FIG. 7: IFNL binding site 2 | DEDLLDKFCTELYQQLND |
| 12 | Homo sapiens | from FIG. 7: IFNL binding site 3 | YFRRITLYLTEKKYSP |

TABLE 2-continued

Sequence Identifiers

| SEQ ID NO. | Organism | | Description |
|---|---|---|---|
| 13 | Artificial Seq/primers | IFNL4-p179_forw | GCCTGCTGCAGAAGCAGAGAT |
| 14 | Artificial Seq/primers | IFNL4-p179_rev | AGCCGAGCGCAGGACGA |
| 15 | Artificial Seq/primers | IFNL4_VIC AA (non-risk allele) | ATCGCAGAAGGCC |
| 16 | Artificial Seq/primers | IFNL4 FAM-C (risk allele) | ATCGCAGCGGCCC |
| 17 | Artificial Seq/primers | IFNL4_alt_F | GCCTGCTGCAGAAGCAGAGAT |
| 18 | Artificial Seq/primers | IFNL4_alt_R | GCTCCAGCGAGCGGTAGTG |
| 19 | Artificial Seq/primers | IFNL4_alt_VIC AA (non-risk allele) | ATCGCAGAAGGCC |
| 20 | Artificial Seq/primers | IFNL4_alt FAM-C (risk allele) | ATCGCAGCGGCCC |
| 21 | Artificial Seq/primers | IFNL4 forw | ATGCGGCCGAGTGTCTGGGCC |
| 22 | Artificial Seq/primers | IFNL4 rev | GAGGCAAGGCCCAGAGTGTGCAG |
| 23 | Synthetic peptide | Amino acids 44-74 of IFNL4-p179 | KALRDRYEEEALSWGQRNCSFRPRRDSPRPS |

The first exon of all IFNL4 splicing forms includes a ss469415590-ΔG allele of a previously unreported dinucleotide variant (ss469415590) with two alleles: TT (insertion allele) and ΔG (deletion allele). Protein analysis by BLAST and ClustalW identified strong similarity between IFNL4-p179 protein and IFN-λ proteins with IFNL3 (IL28B) being the most similar protein, with 29.1% and 40.8% amino acid identity and similarity (FIG. 6). The strongest identity between p179 and IFN-λ proteins was found within protein sequences corresponding to the IFN-λ A and F helices, which represent binding sites for the first IFN-λ receptor IFNLR1 (IFN28R1). However, the region of p179 corresponding to the binding site for the second IFN-λ receptor (IL10R2) was highly divergent from that found in IFN-λ proteins (FIG. 7). Therefore, the novel p179 protein is related to but distinct from the interferon-λ family and other known class-2 cytokines.

Figure 8:
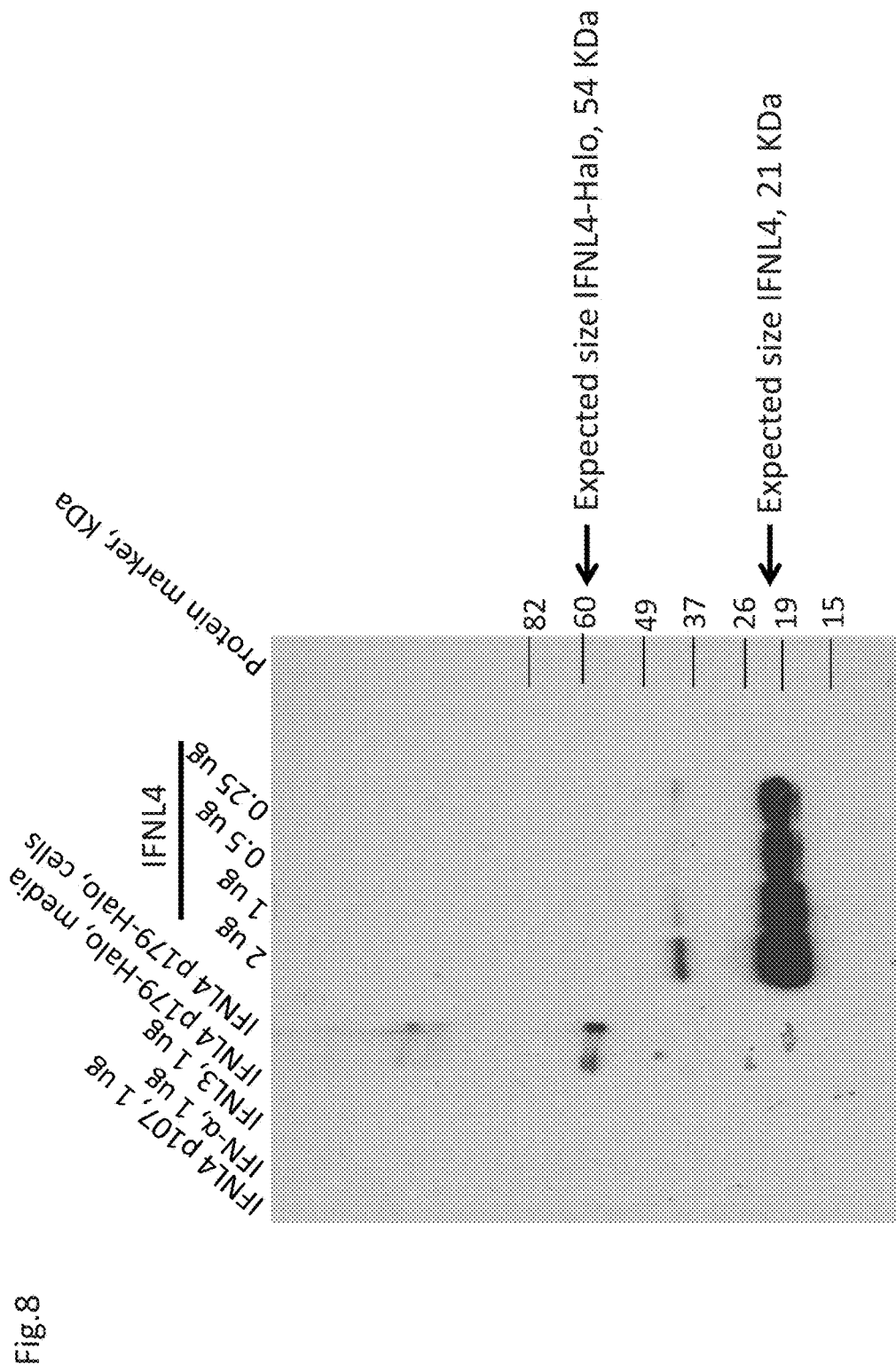
FIG. 8. Western blot protein detection by the mouse anti-IFNL4 monoclonal antibody. Proteins used—purified recombinant IFNL4-p179 at 4 concentrations, crude lysate or conditioned media from HepG2 cells transiently transfected with the IFNL4-p179-Halo expression construct, and purified IFNL4-p107, IFN-α and IFNL3 (IL28B) proteins.
Figure 9:
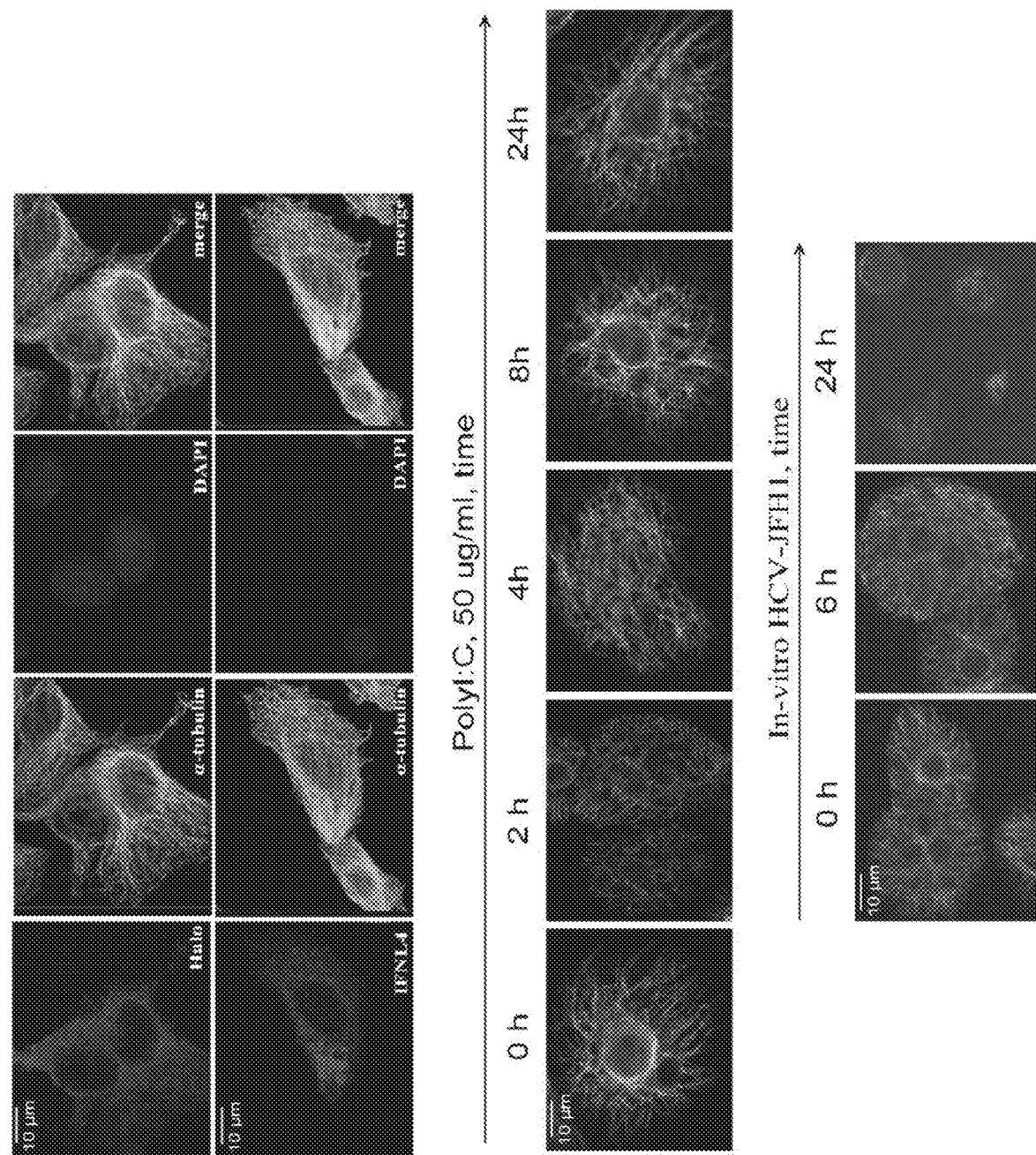
FIG. 9. Confocal imaging of IFNL4 expression with an anti-IFNL4 mouse monoclonal antibody or an anti-Halo antibody in HepG2 cells transiently transfected with IFNL4-Halo expression construct; both antibodies similarly detected intracellular expression of IFNL4.

Example 4. Production of Recombinant IFNL4 Protein and its Detection with an Anti-IFNL4 Monoclonal Antibody C-terminal His-tag fusion constructs carrying the full-length cDNA forms of IFNL4-p179, p131 and p107 were transduced into a baculoviral strain sf9. Since no expression was detected in cell media, the protein was purified from cells. High purity (85-90%) was achieved by several rounds of purification and confirmed by Coomassie staining, and Western blot analyses with anti-His and anti-IFNL4 antibodies (FIG. 8).

Example 5. Development of a Mouse Monoclonal Anti-IFNL4 Antibody

A synthetic peptide KALRDRYEEEALSWGQRNCSFRPRRDSPRPS (SEQ ID NO:23) corresponding to amino acids 44-74 of IFNL4-p179 protein was conjugated with KLH (Keyhole Limpet Hemocyanin) for immunization of mice and with bovine serum albumin (BSA) for screening. The post-immunization titers were accessed from 3 mice using tailbleed serum samples via direct enzyme immune assay (EIA) against the BSA-conjugated peptide. One mouse with best IFNL4-specific titer was chosen for monoclonal antibody production. Splenic B cells from the selected animal were isolated and fused with myeloma partner to create IgG hybridomas. Supernatants from 35 hybridoma clones were collected and screened for recognition of the purified recombinant IFNL4 protein, which resulted in isolation of a monoclonal antibody referred to as Mu anti-hu IFNL4 4G1. Hybridomas expressing Mu anti-hu IFNL4 4G1 were deposited with the American Type Culture Collection (ATCC®) on Feb. 23, 2012 under ATCC Accession Number: PTA-12575. This example illustrates specific detection of IFNL4 protein by the anti-IFNL4 monoclonal antibody clone 4G1 by Western blot and confocal imaging (FIG. 8, 9, 10). Anti-IFNL4 antibody does not recognize IFN-α, IFNL3 (IL28B) or IFNL4-p107, but is specific for detection of IFNL4-p179 and, possibly p131 (at least by confocal imaging). Confocal imaging of transiently transfected IFNL4 expression construct in hepatocellular carcinoma HepG2 cells and endogenous IFNL4 expression in primary human hepatocytes activated with Poly I:C shows intracellular expression (FIG. 10). IFNL4 was not detected by a negative isotype control—anti-IgG antibody. Similar cellular localization was detected both by anti-Halo antibody for the fusion IFNL4-Halo protein and by anti-IFNL4 antibody in HepG2 cells transfected with IFNL4-p179 construct. Location of epitopes for mouse and rabbit anti-IFNL4 antibodies and specific detection patterns are indicated on FIG. 11.

Example 6. Ability of IFNL4 Protein to Activate the JAK/STAT Pathway

Biological activity of IFNL4 expression construct and IFNL4 recombinant purified protein, as well as expression constructs for five other protein isoforms, was evaluated as the ability to activate reporter constructs for 45 human signaling pathways in transiently transfected HepG2 cells. Luciferase Cignal 45-Pathway Finder Reporter Arrays were used according to instructions (Qiagen, full list of reporters tested is available at http://www.sabiosciences.com/reporter_assay_product/HTML/CCA-901L.html). Cells were transfected with expression constructs for p179, p170, p143, p131, p124 and p107 or treated for 24 h with purified recombinant proteins –10 ng/ml of IFN-α or IFNL3 and/or IFNL4-p179. Of all the constructs and proteins tested, only transient transfection with expression construct for IFNL4 and treatment with purified IFN-α (type-I interferon) and IFNL3 (type-III interferon) activated the Interferon-Stimulated Response Element (ISRE)-Luc and IRF3-Luc reporters (FIG. 12).

Type I interferons (IFN-α and -β) and type III interferons (IFN-λ) mediate signaling through STAT1 and STAT2 components of the JAK/STAT-signal transduction pathway. The ISRE-Luc Cignal reporter (Qiagen) encodes the firefly luciferase reporter gene under the control of a minimal (m)CMV promoter linked with tandem repeats which consists of STAT1/STAT2 binding sites (TAGTTT-CACTTTCCC)n that constitute the ISRE. The cells were co-transfected with constitutively expressing *renilla* luciferase, which serves as an internal control for normalizing transfection efficiencies and monitoring cell viability. Some cells were also co-transfected with constructs expressing IFNL4 proteins (p179, p131 and p107) or an empty vector (mock construct), for 72 hours. Other cells were treated with purified recombinant proteins—1, 10 or 100 ng/ml of IFN-α or IFNL3 (IL28B), or IFNL4-p179, p107, for 24 h. All studies were performed using at least 8 biological replicates. Following the specified periods of time, the luciferase and *renilla* expression levels were measured and luciferase/*renilla* ratios were calculated in relation to mock-transfected samples.

The results of the analysis for individual ISRe-Luc assay (FIG. 13) show significant dose-response signaling by of IFN-α or IFNL3, as well as activation by transfected IFNL4-p179, but not by transfected p107, p131, which showed below 25% activity of IFNL4-p179 protein. All studies were performed using at least 8 biological replicates. A HepG2 cell line stably expressing the same ISRE-Luc reporter construct was generated by transduction of cells with a Luciferase Cignal Lenti ISRE reporter construct (Qiagen) and selection of positive clones by growth in DMEM+10% FBS with 1× Antibiotic-Antimycotic (Life Technologies) and 2 ug/mL puromycin. The best HepG2-ISRE-stable clones were identified by testing with purified recombinant IFN-α and IFNL3. The results detected by screening of 45 reporters were independently validated by transient transfections in the HepG2 stable ISRE-Luc cell line (FIG. 13). Transient transfection of IFNL4 construct also induced antiviral activity in Huh7-Lunet cells carrying a subgenomic HCV replicon linked with the luciferase reporter, compared to constructs for non-functional protein isoforms p131 or p107 or an empty GFP vector (mock). The experiments were performed in a 48-well plate and luciferase expression was measured 48 hours post-transfection (FIG. 13).

Example 7. Analysis of STAT1/STAT2 Phosporylation

HepG2 cells in 6-well plates were untreated or transfected with expression constructs or empty Halo-tag vector, or were treated for 1 hour at 37° C. with 50 ng/ml of recombinant IFNL3. Equal amounts (50 µg/lane) of whole-cell lysates prepared 48 hours post-transfection were used for analysis by Western blotting. Detection was performed with rabbit anti-phospho-Tyr701-STAT1 (Cell Signaling Technology) and rabbit anti-phospho-Tyr689-STAT2 (Millipore) antibodies. The blots were stripped and re-probed with rabbit anti-STAT1 and anti-STAT2 antibodies (Santa Cruz Biotechnology) to measure the levels of total STAT1 and STAT2 proteins. Only treatment with IFNL3 and transient expression with IFNL4 construct induced phosphorylation of STAT1 and STAT2 (FIG. 14).

Example 8. Global Analysis of Transcriptome and Pathway Analysis and the Ability of Intracellularly Expressed IFNL4 Protein to Induce Expression of Interferon-Stimulated Genes (ISGs)

HepG2 cells were mock-transfected with an empty Halo-tag vector or with IFNL4-Halo expression construct. High-quality RNA (RIN ~10) prepared from transfected cells (48 hours) was used for sequencing with HiSeq 2000 (Illumina), generating ~300M reads per sample. Standard analysis identified 535 transcripts with >2-fold difference in expression and an FDR<0.05. Ingenuity Pathway Analysis (IPA) performed on this set nominated a list of pathways and specific transcripts (FIG. 15). mRNA expression of selected transcripts was evaluated in specific conditions, in 4 biological replicates, with pathway-based $RT^2$ Profiler PCR arrays, according to instructions (Qiagen)(FIG. 15). HepG2 cells were untreated, or transfected with empty vector (mock); IFNL4-p179, IFNL4-p131 or IFNL4-p107; or treated for 24 hours with 10 ng/ml of IFN-α or IFN-λ, alone of after transfection with mock or IFNL4-p179. Transfected and untransfected cells were treated with IFN-α or IFN-λ at the same time point, corresponding to 24 hours post-transfection and harvested at the same time. Expression of all transcripts on the array (n=90) was analyzed by qRT-PCR pathway profiler arrays with individual specific assays and normalized to expression of four endogenous controls (ACTB, GAPDH, HPRT1 and RPL13A) measured in the same samples. The data is presented on log 2 scale—less negative values indicate higher expression. Error bars indicate mean values with 95% confidence intervals (FIG. 15).

Transient transfection with IFNL4 construct activated the same set of ISGs induced by interferons. In samples already expressing IFNL4 no further activation of ISGs could not be achieved by additional treatment with interferons.

Example 9. Differential Activation of ISRE-Luc Reporter in Human Cell Lines

ISRE-Luc reporter was transiently co-transfected into HepG2 (hepatocellular carcinoma), 293T (embryonal kidney) and HeLa (cervical carcinoma) cell lines, together with empty vector, or constructs for IFNL4, on non-functional forms p131 or 107. Alternatively, ISRE-Luc reporter transfected cells were treated with interferons, at indicated concentrations. ISRE-Luc activation by IFNL4 was induced only in HepG2 and 293T cells (FIG. 16).

Example 10. Site-Directed Mutagenesis of IFNL4

Further, 83 single-point mutants of IFNL4-p179 were created and their activity was evaluated after transient expression in HepG2 cells, using the ISRE-Luc reporter and compared to activity of IFNL4-p179 (FIG. 17). Site directed mutagenesis was performed using the QuikChange Lightning Site-Directed Mutagenesis Kit (Agilent). Primers were designed to change the first base of a codon in order to mutate specific IFNL4 amino acids. The original IFNL4-p179 plasmid was used as template for individual PCR reactions with mutagenesis primer pairs. The PCR products were digested with DpnI enzyme to eliminate original non-mutated template, the derived plasmids were pooled and transformed into One Shot TOP10 Competent Cells. Individual colonies were sequenced for validation. FIG. 17 and Table 3 show distribution and type of IFNL4 mutants and their relative potential to transactivate ISRE-Luc reporter construct.

TABLE 3

Induction of a transiently transfected ISRE-Luc reporter construct in HepG2 cells by IFNL4 mutants. Activity of mutants is relative to IFNL4-p179.

| number | group | residue | AA change | fold to IFNL4 | t-test to IFNAN | average fold |
|---|---|---|---|---|---|---|
| 1 | cysteines | 17 | C 17 Y (SNP) | 1.04 | 6.32E−01 | 0.28 |
| 2 | | 27 | C 27 G | 0.09 | 3.00E−06 | |
| 3 | | 62 | C 62 R | 0.26 | 3.61E−10 | |
| 4 | | 76 | C 76 S | 0.06 | 7.24E−13 | |
| 5 | | 122 | C 122 G | 0.11 | 3.70E−06 | |
| 6 | | 152 | C 152 G | 0.13 | 4.65E−06 | |
| 7 | | 178 | C 178 G | 0.25 | 4.67E−12 | |
| 8 | conserved | 19 | V 19 M | 1.05 | 6.37E−01 | 0.66 |
| 9 | | 25 | R 25 G | 0.92 | 3.02E−01 | |
| 10 | | 34 | S 34 P | 0.05 | 2.36E−12 | |
| 11 | | 35 | L 35 M | 0.95 | 4.55E−01 | |
| 12 | | 37 | P 37 A | 0.11 | 4.90E−11 | |
| 13 | | 40 | L 40 M | 0.77 | 1.14E−03 | |
| 14 | | 42 | A 42 P | 0.08 | 1.26E−11 | |
| 15 | | 44 | K 44 E | 0.10 | 2.48E−11 | |
| 16 | | 48 | D 48 H | 0.44 | 4.12E−10 | |
| 17 | | 51 | E 51 K | 0.45 | 1.23E−07 | |
| 18 | | 52 | E 52 K | 1.14 | 5.35E−03 | |
| 19 | | 55 | L 55 M | 0.99 | 9.11E−01 | |
| 20 | | 64 | F 64 V | 0.95 | 4.71E−01 | |
| 21 | | 69 | D 69 H | 0.88 | 2.47E−02 | |
| 22 | | 78 | R 78 G | 0.72 | 6.74E−05 | |
| 23 | | 87 | A 87 P | 0.15 | 9.63E−06 | |
| 24 | | 92 | V 92 M | 0.90 | 3.88E−02 | |
| 25 | | 93 | L 93 I | 1.08 | 7.23E−02 | |
| 26 | | 101 | L 101 M | 1.00 | 9.77E−01 | |
| 27 | | 112 | L 112 M | 0.35 | 4.80E−11 | |
| 28 | | 121 | A 121 P | 1.09 | 7.04E−02 | |
| 29 | | 126 | A 126 P | 0.84 | 1.65E−01 | |
| 30 | | 128 | P 128 A | 0.89 | 1.69E−01 | |
| 31 | | 140 | R 140 G | 0.92 | 2.26E−01 | |
| 32 | | 149 | S 149 P | 0.88 | 1.15E−02 | |
| 33 | | 150 | P 150 A | 1.15 | 7.06E−02 | |
| 34 | | 155 | A 155 P | 0.82 | 1.87E−03 | |
| 35 | | 156 | S 156 G | 1.12 | 2.78E−02 | |
| 36 | | 157 | V 157 L | 0.48 | 3.40E−07 | |
| 37 | | 159 | F 159 V | 0.70 | 2.44E−05 | |
| 38 | | 160 | N 160 D | 0.49 | 4.57E−08 | |
| 39 | | 161 | L 161 F | 0.25 | 5.21E−08 | |
| 40 | | 163 | R 163 G | 0.14 | 8.74E−13 | |
| 41 | | 164 | L 164 M | 0.70 | 1.24E−05 | |
| 42 | | 165 | L 165 F | 0.24 | 5.08E−12 | |
| 43 | | 166 | T 166 P | 0.40 | 4.35E−10 | |
| 44 | | 169 | L 169F | 0.78 | 5.92E−05 | |
| 45 | | 173 | A 173 P | 0.12 | 6.59E−12 | |
| 46 | non-conserved | 2 | R 2 G | 1.07 | 3.13E−01 | 0.90 |
| 47 | | 3 | P 3 A | 0.77 | 7.58E−03 | |
| 48 | | 4 | S 4 G | 1.07 | 2.51E−01 | |
| 49 | | 5 | V 5 F | 0.84 | 4.52E−02 | |
| 50 | | 10 | A 10 P | 1.13 | 7.06E−02 | |
| 51 | | 11 | A 11 P | 0.98 | 7.69E−01 | |
| 52 | | 13 | L 13 M | 0.86 | 4.98E−03 | |
| 53 | | 15 | V 15 F | 1.04 | 5.95E−01 | |
| 54 | | 20 | I 20 V | 1.24 | 5.50E−04 | |
| 55 | | 21 | A 21 P | 0.99 | 8.56E−01 | |
| 56 | | 28 | L 28 M | 1.15 | 1.64E−01 | |
| 57 | | 29 | L 29 F | 0.24 | 2.79E−06 | |

TABLE 3-continued

Induction of a transiently transfected ISRE-Luc reporter construct in HepG2 cells by IFNL4 mutants. Activity of mutants is relative to IFNL4-p179.

| number | group | residue | AA change | fold to IFNL4 | t-test to IFNAN | average fold |
|---|---|---|---|---|---|---|
| 58 | | 30 | S 30 P | 0.12 | 1.26E−07 | |
| 59 | | 32 | Y 32 N | 0.08 | 1.41E−12 | |
| 60 | | 50 | Y 50 N | 0.29 | 6.52E−11 | |
| 61 | | 57 | W 57 R | 1.18 | 1.42E−01 | |
| 62 | | 60 | R 60 P (SNP) | 1.44 | 1.79E−01 | |
| 63 | | 61 | N 61 H | 1.00 | 9.43E−01 | |
| 64 | | 63 | S 63 P | 1.31 | 2.24E−04 | |
| 65 | | 65 | R 65 G | 0.89 | 2.93E−01 | |
| 66 | | 70 | P 70 S (SNP) | 1.10 | 1.68E−01 | |
| 67 | | 71 | P 71 T | 0.99 | 7.85E−01 | |
| 68 | | 72 | R 72 G | 0.95 | 3.56E−01 | |
| 69 | | 102 | L 102 F | 1.01 | 9.24E−01 | |
| 70 | | 111 | L 111 M | 0.26 | 4.88E−13 | |
| 71 | | 116 | G 116 R | 0.98 | 7.46E−01 | |
| 72 | | 118 | D 118 H | 0.47 | 3.09E−04 | |
| 73 | | 120 | A 120 P | 0.13 | 4.42E−06 | |
| 74 | | 129 | G 129 A | 0.98 | 9.86E−01 | |
| 75 | | 130 | S 130 P | 0.81 | 7.95E−02 | |
| 76 | | 132 | R 132 G | 1.08 | 6.74E−02 | |
| 77 | | 135 | P 135 A | 0.99 | 6.86E−01 | |
| 78 | | 139 | K 139 R | 1.08 | 2.00E−01 | |
| 79 | | 143 | K 143 E | 1.18 | 3.24E−02 | |
| 80 | | 146 | R 146 K | 1.19 | 5.59E−03 | |
| 81 | | 154 | K 154 E | 1.05 | 4.54E−01 | |
| 82 | | 158 | V 158 I | 0.91 | 4.22E−01 | |
| 83 | | 162 | L 162 M | 1.25 | 8.27E−03 | |

Analysis of 83 IFNL4 mutants separated in 3 groups: cysteines (n=7), non-cysteine residues conserved (n=38) and non-conserved in IFNL3 (n=38). The analysis showed that the 6 non-polymorphic cysteines are critical for biological activity of IFNL4 as their mutations eliminate IFNL4 biological activity. Only one cysteine, corresponding to a natural genetic polymorphism Cys17Tyr, did not affect biological activity of IFNL4. Mutants of residues conserved between IFNL3 and IFNL4 show stronger impact on biological activity of IFNL4 (FIG. 18).

Example 11. Analysis of Biological Activity of 3 Natural Polymorphic Variants of IFNL4

When IFNL4 is created by ss469415590-ΔG allele, the protein may carry 3 additional coding non-synonymous variants (rs73555604 (Cys17Tyr) in exon 1, rs142981501 (Arg60Pro) and rs117648444 (Pro70Ser) in exon 2), all present in different IFNL4 haplotypes (FIG. 19). Biological activity of these variants (Cys17Tyr, Arg60Pro and Pro70Ser) was compared to a construct for the wild-type IFNL4 after transient expression of all expression constructs into HepG2 cells, in three biological replicates. RNA was extracted 48 hours post-transfection, converted to cDNA and assayed for 96 qRT-PCR assays included in the anti-viral qPCR panel (Qiagen). Expression of all transcripts was normalized to expression of 4 endogenous controls. Transcripts significantly differing (n=33) between cells transfected by WT-IFNL4 and mutants were used for further analysis with principal components analysis (PCA). Principal components analysis (PCA) based on expression of 33 transcripts involved in antiviral response measured by qRT-PCR in HepG2 transiently transfected with specific allelic protein constructs, in three biological replicates. The PCA plot shows that Pro70Ser mutant affects expression of transcripts differently from both the WT-IFNL4 and the group of Cys17Tyr and Arg60Pro mutants which cluster close to each other. Heatmap plot of transcripts with expression significantly affected by transient expression of IFNL4 allelic protein constructs (WT-IFNL4, Cys17Tyr, Arg60Pro and Pro70Ser) in HepG2 cells, based on results of experiment on FIG. 20. Mutants Cys17Tyr and Arg60Pro show similar effects on these transcripts, while Pro70Ser showed most difference with WT-IFNL4, causing lower expression of IL15, IL18, CTSB, FOS and SPP1 transcripts compared to cells transfected with WT-IFNL4, and higher expression of DAK, IRF7, DHX58 and APOBEC3G transcripts compared to cells transfected with WT-IFNL4. Color chart corresponds to log 2 scale difference in expression caused by mutants compared to WT-IFNL4.

The breadth and scope of the present invention should not be limited by any of the above-described exemplary embodiments, but should be defined only in accordance with the following claims and their equivalents.

What is claimed:

1. A nucleic acid molecule that encodes the amino acid sequence of SEQ ID NO: 2 and at least one amino acid sequence feature selected from the group consisting of:
   (a) at least one amino acid substitution, as compared to SEQ ID NO:2, selected from A10P, A11P, L13M, V15F, C17Y, V19M, I20V, A21P, R26G, L28M, L35M, L40M, E52K, L55M, W57R, R60P, N61H, S63P, F64V, R65G, D69H, P70S, P71T, R72G, R78G, V92M, L93I, L101M, L102F, G116R, A121P, A126P, P128A, G129A, S130P, R132G, P135A, K139R, R140G, K143E, R146K, S149P, P150A, K154E, A155P, S156G, F159V, L162M, L164M, and L169F;
   (b) at least one amino acid substitution as compared to SEQ ID NO:2 selected from A10P, A11P, L13M, V15F, C17Y, V19M, I20V, A21P, R26G, L28M, L35M, L40M, E52K, L55M, W57R, R60P, N61H, S63P, F64V, R65G, D69H, P70S, P71T, R72G, G116R, A121P, A126P, P128A, G129A, S130P, R132G, P135A, K139R, R140G, K143E, R146K, S149P, P150A, K154E, A155P, S156G, F159V, L162M, L164M, and L169F;
   (c) has at least one amino acid substitution as compared to SEQ ID NO:2 selected from A10P, A11P, L13M, V15F, C17Y, V19M, I20V, A21P, R26G, L28M, L35M, L40M, G116R, A121P, A126P, P128A, G129A, S130P, R132G, P135A, K139R, R140G, K143E, R146K, S149P, P150A, K154E, A155P, S156G, V158I, F159V, L162M, L164M, and L169F; or
   (d) at least one amino acid substitution as compared to SEQ ID NO:2 selected from C27G, S34P, P37A, D48H, C62R, A87P, D118H, A120P, C122G, C152G, V157L, N160D, L161F, L164M, L165F, T166P, L169F, and A173P.

2. The nucleic acid molecule of claim 1, wherein the variant sequence has at least one amino acid substitution, relative to SEQ ID NO:2, selected from A10P, A11P, L13M, V15F, V19M, I20V, A21P, R26G, L28M, L35M, L40M, E52K, L55M, W57R, N61H, S63P, F64V, R65G, D69H, P71T, R72G, R78G, V92M, L93I, L101M, L102F, G116R, A121P, A126P, P128A, G129A, S130P, R132G, P135A, K139R, R140G, K143E, R146K, S149P, P150A, A155P, S156G, F159V, L162M, L164M, and L169F.

3. The nucleic acid molecule of claim 1, wherein the variant sequence has at least one amino acid substitution, relative to SEQ ID NO:2, selected from A10P, A11P, L13M, V15F, V19M, I20V, A21P, R26G, L28M, L35M, L40M, E52K, L55M, W57R, N61H, S63P, F64V, R65G, D69H, P71T, R72G, G116R, A121P, A126P, P128A, G129A, S130P, R132G, P135A, K139R, R140G, K143E, R146K, S149P, P150A, A155P, S156G, F159V, L162M, L164M, and L169F.

4. The nucleic acid molecule of claim 1, wherein the variant sequence has at least one amino acid substitution, as compared to SEQ ID NO:2, selected from A10P, A11P, L13M, V15F, V19M, I20V, A21P, R26G, L28M, L35M, L40M, G116R, A121P, A126P, P128A, G129A, S130P, R132G, P135A, K139R, R140G, K143E, R146K, S149P, P150A, A155P, S156G, F159V, L162M, L164M, and L169F.

5. The nucleic acid molecule of claim 1, wherein the variant sequence has at least one amino acid substitution, relative to SEQ ID NO:2, selected from C27G, S34P, P37A, D48H, C62R, A87P, D118H, A120P, C122G, C152G, V157L, N160D, L161F, L164M, L165F, T166P, L169F, and A173P.

6. The nucleic acid molecule of claim 1, wherein the variant sequence has at least one amino acid substitution, relative to SEQ ID NO:2, selected from A10P, I20V, L28M, E52K, W57R, S63P, A121P, K143E, P150A, S156G, and L162M.

7. A recombinant vector comprising the nucleic acid molecule of claim 1.

8. A plasmid comprising the nucleic acid molecule of claim 1.

9. The nucleic acid molecule of claim 1, that is inserted into a vector capable of delivering the nucleic acid molecule into a host cell.

10. The nucleic acid molecule of claim 9, operatively linked to at least one transcription control sequence capable of regulating expression of the nucleic acid molecule in a cell.

11. A recombinant vector comprising a nucleic acid sequence encoding a protein comprising a variant amino acid sequence that is 85% to 96% identical to SEQ ID NO:2, wherein the variant amino acid sequence comprises at least one sequence feature selected from the group consisting of:
   a. a cysteine residue at the position corresponding to position 27 of SEQ ID NO:2;
   b. a leucine residue at the position corresponding to position 29 of SEQ ID NO:2
   c. a serine residue at the position corresponding to position 30 of SEQ ID NO:2
   d. a tyrosine residue at the position corresponding to position 32 of SEQ ID NO:2
   e. a serine residue at the position corresponding to position 34 of SEQ ID NO:2
   f. a proline residue at the position corresponding to position 37 of SEQ ID NO:2;
   g. a leucine residue at the position corresponding to position 40 of SEQ ID NO:2;
   h. an alanine residue at the position corresponding to position 42 of SEQ ID NO:2;
   i. a lysine residue at the position corresponding to position 44 of SEQ ID NO:2;

j. an aspartic acid residue at the position corresponding to position 48 of SEQ ID NO:2;
k. a tyrosine residue at the position corresponding to position 50 of SEQ ID NO:2;
l. a leucine residue at the position corresponding to position 111 of SEQ ID NO:2;
m. a leucine residue at the position corresponding to position 112 of SEQ ID NO:2;
n. an aspartic acid residue at the position corresponding to position 118 of SEQ ID NO:2;
o. an alanine residue at the position corresponding to position 120 of SEQ ID NO:2;
P. a cysteine residue at the position corresponding to position 122 of SEQ ID NO:2;
q. a cysteine residue at the position corresponding to position 152 of SEQ ID NO:2;
r. a valine residue at the position corresponding to position 157 of SEQ ID NO:2;
s. an asparagine residue at the position corresponding to position 160 of SEQ ID NO:2;
t. a leucine residue at the position corresponding to position 161 of SEQ ID NO:2;
u. an arginine residue at the position corresponding to position 163 of SEQ ID NO:2
v. a leucine residue at the position corresponding to position 165 of SEQ ID NO:2;
w. a threonine residue at the position corresponding to position 166 of SEQ ID NO:2;
x. an alanine residue at the position corresponding to position 173 of SEQ ID NO:2; and
y. a cysteine residue at the position corresponding to position 178 of SEQ ID NO:2.

12. The recombinant vector of claim 11, wherein the variant amino acid sequence comprises:
a. a cysteine residue at the position corresponding to position 27 of SEQ ID NO:2;
b. a leucine residue at the position corresponding to position 29 of SEQ ID NO:2
c. a serine residue at the position corresponding to position 30 of SEQ ID NO:2
d. a tyrosine residue at the position corresponding to position 32 of SEQ ID NO:2
e. a serine residue at the position corresponding to position 34 of SEQ ID NO:2
f. a proline residue at the position corresponding to position 37 of SEQ ID NO:2;
g. a leucine residue at the position corresponding to position 40 of SEQ ID NO:2;
h. an alanine residue at the position corresponding to position 42 of SEQ ID NO:2;
i. a lysine residue at the position corresponding to position 44 of SEQ ID NO:2;
j. an aspartic acid residue at the position corresponding to position 48 of SEQ ID NO:2;
k. a tyrosine residue at the position corresponding to position 50 of SEQ ID NO:2;
l. a leucine residue at the position corresponding to position 111 of SEQ ID NO:2;
m. a leucine residue at the position corresponding to position 112 of SEQ ID NO:2;
n. an aspartic acid residue at the position corresponding to position 118 of SEQ ID NO:2;
o. an alanine residue at the position corresponding to position 120 of SEQ ID NO:2;
p. a cysteine residue at the position corresponding to position 122 of SEQ ID NO:2;
q. a cysteine residue at the position corresponding to position 152 of SEQ ID NO:2;
r. a valine residue at the position corresponding to position 157 of SEQ ID NO:2;
s. an asparagine residue at the position corresponding to position 160 of SEQ ID NO:2;
t. a leucine residue at the position corresponding to position 161 of SEQ ID NO:2;
u. an arginine residue at the position corresponding to position 163 of SEQ ID NO:2
v. a leucine residue at the position corresponding to position 165 of SEQ ID NO:2;
w. a threonine residue at the position corresponding to position 166 of SEQ ID NO:2;
x. an alanine residue at the position corresponding to position 173 of SEQ ID NO:2; and
y. a cysteine residue at the position corresponding to position 178 of SEQ ID NO:2.

13. The recombinant vector of claim 11, wherein the variant amino acid sequence is 85% to 94% identical to SEQ ID NO:2.

14. A recombinant vector comprising a nucleic acid molecule that sequence encoding a protein comprising a variant amino acid sequence that is 85% to 96% identical to SEQ ID NO:2, wherein the variant amino acid sequence comprises at least one sequence feature selected from the group consisting of:
a. a cysteine residue at the position corresponding to position 27 of SEQ ID NO:2;
b. a leucine residue at the position corresponding to position 29 of SEQ ID NO:2
c. a serine residue at the position corresponding to position 30 of SEQ ID NO:2
d. a tyrosine residue at the position corresponding to position 32 of SEQ ID NO:2
e. a serine residue at the position corresponding to position 34 of SEQ ID NO:2
f. a proline residue at the position corresponding to position 37 of SEQ ID NO:2;
g. a leucine residue at the position corresponding to position 40 of SEQ ID NO:2;
h. an alanine residue at the position corresponding to position 42 of SEQ ID NO:2;
i. a lysine residue at the position corresponding to position 44 of SEQ ID NO:2;
j. an aspartic acid residue at the position corresponding to position 48 of SEQ ID NO:2;
k. a tyrosine residue at the position corresponding to position 50 of SEQ ID NO:2;
l. a leucine residue at the position corresponding to position 111 of SEQ ID NO:2;
m. a leucine residue at the position corresponding to position 112 of SEQ ID NO:2;
n. an aspartic acid residue at the position corresponding to position 118 of SEQ ID NO:2;
o. an alanine residue at the position corresponding to position 120 of SEQ ID NO:2;
P. a cysteine residue at the position corresponding to position 122 of SEQ ID NO:2;
q. a cysteine residue at the position corresponding to position 152 of SEQ ID NO:2;
r. a valine residue at the position corresponding to position 157 of SEQ ID NO:2;
s. an asparagine residue at the position corresponding to position 160 of SEQ ID NO:2;
t. a leucine residue at the position corresponding to position 161 of SEQ ID NO:2;

u. an arginine residue at the position corresponding to position 163 of SEQ ID NO:2
v. a leucine residue at the position corresponding to position 165 of SEQ ID NO:2;
w. a threonine residue at the position corresponding to position 166 of SEQ ID NO:2;
x. an alanine residue at the position corresponding to position 173 of SEQ ID NO:2; and
y. a cysteine residue at the position corresponding to position 178 of SEQ ID NO:2;

and wherein the variant sequence has at least one amino acid substitution, relative to SEQ ID NO:2, selected from A10P, A11P, L13M, V15F, V19M, I20V, A21P, R26G, L28M, L35M, L40M, E52K, L55M, W57R, N61H, S63P, F64V, R65G, D69H, P71T, R72G, R78G, V92M, L93I, L101M, L102F, G116R, A121P, A126P, P128A, G129A, S130P, R132G, P135A, K139R, R140G, K143E, R146K, S149P, P150A, A155P, S156G, F159V, L162M, L164M, and L169F.

15. The recombinant vector of claim 14, wherein the variant sequence has at least one amino acid substitution, relative to SEQ ID NO:2, selected from A10P, A11P, L13M, V15F, V19M, I20V, A21P, R26G, L28M, L35M, L40M, E52K, L55M, W57R, N61H, S63P, F64V, R65G, D69H, P71T, R72G, G116R, A121P, A126P, P128A, G129A, S130P, R132G, P135A, K139R, R140G, K143E, R146K, S149P, P150A, A155P, S156G, F159V, L162M, L164M, and L169F.

16. The recombinant vector of claim 14, wherein the variant sequence has at least one amino acid substitution, relative to SEQ ID NO:2, selected from A10P, A11P, L13M, V15F, V19M, I20V, A21P, R26G, L28M, L35M, L40M, G116R, A121P, A126P, P128A, G129A, S130P, R132G, P135A, K139R, R140G, K143E, R146K, S149P, P150A, A155P, S156G, V158I, F159V, L162M, L164M, and L169F.

17. The recombinant vector of claim 14, wherein the variant sequence has at least one amino acid substitution, relative to SEQ ID NO:2, selected from C27G, S34P, P37A, D48H, C62R, A87P, D118H, A120P, C122G, C152G, V157L, N160D, L161F, L164M, L165F, T166P, L169F, and A173P.

18. The recombinant vector of claim 14, wherein the variant sequence has at least one amino acid substitution, relative to SEQ ID NO:2, selected from A10P, I20V, L28M, E52K, W57R, S63P, A121P, K143E, P150A, S156G, and L162M.

19. The recombinant vector of claim 14, wherein the variant amino acid sequence is 85% to 94% identical to SEQ ID NO:2.

* * * * *